United States Patent
Posner et al.

(10) Patent No.: US 6,380,408 B1
(45) Date of Patent: Apr. 30, 2002

(54) NON-CALCEMIC, ANTIPROLIFERATIVE, TRANSCRIPTIONALLY ACTIVE SULFUR-CONTAINING ANALOGS OF 1α, 25-DIHYDROXY VITAMIN $D_3$

(75) Inventors: Gary H. Posner, Baltimore, MD (US); Jae-Kyoo Lee, Andover, MA (US); Qiang Wang, Newark, CA (US); Kenneth R. Crawford, Baltimore, MD (US); Gyoonhee Han, Nara (JP)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/541,060

(22) Filed: Mar. 31, 2000

Related U.S. Application Data

(60) Provisional application No. 60/127,328, filed on Apr. 1, 1999, and provisional application No. 60/128,478, filed on Apr. 9, 1999.

(51) Int. Cl.[7] .................... C07C 401/00; A61K 31/593
(52) U.S. Cl. ........................ 552/653; 514/167
(58) Field of Search ................. 514/167; 552/653

(56) References Cited

U.S. PATENT DOCUMENTS

| | | | |
|---|---|---|---|
| 4,011,250 A | 3/1977 | Ishikawa et al. | 260/397.2 |
| 4,224,231 A | 9/1980 | DeLuca et al. | 260/397.2 |
| 5,190,935 A | 3/1993 | Binderup et al. | 514/167 |
| 5,260,290 A | 11/1993 | DeLuca et al. | 514/167 |
| 5,274,142 A | 12/1993 | Posner et al. | 552/653 |
| 5,376,651 A | 12/1994 | Binderup | 514/167 |
| 5,389,622 A | 2/1995 | Posner et al. | 514/167 |
| 5,401,731 A | 3/1995 | Calverley et al. | 514/167 |
| 5,401,732 A | 3/1995 | Calverley et al. | 514/167 |
| 5,403,832 A | 4/1995 | Posner et al. | 514/167 |
| 5,554,599 A | 9/1996 | Grue-Sorenson et al. | 514/167 |
| 5,830,885 A | 11/1998 | Posner | 514/167 |
| 6,043,386 A | 3/2000 | Posner et al. | 552/653 |

OTHER PUBLICATIONS

Chodynski et al. (DN 127:190902, abstract of Steroids, (1997), 62(7), 546–553).*

* cited by examiner

Primary Examiner—S. Qazi
(74) Attorney, Agent, or Firm—Arent Fox Kintner Plotkin & Kahn PLLC

(57) ABSTRACT

Novel sulfur-containing analogs of 1α,25-dihydroxy vitamin $D_3$ are provided. These analogs are synthesized in a convergent manner by joining A-ring and C,D ring fragments. Each analog with 1α,3β-substituent stereochemistry shows a pharmacologically desirable combination of high antiproliferative and high transcriptional activities in vitro and also low calcemic activity in vivo.

13 Claims, 3 Drawing Sheets

NON-CALCEMIC, ANTIPROLIFERATIVE, TRANSCRIPTIONALLY ACTIVE SULFUR-CONTAINING ANALOGS OF 1α, 25-DIHYDROXY VITAMIN D₃

This Application claim benefit to Provisional Application No. 60/127,328 filed Apr. 1, 1999 which claims benefit to No. 60/128,478 filed Apr. 9, 1999.

The invention described and claimed herein was made in part under a grant from the National Institutes of Health. The U.S. Government has certain rights in the invention.

FIELD OF THE INVENTION

The present invention relates to novel analogs of the hormone 1α,25 dihydroxy vitamin $D_3$. Such analog materials exhibit a pharmacologically desirable combination of high antiproliferative and high transcriptional activity in vitro along with no or low calcemic activity in vivo.

BACKGROUND OF THE INVENTION

Because of its extraordinarily high potency in regulating diverse biochemical events vital to good health in humans, 1α,25-dihydroxy vitamin $D_3$, also known as calcitriol or 1,25$D_3$, has stimulated the worldwide interest of medical researchers, molecular biologists, pharmacologists, medicinal and organic chemists, and researchers in the area of products for personal care and cancer prevention and/or treatment. This Material corresponds to the structure set forth in Formula I.

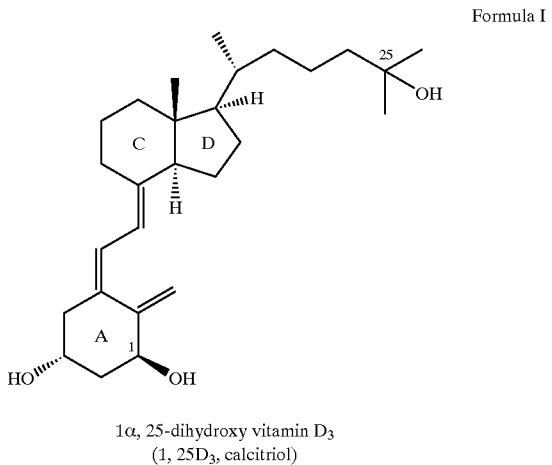

Formula I

1α, 25-dihydroxy vitamin D₃
(1, 25D₃, calcitriol)

Numerous references can be cited as showing prior work with respect to vitamin $D_3$ analogues, calcitriol or the like. See, for example:

*Vitamin D. Chemical, Biochemical and Clinical Update,* Proceedings of the Sixth Workshop on Vitamin D, Merano, Italy, March 1985; Norman, A. W., Schaefer, K., Grigoleit, H. G., Herrath, D. V. Eds.; W. de Gruyter; New York, 1985; Brommage, R., DeLucca, H. F., *Endocrine Rev.* (1985) 6:491; Dickson, I., *Nature* (1987) 325:18; Cancela, L., Theofon, G., Norman, A. W., in *Hormones and Their Actions.* Part I; Cooke, B. A., King, R. J. B., Van der Molen, H. J. Eds.; Elsevier, Holland, 1988; Tsoukas, D. C., Provvedini, D. M., Manolagas, S. C., *Science,* (Washington, D.C.) (1984) 224:1438; Provvedini, D. M., Tsoukas, C. D., Deftoe, L. J., Manolagas, S. C., *Science* (Washington, D.C.) (1983) 221:1181; *Vitamin D. Chemical Biochemical, and Clinical Endocrinology of Calcium Metabolism,* Proceedings of the Fifth Workshop on Vitamin D, Williamsburg, Va., February 1982, Norman, A. W., Schaefer, K., Herrath, D. V., Grigoleit, H. G., Eds., W. de Gruyter, New York, 1982, pp. 901–940; Calverley, M. J. in *Vitamin D: Molecular, Cellular, and Clinical Endocrinology,* Norman, A. W., Ed., de Gruyter; Berlin, 1988, p. 51; Calverley, M. J., *Tetrahedron* (1987) 43:4609. *Vitamin D, A Pluripotent Steroid Hormone: Structural Studies, Molecular Endocrinology and Clinical Applications,* ed. Norman, Boullion and Thomasset, 1994, Walter de Gruyter, New York. Calverley and Binderup, *Bioorganic & Medicinal Chemistry Letters* (1993) 3:1845. U.S. Pat. Nos. 5,274,142; 5,389,622; 5,403,832 and 5,830,885 also describe and claim vitamin $D_3$ analogs. The entire contents of each reference and patent cited above and elsewhere in the present application are hereby incorporated by reference.

A major chemical challenge has been to design and synthesize analogs of 1α,25-dihydroxy vitamin $D_3$ that retain potent antiproliferative and pro-differentiating activities but that lack hypercalcemic activity. Some synthetic analogs exhibiting such selective physiological activities, like 1α, 25-dihydroxy-16-ene-23-yne-26,27-hexafluorocholecalciferol developed by Hoffman-La Roche, have been shown to possess very desirable pharmacological properties. Only a few 24-fluoro and 24,24-difluoro analogs of 1,25$D_3$, having natural A-ring substituents and stereochemistry, have been synthesized. They have been shown, however, to be disappointingly similar to 1,25$D_3$ in terms of calcemic activity. Although their binding affinity to the vitamin D receptor (VDR) is similar to that of calcitriol, such materials do have longer plasma half-lives.

Given the foregoing, it is clear that there is a continuing need to identify additional synthetic analogs of the hormone 1α,25-dihydroxy vitamin $D_3$, which analogs selectively exhibit desirable pharmacological activities but do not exhibit hypercalcemic activity. Accordingly, it is an object of the present invention to provide novel 1,25$D_3$ analogs which are useful for a wide variety of beneficial medicinal and/or personal care product uses but which do not exhibit undesirably high levels of calcemic activity in vivo.

SUMMARY OF THE INVENTION

The present invention relates to novel sulfur-containing, and optionally fluorinated, unsaturated and/or oxa-containing analogs of 1α,25-dihydroxy vitamin $D_3$. Such analogs have the diastereoisomeric structural formulas set forth as Formulas II, III, IV, V, VI, VII, VIII, IX and X.

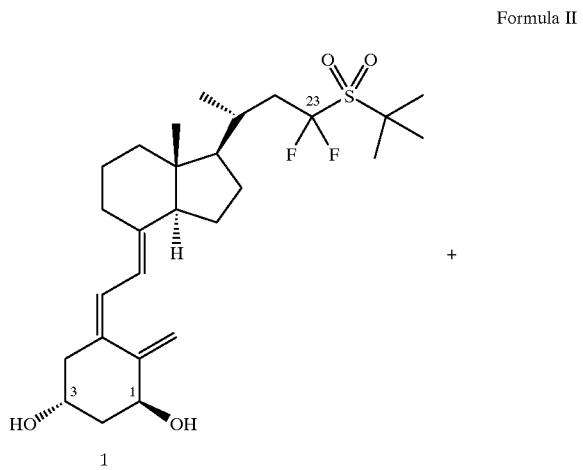

Formula II

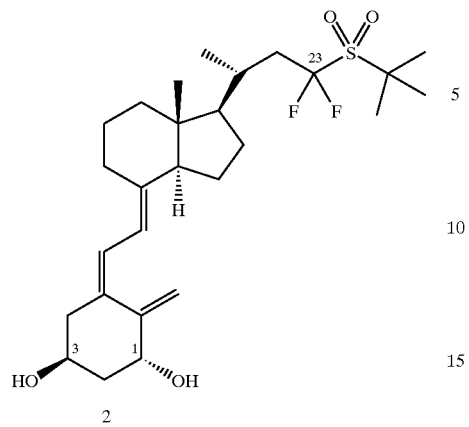
Formula III
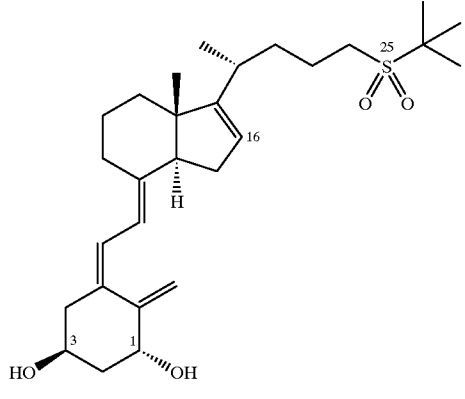
Formula V
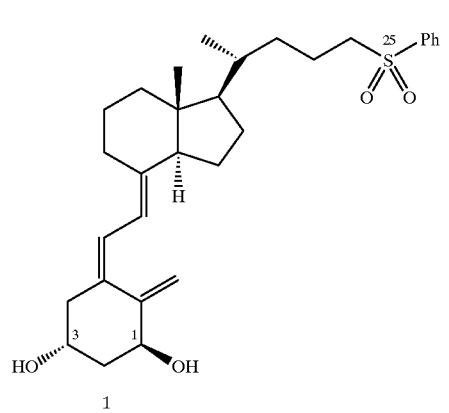
+
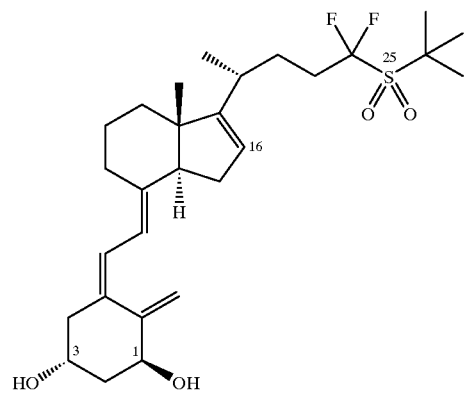
+
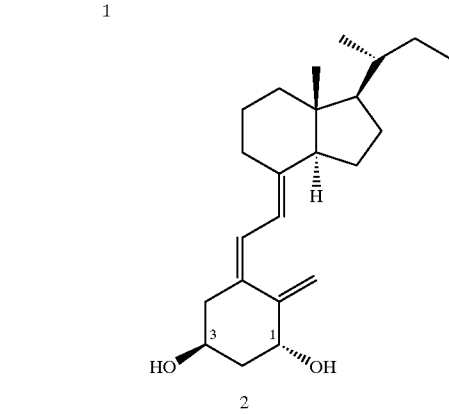
Formula IV
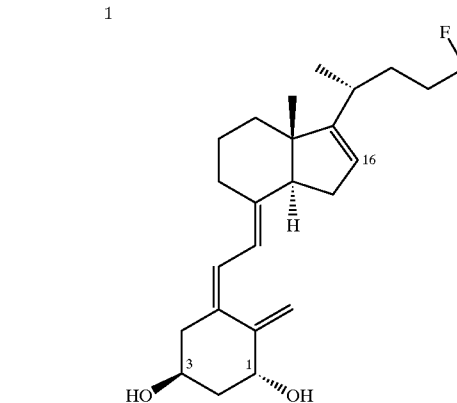
Formula VI
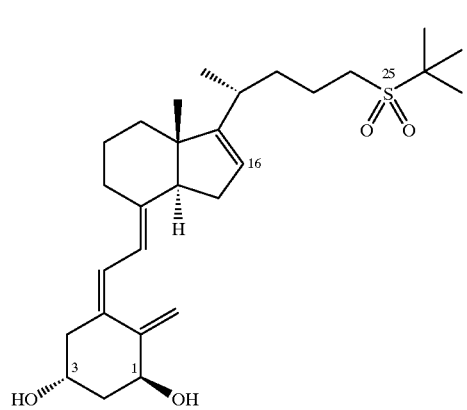
+
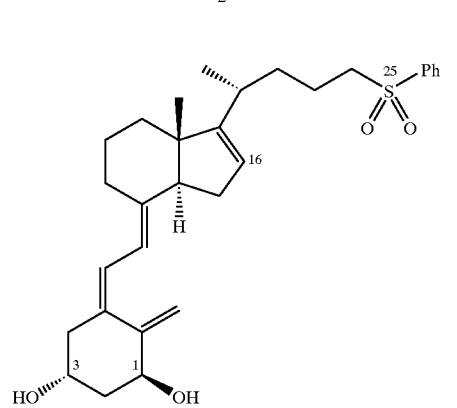
+

5
-continued
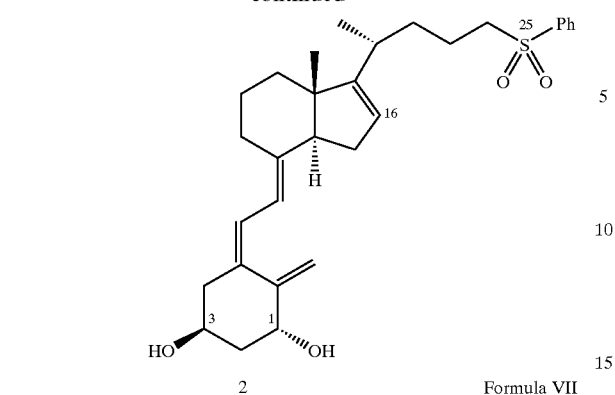
Formula VII
Formula VIII
6
-continued
Formula IX
Formula X
+
+
+
+

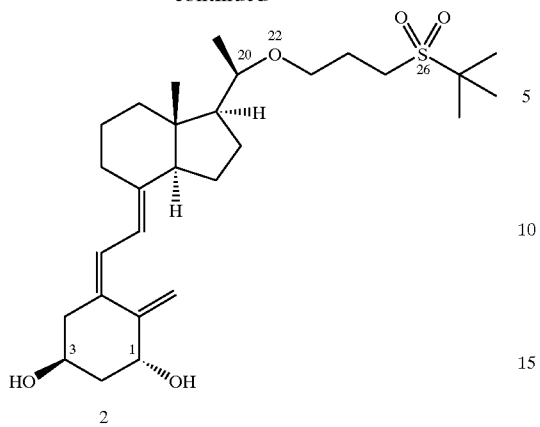

Formula XVI

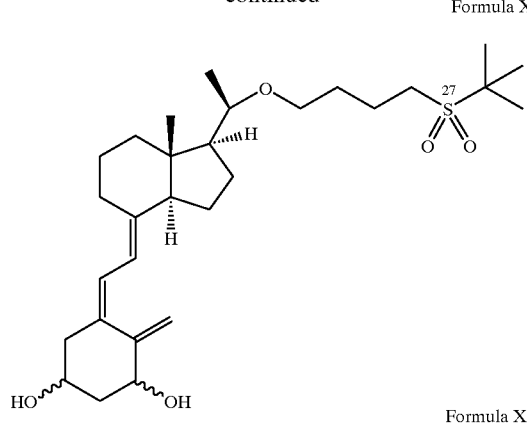

Formula XVII

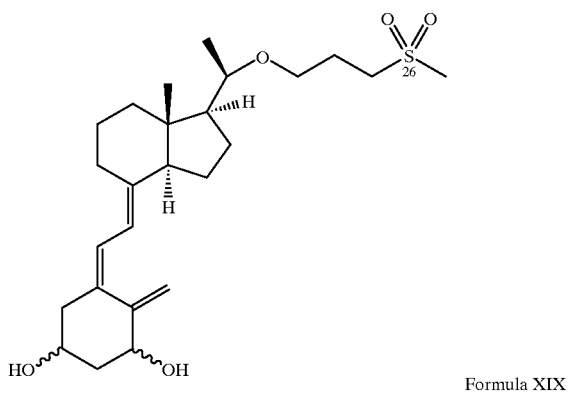

In Formulae II–X and other compounds of the invention, the hydroxyl substituents at Position 1 and at position 3 on the A-ring can be such that the analogs are either in the (−), i.e. (1α, 3β) or the (+), i.e. (1β, 3α), diastereomeric configuration. The C—O bonds at these positions are occasionally indicated by wavy lines in structural formulae hereinbelow to indicate that alternative configurations are intended. Compounds with substituents in the (1α, 3β) diastereomeric configuration are preferred according to the invention.

The present invention also includes materials which are similar to the compounds of Formulae II–X but which have 23-oxa-25-sulfone, 20-epi-22-oxasulfone; 16-ene-alkenyl sulfone; 16-ene-alkynyl sulfone; and 22E, 24E diene sulfone units. Compounds represented by Formulae XIV–XVII and XIX are among the preferred compounds of the invention:

Formula XIV

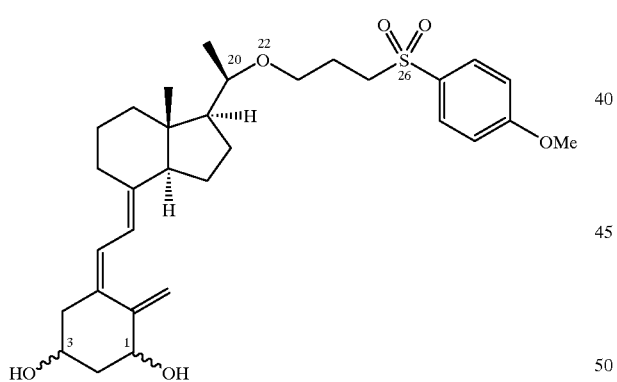

Formula XV

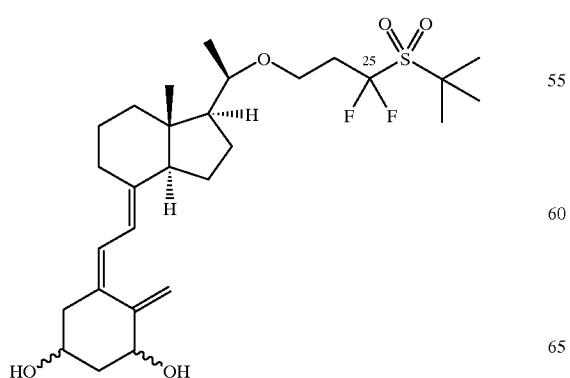

Formula XIX

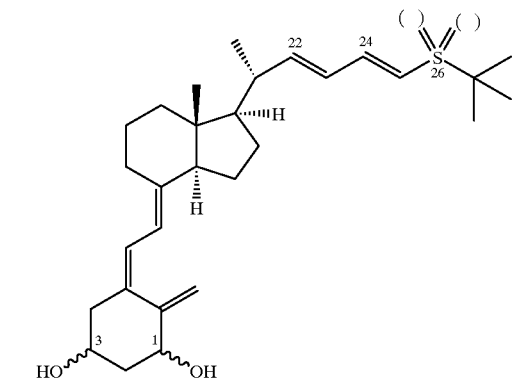

Compounds of the invention can be represented by the general formulae XI–XIII and XVIII Formula XI

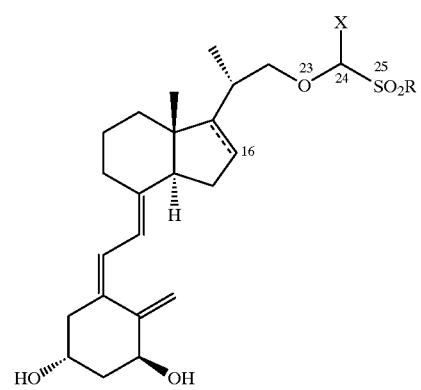

wherein X is $H_2$ or $F_2$ and R is a branched or straight chain lower alkyl (1–6 carbons), an unsubstituted phenyl group or a phenyl group substituted with a lower alkyl or alkoxy group. Compounds wherein R is methyl, t-butyl, phenyl, and methoxyphenyl are especially preferred.

Formula XII

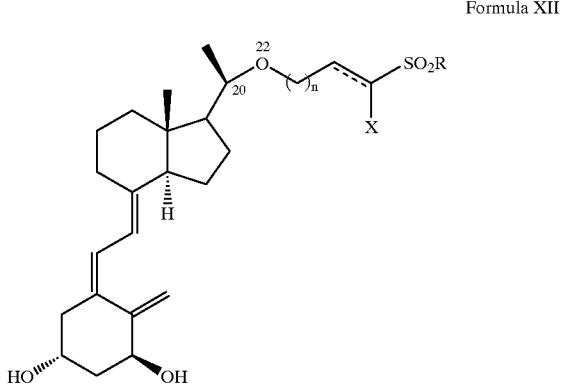

wherein X is $H_2$ or $F_2$ and R is a branched or straight chain lower alkyl (1–6 carbons), an unsubstituted phenyl group or a phenyl group substituted with a lower alkyl or alkoxy group. Compounds wherein R is methyl, t-butyl, phenyl, and methoxyphenyl are especially preferred.

Formula XIII

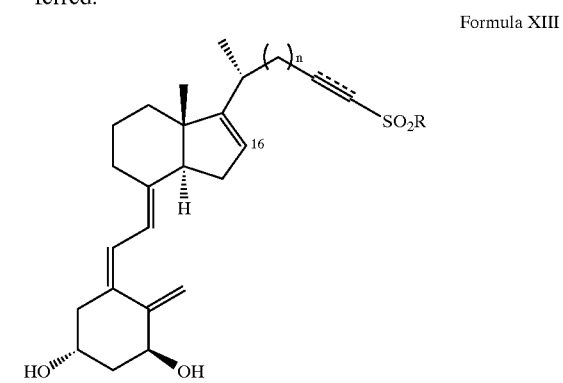

wherein n is 1 or 2, and R is a branched or straight chain lower alkyl (1–6 carbons), an unsubstituted phenyl group or a phenyl group substituted with a lower alkyl or alkoxy group. Compounds wherein R is methyl, t-butyl, phenyl, and methoxyphenyl are especially preferred.

Formula XVIII

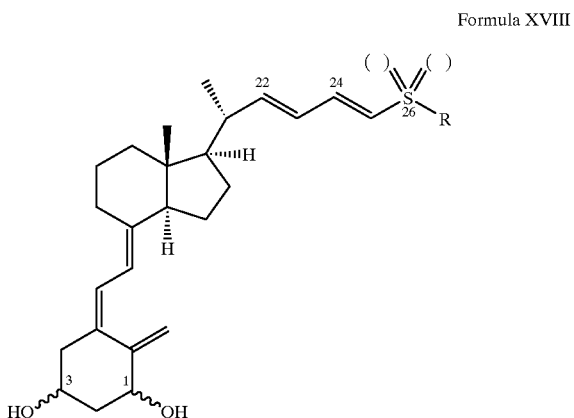

wherein R is a branched or straight chain lower alkyl (1–6 carbons), an unsubstituted phenyl group or a phenyl group substituted with a lower alkyl or alkoxy group. Compounds wherein R is methyl, t-butyl, phenyl, and methoxyphenyl are especially preferred.

DETAILED DESCRIPTION OF THE INVENTION

Figure 1:
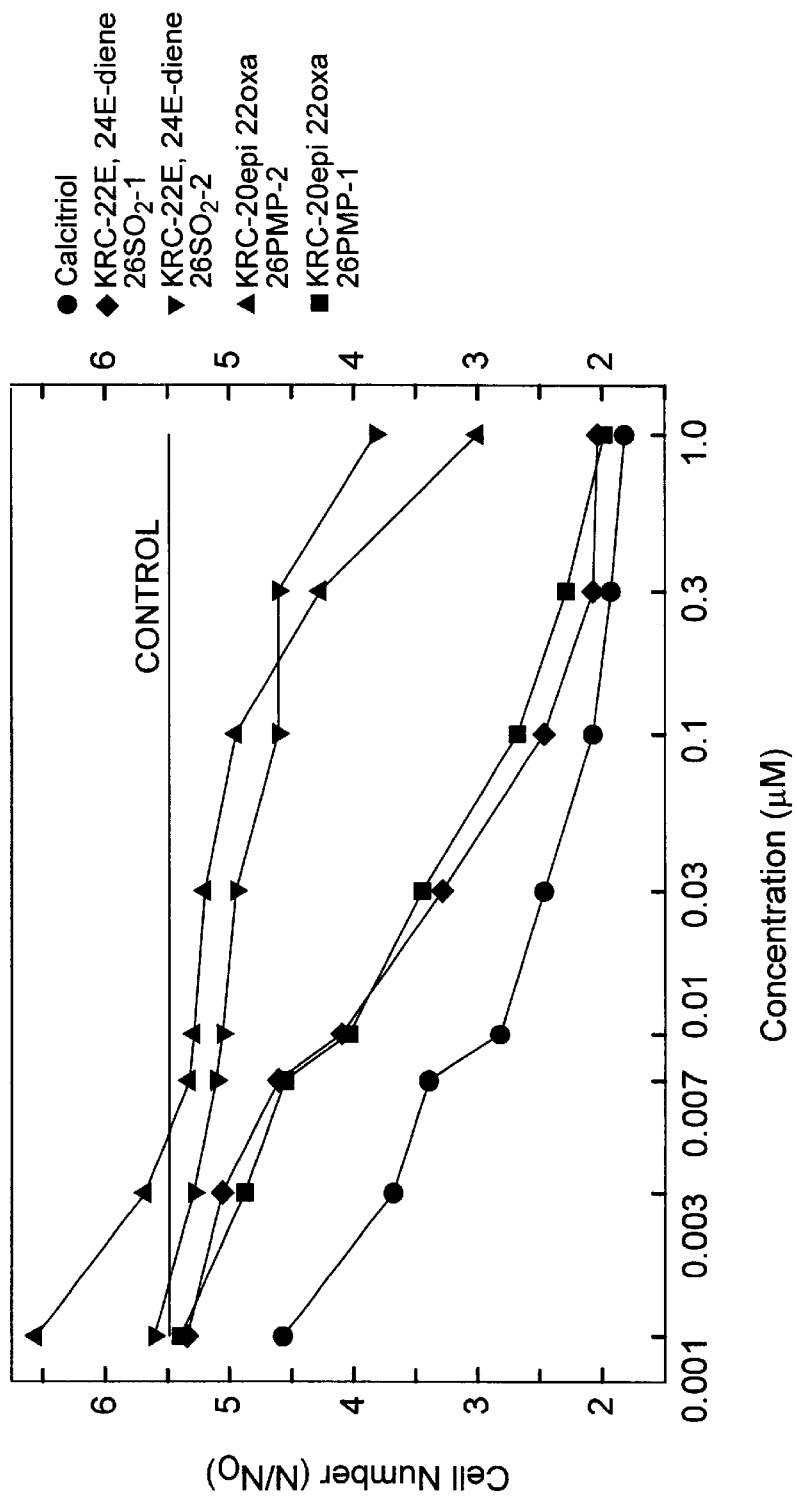
FIG. 1: Dose response effects of vitamin $D_3$ analogs on keratinocyte proliferation. $N_0$ represents the number of cells at zero hours and $N_1$ represents the number of cells at 96 hours. KRC 22E, 24Ediene 26SO2-1=compound 23a; KRC 22E, 24Ediene 26SO2-2=compound 23b; KRC-20epi 22oxa 26 PMP-1=compound 15a; KRC-20epi 22oxa 26 PMP-2=compound 15b.

In preparing the calcitrol analogs corresponding to Formulas II–VIII, several considerations are taken into account in order to arrive at the desired combination of substitutents which will diminish calcemic activity yet also provide potently pro-differentiating side chains. Position 24 on the side chain is typically the site of side chain metabolic oxygenation. Therefore, it is believed that replacing C—H by stronger C—F bonds at this position should increase lifetime of such an analog in vivo. Further, the atomic size of a fluorine substituent closely matches that of a hydrogen atom, thereby causing no steric hindrance to receptor binding. Further, it is postulated that the presence of two fluorine atoms should increase the lipophilicity of the analog relative to its non-fluorinated counterpart, thereby enhancing rates of absorption and transport in vivo. Further, presence of a t-butylsulfone group at position 24 or 25 is expected to simulate the polar environment in that region characteristic of the natural polar 25-OH group. Finally, a 16-ene carbon-carbon double bond often potentiates antiproliferative activity.

Taking these considerations into account, the sulfur-containing, and optionally fluorine-containing, unsaturated and oxa-containing analogs of the present invention can be prepared via multi-step organic synthesis reaction procedures as set forth hereinafter in Schemes 1, 2, 3, 4, 5, 6, 7, 8 and 9. Steps in the reaction process as depicted in the schemes are described in the examples following each scheme.

Unless otherwise noted, in all of the examples, reactions are run in flame-dried round-bottomed flasks under an atmosphere of ultra high purity (UHP) argon. Diethyl ether (ether) and tetrahydrofuran (THF) are distilled from sodium benzophenone ketyl prior to use. Methylene chloride ($CH_2Cl_2$) is distilled from calcium hydride prior to use. All other compounds are purchased from Aldrich Chemical Company and used without further purification. Analytical thin-layer chromatography (TLC) is conducted with Silica Gel 60 $F_{254}$ plates (250 μm thickness, Merck). Column chromatography is performed using short path silica gel (particle size<230 mesh), flash silica gel (particle size 400–230 mesh), or Florisil® (200 mesh). Yields are not optimized. Purity of products is judged to be >95% based on their chromatographic homogeneity. High performance liquid chromatography (HPLC) is carried out with a Rainin HPLX system equipped with two 25 mL/min preparative pump heads using Rainin Dynamax 10 mm×250 mm (semipreparative) columns packed with 60 Å silica gel (8 μm pore size), either as bare silica or as C-18-bonded silica. Melting points are measured using a Mel-Temp metal-block apparatus and are uncorrected. Nuclear magnetic resonance (NMR) spectra are obtained either on a Varian XL-400 spectrometer, operating at 400 MHz for $^1$H and 100 MHz for $^{13}$C or on a Varian XL-500 spectrometer, operating at 500 MHz for $^1$H and 125 MHz for $^{13}$C. Chemical shifts are reported in parts per million (ppm, δ) downfield from tetramethylsilane. Infrared (IR) spectra are obtained using a Perkin-Elmer 1600 FT-IR spectrometer. Resonances are reported in wavenumbers (cm$^{-1}$). Low and high resolution mass spectra (LRMS and HRMS) are obtained with electronic or chemical ionization (EI or CI) either (1) at Johns Hopkins University on a VG Instruments 70-S spectrometer run at 70 eV for EI and run with ammonia (NH$_3$) as a carrier gas for CI, or (2) at the University of Illinois at Champaign-Urbana on a Finnigan-MAT CH5, a Finnigan-MAT 731, or a VG Instruments 70-VSE spectrometer run at 70 eV for EI and run with methane (CH$_4$) for CI.

Preparation of the Formula II materials is set forth in Scheme 1 as follows.

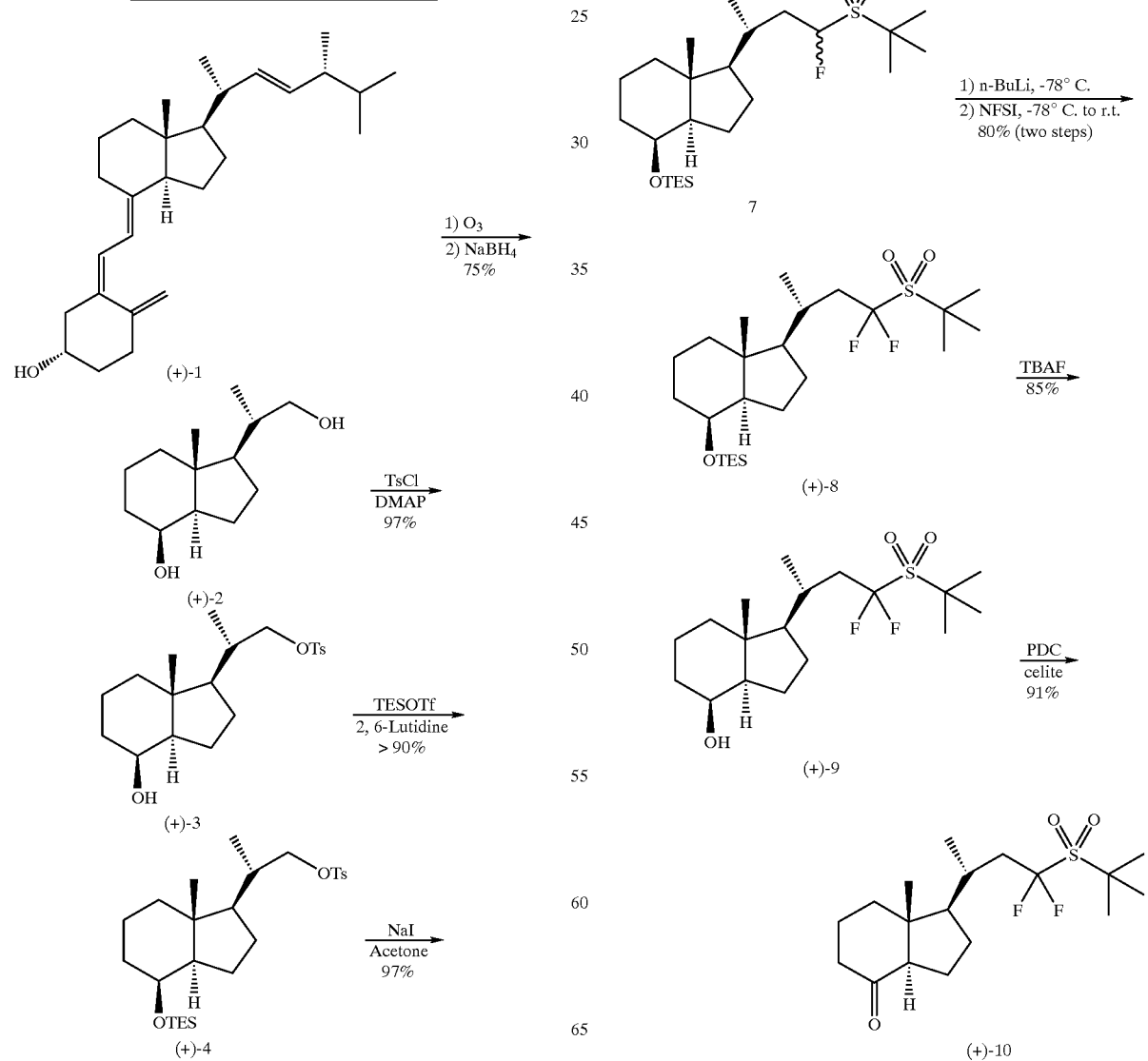

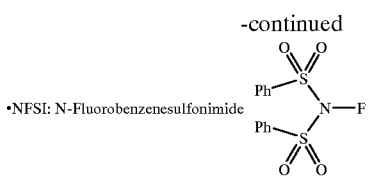
•NFSI: N-Fluorobenzenesulfonimide

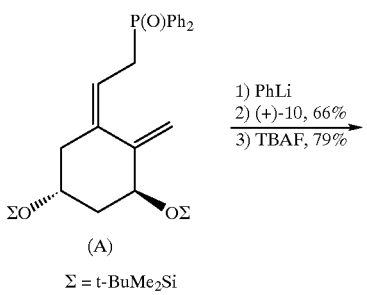

Formula II

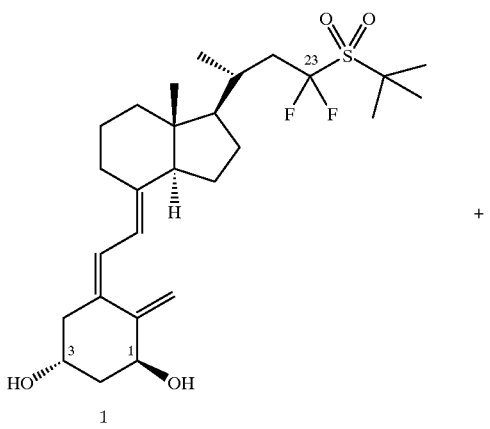

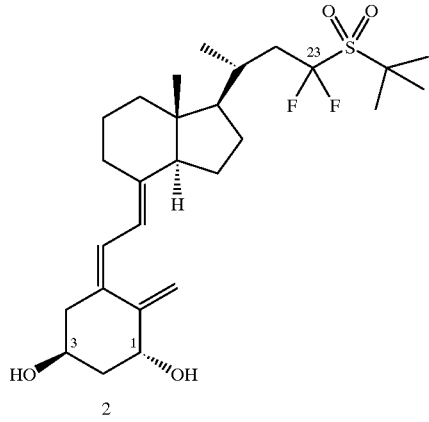

Synthesis of the iodide derivative 5 of the C,D-ring is carried out from the calcitriol starting material 1 through intermediates 2, 3, and 4 in conventional manner. These steps in the synthesis are described in greater detail in our publication, Journal of Organic Chemistry, 1997, Vol. 62, pp. 3299–3314.

Preparation of the various intermediates 6, 7, 8, 9, and 10 and the Formula II compounds is described in Examples 1 through 5 hereinafter.

EXAMPLE 1

TES protected C,D-ring Sulfone (+)-6

A solution of methyl tert-butyl sulfone (594 mg, 4.40 mmol) and 20 ml of THF was cooled to −78° C., and then 3.1 mL (4.40 mmol, 1.4 M solution in hexane) of n-BuLi was added dropwise to the solution. After 15 minutes, 1.3 mL of HMPA was added and the solution was stirred for another 15 minutes. A precooled (−78° C.) solution of iodide 5 (381 mg, 0.87 mmol) in 20 mL of THF was added slowly via cannula. The reaction mixture was then warmed up to room temperature. The reaction was quenched with water, extracted with EtOAc, washed with brine, dried over anhydrous $MgSO_4$, concentrated in vacuo, and then purified by column chromatography (25% EtOAc/hexanes) to give 336 mg (87%) of the desired sulfone (+)-6 as a colorless oil: $[\alpha]^{25}_D$+45.9° (c 3.3, $CHCl_3$); $^1H$ NMR (400 MHz, $CDCl_3$) δ4.02 (d, J=1.6 Hz, 1H), 3.01–2.90 (m, 1H), 2.85–2.73 (m, 1H), 2.07–1.75 (m, 4H), 1.71–1.50 (m, 4H), 1.41 (s, 9H), 1.40–1.18 (m, 5H), 1.16–1.00 (m, 2H), 0.96–0.89 (m, 15H), 0.54 (q, J=8.0 Hz, 6H); $^{13}C$ NMR (100 MHz, $CDCl_3$) δ69.46, 59.15 56.56, 53.20, 43.30, 42.44, 40.92, 34.99, 34.76, 27.41, 26.33, 23.76, 23.12, 18.56, 17.85, 13.74, 7.14, 5.12; IR (neat, $cm^{-1}$) 2943, 2872, 1461, 1302, 1284, 1114, 1014; HRMS m/z ($M^+$) calcd 444.3093 for $C_{24}H_{48}O_3SSi$, found 480.3098.

EXAMPLE 2

Difluorinated C,D-ring Sulfone (+)-8

To a solution of the TES protected C,D-ring sulfone (+)-6 (265 mg, 0.60 mmol) in THF (6.0 mL) was added 0.85 mL of n-BuLi (1.4 M solution in hexane, 1.19 mmol) at −78° C. After being stirred for 30 minutes, a precooled solution of NFSI (N-fluorobenzenesulfonimide, bought directly from Aldrich, 226 mg, 0.72 mmol) in 5.0 mL of THF was added slowly to the reaction mixture, and then it was warmed up to room temperature. The reaction was quenched with water and extracted with EtOAc. The combined organic portions were washed with brine, dried, concentrated in vacuo, and then purified by column chromatography (25% EtOAc/hexanes) to give a mixture of mono and di-fluorinated sulfones.

The mixture (280 mg) was dissolved in 6.0 mL of THF and the solution was cooled to −78° C. To the solution was added 1.1 mL of n-BuLi (1.4 M solution in hexane, 1.54 mmol) and the reaction mixture was stirred for 30 minutes. A precooled solution of NFSI (386 mg, 1.22 mmol) in 5.0 mL of THF was then added slowly via cannula. The reaction mixture was warmed up to room temperature, quenched with water, extracted with EtOAc, washed with brine and concentrated. Purification by column chromatography (25% EtOAc/hexanes) gave 230 mg (80%) of the desired difluoronated C,D-ring sulfone (+)-8 as a colorless oil: $[\alpha]^{25}_D$+ 40.7° (c 2.1, $CHCl_3$); $^1H$ NMR (400 MHz, $CDCl_3$) δ4.02 (d, J=2.8 Hz, 1H), 2.45 (ddd, J=35.6, 13.6, 8.8 Hz, 1H), 2.05–1.75 (m, 5H), 1.70–1.54 (m, 3H), 1.52 (s, 9H), 1.44–1.13 (m, 6H), 1.08 (d, J=6.0 Hz, 3H), 0.95 (s, 3H), 0.94 (t, J=8.0 Hz, 9H), 0.55 (q, J=8.0 Hz, 6H); $^{13}C$ NMR (100 MHz, $CDCl_3$) δ130.37 (t, J=289.3 Hz), 69.49, 63.29, 56.97, 53.32, 42.58, 40.89, 35.21 (t, J=18.3 Hz), 34.72, 30.76, 27.75, 24.48, 23.09, 20.55, 17.83, 13.56, 7.17, 5.14; $^{19}F$ NMR (376 MHz, $CDCl_3$, $CFCl_3$ as internal) δ−94.82 (dd, J=218.1, 35.0 Hz), −97.41 (dd, J=218.3, 30.6 Hz); IR (neat, $cm^{-1}$) 2950, 2876, 1459, 1322, 1165, 1134, 1083, 1018; HRMS m/z ($M^+$) calcd 480.2905 for $C_{24}H_{46}F_2O_3SiS$, found 480.2900.

EXAMPLE 3

Deprotected Difluoronated C,D-ring Alcohol (+)-9

A solution of silyl ether (+)-8 (226 mg, 0.47 mmol) in THF (5.0 mL) and 1.2 mL of 1.0 M solution of tetra-n- butylammonium fluoride (TBAF) in THF was stirred overnight at room temperature. The mixture was quenched with water and extracted with EtOAc. The combined organic portions were washed with brine, dried, concentrated in vacuo and then purified by column chromatography (25% EtOAc/hexanes) to give 147 mg (85%) of the desired alcohol as a white solid: mp 105–106° C.; $[\alpha]^{25}_D$+34.7° (c 1.7, CHCl$_3$); $^1$H NMR (400 MHz, CDCl$_3$) δ4.07 (d, J=2.4 Hz, 1H), 2.45 (ddd, J=35.4, 13.6, 9.2 Hz, 1H), 2.05–1.74 (m, 6H), 1.64–1.12 (m, 18H), 1.09 (d, J=6.0 Hz, 3H), 0.97 (s, 3H); $^{13}$C NMR (100 MHz, CDCl$_3$) δ130.27 (t, J=289.3 Hz), 69.42, 63.32, 56.77, 52.82, 42.29, 40.51, 35.16 (t, J=18.5 Hz), 33.68, 30.76, 27.63, 24.47, 22.61, 20.44 (d, J=2.8 Hz), 17.57, 13.53; $^{19}$F NMR (376 MHz, CDCl$_3$, CFCl$_3$ as internal) δ–94.82 (dd, J=218.1, 35.0 Hz), –97.43 (dd, J=218.1, 32.0 Hz); IR (neat, cm$^{-1}$) 3564, 2939, 2869, 1317, 1133; HRMS m/z (M$^+$) calcd 366.2040 for C$_{18}$H$_{32}$F$_2$O$_3$S, found 366.2047; Anal. Calcd for C$_{18}$H$_{32}$F$_2$O$_3$S: C, 58.98; H, 8.74. Found: C, 58.45; H, 8.76.

EXAMPLE 4

C,D-ring Ketone (+)-10

To a solution of the C,D-ring alcohol (+)-9 (74 mg, 0.20 mmol) in CH$_2$Cl$_2$ (5.0 mL) were added 150 mg of oven-dried celite and pyridinium dichromate (PDC, 152 mg, 0.40 mmol) at room temperature. The reaction mixture was stirred overnight and then passed through a 2 cm pad of flash silica gel and washed with EtOAc. The filtrate was concentrated and purified by column chromatography (25% EtOAc/hexanes) to give 67 mg (91%) of the desired C,D-ring ketone (+)-10 as a colorless solid: mp 106–107° C.; $[\alpha]^{25}_D$+15.7° (c 3.5, CHCl$_3$); $^1$H NMR (400 MHz, CDCl$_3$) δ2.51–2.33 (m, 2H), 2.30–2.14 (m, 2H), 2.12–2.04 (m, 1H), 2.04–1.80 (m, 5H), 1.72 (m, 1H), 1.64–1.42 (m, 12H), 1.33 (m, 1H), 1.12 (d, J=6.0 Hz, 3H), 0.65 (s, 3H); $^{13}$C NMR (100 MHz, CDCl$_3$) δ211.56, 129.93 (t, J=289.4 Hz), 63.31, 61.99, 56.63, 49.90, 40.98, 38.95, 35.20 (t, J=18.5 Hz), 30.79, 27.75, 24.35, 24.02, 20.54 (d, J=2.6 Hz), 19.14, 12.49; $^{19}$F NMR (376 MHz, CDCl$_3$, CFCl$_3$ as internal) δ–94.87 (ddd, J=219.0, 33.6, 5.6 Hz), –97.46 (ddd, J=219.0, 30.5, 8.5 Hz); IR (neat, cm$^{-1}$) 3013, 1708, 1314, 1208; HRMS m/z (M$^+$) calcd 364.1884 for C$_{18}$H$_{30}$F$_2$O$_3$S, found 364.1884; Anal. Calcd for C$_{18}$H$_{30}$F$_2$O$_3$S: C, 59.31; H, 8.24. Found: C, 59.42; H, 8.27.

EXAMPLE 5

Analogs Formula II

A solution of 102 mg (0.18 mmol) of racemic phosphine oxide (A-ring) in 2.0 mL of anhydrous THF was cooled to –78° C. and treated with 94 µL (0.15 mmol, 1.6 M solution in THF) of phenyllithium under argon atmosphere. The mixture turned reddish orange and was stirred for 30 min at –78° C. To the solution was added dropwise a solution of 45 mg (0.12 mmol) of the C,D-ring ketone (+)-10 (dried azeotropically three times with benzene and held under vacuum for at least 24 h prior to use) in 1.0 mL of anhydrous THF. The reaction kept going on at –78° C. until the reddish orange color faded to yellow (about 4 hours). The reaction was quenched by adding 3.0 mL of a 1:1 mixture of 2 N sodium potassium tartrate and 2 N K$_2$CO$_3$ solution. The reaction mixture was extracted with EtOAc, washed with brine, dried over anhydrous MgSO$_4$, concentrated in vacuo, and then purified by column chromatography (97% hexanes/ ether) to afford 59 mg (66%) of the coupled product as a colorless oil.

The coupled product (59 mg, 0.081 mmol) was dissolved in 3.0 mL of anhydrous THF, and to this solution were added TBAF (0.32 mL, 0.32 mmol, 1.0 M solution in THF) and 46 µL (0.32 mmol, 4 equiv) of Et$_3$N. The reaction was run in darkness overnight, then quenched with water and extracted with EtOAc. The organic portions were washed with brine, dried over anhydrous MgSO$_4$, concentrated in vacuo and then purified by silica gel chromatography (90% EtOAc/ hexanes) to give 32 mg (79%) of a mixture of two diastereomers as a white solid. One portion (6 mg) of the diastereomers was separated by reverse phase HPLC (C-18 semipreparative column, 52% MeCN/H$_2$O, 3.0 mL/min) to afford 5.7 mg (19%) of Formula II-1 (1α, 3β, $t_R$ 100.8 min) as a foaming solid and 4.1 mg (14%) of Formula II-2 (1β, 3α, $t_R$ 95.8 min) as a colorless oil. Formula II-1: $[\alpha]^{25}_D$+17.4° (c 0.6, CHCl$_3$); $^1$H NMR (400 MHz, CDCl$_3$) δ6.37 (d, J=11.2 Hz, 1H), 6.01 (d,J=11.6 Hz, 1H), 5.33 (s, 1H), 4.99 (s, 1H), 4.44 (m, 1H), 4.23 (m, 1H), 2.83 (dd, J=12.4, 3.6 Hz, 1H), 2.66–2.38 (m, 2H), 2.31 (dd, J=13.4, 6.6 Hz, 1H), 2.10–1.20 (m, 24H), 1.12 (d, J=6.0 Hz, 3H), 0.59 (s, 3H); $^{13}$C NMR (100 MHz, CDCl$_3$) δ147.78, 142.73, 133.42, 130.24 (t, J=288.0 Hz), 125.04, 117.56, 112.10, 71.03, 67.06, 63.36, 56.70, 56.55, 46.17, 45.46, 43.02, 40.57, 35.13, 31.43, 29.17, 27.96, 24.48, 23.67, 22.40, 20.76, 12.09; $^{19}$F NMR (376 MHz, CDCl$_3$, CFCl$_3$ as internal) δ–94.87 (dd, J=217.7, 37.2 Hz), –97.39 (dd, J=219.0, 28.0 Hz); UV (EtOH) λ$_{max}$ 263 nm (ε 12,225); IR (neat, cm$^{-1}$) 3695, 3601, 2931, 2872, 1596, 1467, 1308, 1132, 1043; HRMS m/z (M$^+$) calcd 500.2772 for C$_{27}$H$_{42}$F$_2$O$_4$S, found 500.2774. Formula II-2: $[\alpha]^{25}_D$+8.50° (c 0.4, CHCl$_3$); $^1$H NMR (400 MHz, CDCl$_3$) δ6.38 (d, J=11.2 Hz, 1H), 6.01 (d, J=11.2 Hz, 1H), 5.32 (s, 1H), 5.00 (s, 1H) 4.45 (m, 1H), 4.22 (m, 1H), 2.83 (dd, J=12.8, 4.4 Hz, 1H), 2.62 (dd, J=12.8, 4.7 Hz, 1H), 2.46 (m, 1H), 2.29 (dd, J=13.4, 7.4 Hz, 1H), 2.20–1.20 (m, 24H), 1.12 (d, J=6.0 Hz, 3H), 0.59 (s, 3H); $^{13}$C NMR (100 MHz, CDCl$_3$) δ147.41, 142.76, 133.29, 130.24 (t, J=289.3 Hz), 125.05, 117.55, 112.91, 71.58, 67.00, 63.36, 56.70, 56.52 46.17, 45.69, 42.97, 40.55, 35.32 (t, J=17.8 Hz), 31.43, 29.14, 27.94, 24.47, 23.65, 22.42, 20.74, 12.09; $^{19}$F NMR (376 MHz, CDCl$_3$, CFCl$_3$ as internal) –94.81 (dd, J=220.7, 29.7 Hz), –97.38 (dd, J=215.8, 26.7 Hz); UV (EtOH) λ$_{max}$ 263 nm (ε 12,200); IR (neat, cm$^{-1}$) 3695, 3613, 2919, 1596, 1308, 1126, 1043. HRMS m/z (M$^+$) calcd 500.2772 for C$_{27}$H$_{42}$F$_2$O$_4$S, found 500.2784.

Preparation of the Formula III materials is set forth in Scheme 2 as follows:

Scheme 2
Synthesis of Formula III Calcitriol Analogs

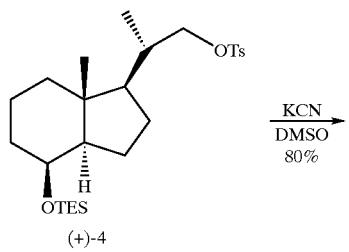

(+)-4

17

-continued

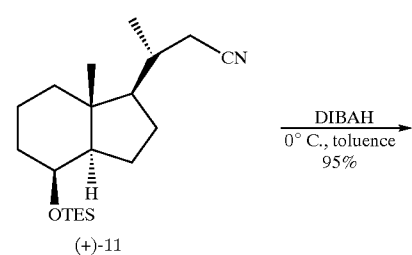
(+)-11

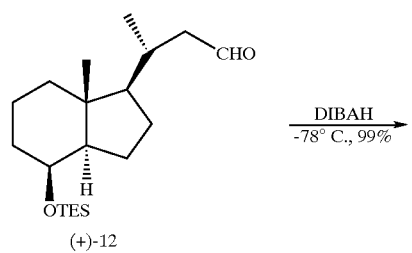
(+)-12

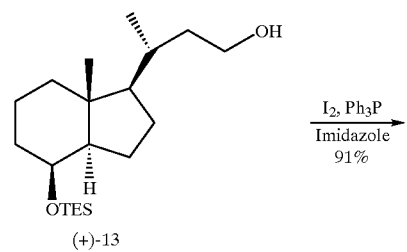
(+)-13

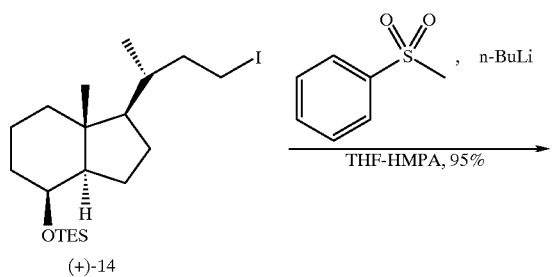
(+)-14

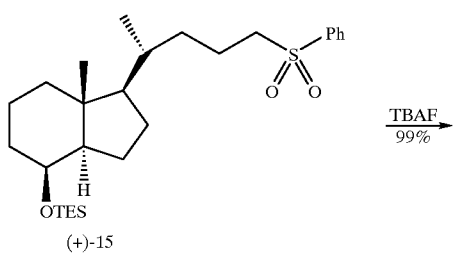
(+)-15

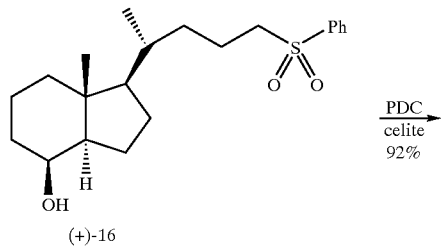
(+)-16

18

-continued

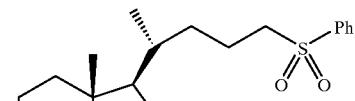
(+)-17

Formula III

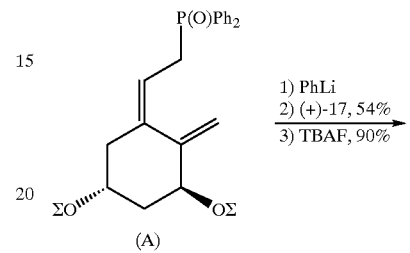
(A)

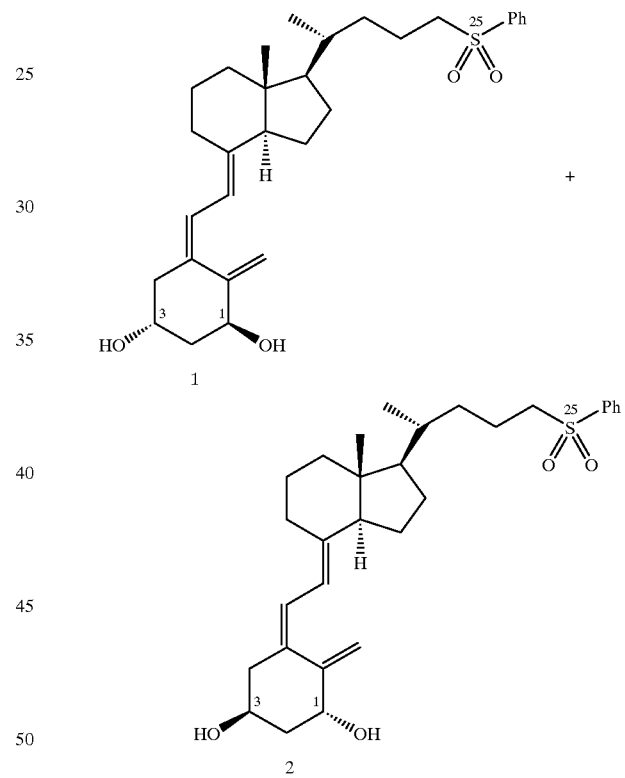

Synthesis of the iodide derivative 14 of the C,D-ring is carried out from the sulfonate starting material 4 and proceeds through intermediates 11, 12, and 13 as set forth in Scheme 2. These steps in the synthesis are described in greater detail in the following experimental sections.

Preparation of the various intermediates 15, 16, and 17 and the Formula III compounds is described in Examples 6 through 9 hereinafter.

EXAMPLE 6

TES Protected 25-phenyl C,D-ring Sulfone (+)-15

To a solution of methyl phenyl sulfone (181 mg, 1.16 mmol) and THF (10 mL) was added 0.83 mL (1.16 mmol)

of a 1.4 M solution of n-BuLi in hexane at −78° C. After 15 minutes, 0.3 mL of HMPA was added and the solution was stirred for another 15 minutes at −78° C. A precooled (−78° C.) solution of iodide 14 (105 mg, 0.23 mmol) in 3.0 mL of THF was added slowly via cannula. The reaction mixture was then warmed up to room temperature. The reaction was quenched with water, extracted with EtOAc, washed with brine, dried over anhydrous $MgSO_4$, and concentrated to give a crude product that was purified by column chromatography (25% EtOAc/hexanes) to give 105 mg (95%) of the desired sulfone (+)-15 as a colorless oil: $[\alpha]^{25}_D$+44.10° (c 1.3, $CHCl_3$); $^1H$ NMR (400 MHz, $CDCl_3$) δ7.94–7.86 (m, 2H), 7.70–7.52 (m, 3H), 4.00 (d, J=2.4 Hz, 1H), 3.03 (m, 2H), 1.93–1.46 (m, 7H), 1.44–1.22 (m, 5H), 1.22–0.96 (m, 5H), 0.92 (t, J=8.0 Hz, 9H), 0.85 (s, 3H), 0.83 (d, J=6.4 Hz, 3H), 0.53 (q, J=7.9 Hz, 6H); $^{13}C$ NMR (100 MHz, $CDCl_3$) δ139.43, 133.74, 129.39, 128.15, 69.45, 56.88, 56.51, 53.14, 42.27, 40.85, 35.10, 34.72, 34.54, 27.43, 23.07, 19.45, 18.47, 17.79, 13.64, 7.10, 5.07; IR (neat, $cm^{-1}$) 2949, 2875, 1447, 1307, 1149, 1087, 1025; HRMS m/z (M$^+$) calcd 478.2937 for $C_{27}H_{46}O_3SiS$, found 478.2932.

EXAMPLE 7

Deprotected 25-phenyl C,D-ring Sulfone (+)-16

A flame-dried 5 mL flask was charged with 105 mg (0.22 mmol) of the silyl ether (+)-15, 2.0 mL of anhydrous THF and 0.55 mL (0.55 mmol) of a 1.0 M solution of TBAF in THF. The resulting reaction mixture was stirred overnight at room temperature, and then it was quenched with water and extracted with EtOAc. The combined organic portions were washed with brine, dried, concentrated in vacuo and then purified by chromatography (20% EtOAc/hexanes) to give 79.mg (99%) of the desired alcohol (+)-16 as a colorless oil: $[\alpha]^{25}_D$+31.80° (c 3.0, $CHCl_3$); $^1H$ NMR(400 MHz, $CDCl_3$) δ7.92–7.84 (m, 2H), 7.63 (t, J=7.4 Hz, 1H), 7.58–7.50 (m, 2H), 4.02 (d, J=2.4 Hz, 1H), 3.02 (m, 2H), 1.92 (d, J=13.2 Hz, 1H), 1.85–1.67 (m, 4H), 1.62–0.94 (m, 12H), 0.86 (s, 3H), 0.82 (d, J=6.8 Hz, 3H); $^{13}C$ NMR (100 MHz, $CDCl_3$) δ139.32, 133.75, 129.38, 128.10, 69.27, 56.78, 56.31, 52.62, 41.95, 40.42, 35.05, 34.42, 33.65, 27.25, 22.55, 19.39, 18.35, 17.51,13.61; IR (neat, $cm^{-1}$) 3539, 2937, 2872, 1446, 1305,1147,1086; HRMS m/z (M$^+$) calcd 364.2072 for $C_{21}H_{32}O_3S$, found 364.2069.

EXAMPLE 8

C,D-ring Ketone (+)-17

To a solution of the C,D-ring alcohol (+)-16 (68 mg, 0.19 mmol) in $CH_2Cl_2$ (5.0 mL) were added 140 mg of oven-dried celite and pyridinium dichromate (PDC, 140 mg, 0.38 mmol) at room temperature. The reaction mixture was stirred overnight and then passed through a 2 cm pad of flash silica gel and washed with EtOAc. The filtrate was concentrated and purified by silica gel chromatography (50% EtOAc/hexanes) to give 62 mg (92%) of the desired C,D-ring ketone (+)-17 as a colorless oil: $[\alpha]^{25}_D$+10.8° (c 3.4, $CHCl_3$); $^1H$ NMR (400 MHz, $CDCl_3$) δ7.94–7.82 (m, 2H), 7.63 (t, J=7.4 Hz, 1H), 7.58–7.48 (m, 2H), 3.02 (m, 2H), 2.39 (dd, J=11.6, 7.2 Hz, 1H), 2.30–2.10 (m, 2H), 2.10–1.26 (m, 12H), 1.26–1.02 (m, 2H), 0.89 (d, J=6.4 Hz, 3H), 0.57 (s, 3H); $^{13}C$ NMR (100 MHz, $CDCl_3$) δ211.97, 139.34, 133.80, 129.41, 128.07, 61.91, 56.67, 56.28, 49.93, 41.01, 38.96, 35.30, 34.41, 27.56, 24.10, 19.33, 19.11, 18.53, 12.56; IR (neat, $cm^{31\ 1}$) 2943, 2872, 1708, 1443, 1378, 1302, 1143, 1079; HRMS m/z (M$^+$) calcd 362.1916 for $C_{21}H_{30}O_3S$, found 362.1910.

EXAMPLE 9

Analogs Formula III

Racemic phosphine oxide (A-ring, 102 mg, 0.18 mmol) was dissolved in 2.0 mL of anhydrous THF and cooled to −78° C. under argon atmosphere. To this solution was added 94 μL (0.15 mmol) of phenyllithium (1.8 M solution in THF) dropwise. The mixture turned deep reddish orange and persisted. After stirring at −78° C. for 30 minutes, a precooled (−78° C.) solution of C,D-ring ketone (+)-1 7 (44 mg, 0.12 mmol) dissolved in 1.0 mL of anhydrous THF was added dropwise via cannula. The reaction kept going on until the reddish orange color faded to yellow (about 4 hours). The reaction was quenched by adding 3.0 mL of a 1:1 mixture of 2 N sodium potassium tartrate and 2 N $K_2CO_3$ solution. The reaction mixture was allowed to warm to room temperature, extracted with EtOAc, washed with brine, dried over anhydrous $MgSO_4$, filtered, concentrated in vacuo, and then purified by column chromatography (20% EtOAc/hexanes) to afford 47 mg (54%) of the coupled product as a colorless oil.

The coupled product (47 mg, 0.065 mmol) was dissolved in 3.0 mL of anhydrous THF with 38 μL of $Et_3N$, and to this solution was added 0.26 mL (0.26 mmol) of TBAF (1.0 M solution in THF) at room temperature. The reaction was run in darkness overnight, then extracted with EtOAc, washed with brine, dried over anhydrous $MgSO_4$, concentrated in vacuo and then purified by column chromatography (90% EtOAc/Hexanes) to give 29 mg (90%) of a mixture of two diastereomers as a colorless oil. One portion (20 mg) of the diastereomers was separated by reverse phase HPLC (C-18 semipreparative column, 51% $MeCN/H_2O$, 3.0 mL/min) to afford 9.1 mg (22%) of Formula III-1 (1α, 3β, $t_R$ 66.4 min) and 2.6 mg (6%) of Formula III-2 (1β, 3α, $t_R$ 63.7 min) as colorless oils. Formula III-1: $[\alpha]^{25}_D$+23.0° (c 1.0, $CHCl_3$); $^1H$ NMR (400 MHz, $CDCl_3$) δ7.96–7.88(m, 2H), 7.66 (t, J=7.4 Hz, 1H), 7.62–7.54 (m, 2H), 6.36 (d, J=11.2 Hz, 1H), 6.00 (d, J=11.2 Hz, 1H), 5.32 (s, 1H), 4.99 (s, 1H), 4.42 (m, 1H), 4.22 (m, 1H), 3.04 (m, 2H), 2.81 (dd, J=12.0, 3.6 Hz, 1H), 2.59 (dd, J=13.2, 3.2 Hz, 1H), 2.31 (dd, J=13.4, 6.6 Hz, 1H), 2.08–1.04 (m, 18H), 0.88 (d, J=6.4 Hz, 3H), 0.51 (s, 3H); $^{13}C$ NMR (100 MHz, $CDCl_3$) δ147.80, 143.11, 139.48, 133.84, 133.20, 129.48, 128.23, 125.13, 117.32, 112.02, 71.03, 67.05, 56.92, 56.44, 56.33, 46.07, 45.45, 43.04, 40.60, 36.02, 34.70, 29.22, 27.81, 23.73, 22.41, 19.55, 18.74,12.19; UV (EtOH) $\lambda_{max}$ 264 nm (ϵ 15,100); IR (neat $cm^{-1}$) 3683, 3601, 2931, 2861, 1596, 1443, 1378, 1302, 1149, 1079, 1043; HRMS m/z (M$^+$) calcd 498.2804 for $C_{30}H_{42}O_4S$, found 498.2818. Formula III-2: $[\alpha]^{25}_D$−2.7° (c 0.3, $CHCl_3$); $^1H$ NMR (400 MHz, $CDCl_3$) δ7.98–7.88 (m, 2H), 7.66 (t, J=7.6 Hz, 1H), 7.62–7.54 (m, 2H), 6.38 (d, J=11.6 Hz, 1H), 5.99 (d, J=11.6 Hz, 1H), 5.31 (s, 1H), 4.99 (s, 1H), 4.44 (m, 1H), 4.21 (m, 1H), 3.05 (m, 2H), 2.82 (d, J=13.2 Hz, 1H), 2.61 (dd, J=13.2, 3.6 Hz, 1H), 2.29 (dd, J=13.0, 7.4 Hz, 1H), 2.20–1.06 (m, 18H), 0.89 (d, J=6.8 Hz, 3H), 0.51 (s, 3H); $^{13}C$ NMR (100 MHz, $CDCl_3$) δ147.48, 143.16, 139.49, 133.85, 133.09, 129.49, 128.24, 125.14, 117.33, 112.76, 71.55, 67.02, 56.92, 56.44, 56.33, 46.08, 45.67, 43.02, 40.59, 36.02, 34.71, 29.20, 27.81, 23.71, 22.44, 19.56, 18.75, 12:19; UV (EtOH) $\lambda_{max}$ 263 nm (ϵ 13,600); IR (neat, $cm^{-1}$) 3695, 3613, 2966, 1596, 1449, 1384, 1249, 1043; HRMS m/z (M$^+$) calcd 498.2804 for $C_{30}H_{42}O_4S$, found 498.2814.

Preparation of the Formula IV materials is set forth in Scheme 3 as follows:

Scheme 3
Synthesis of Formula IV Calcitriol Analogs
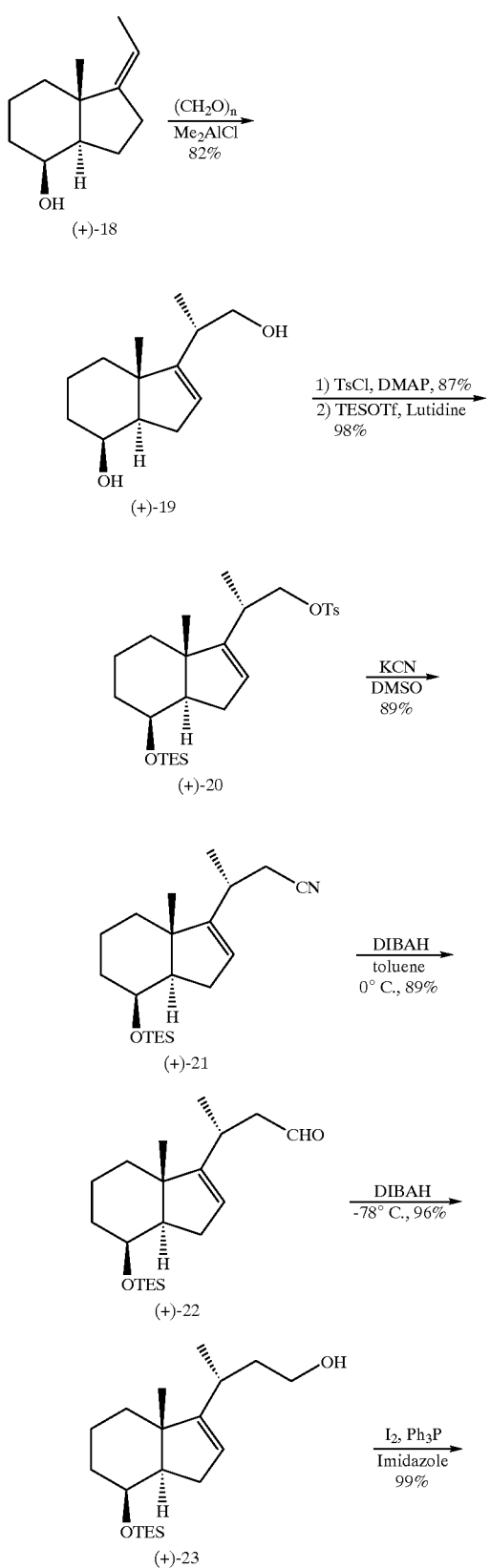
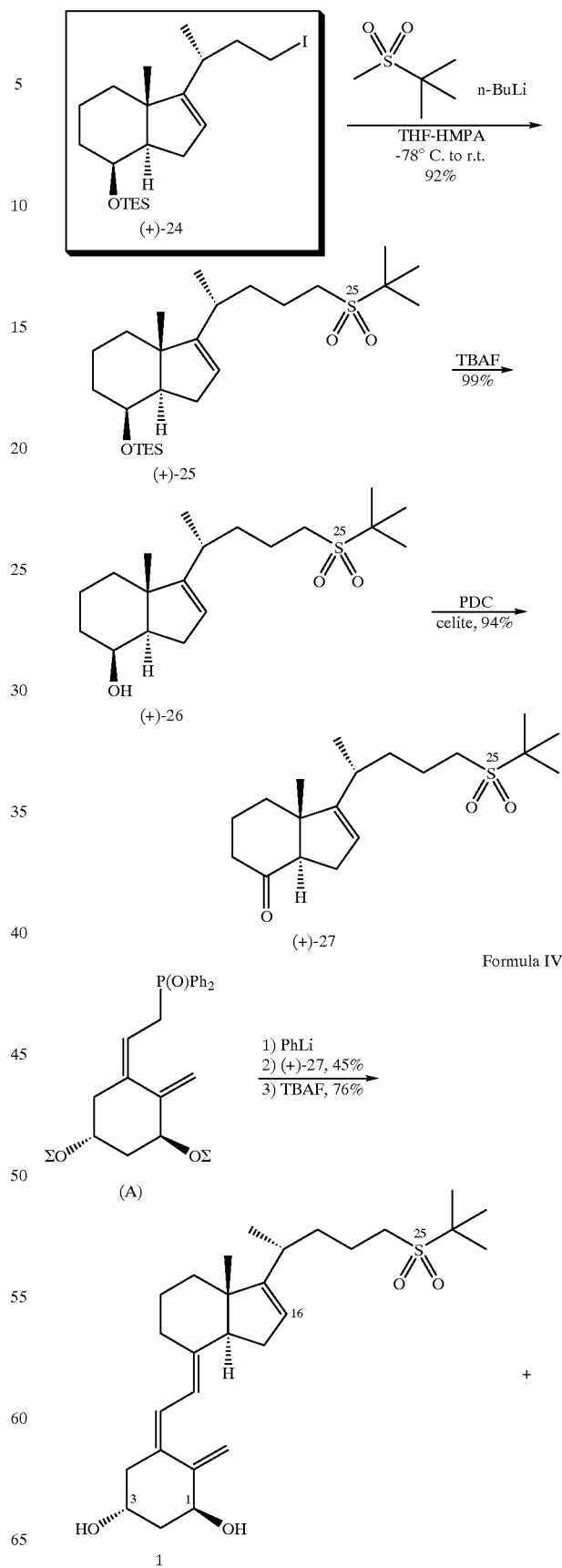

-continued

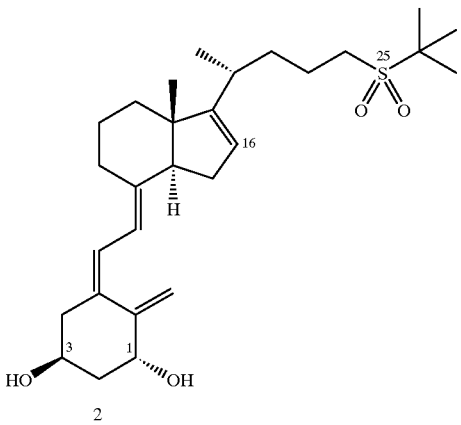

Synthesis of the iodide derivative 24 of the C,D-ring is carried out from the 17-ene starting material 18 and proceeds through intermediates 19, 20, 21, 22, and 23 as set forth in Scheme 3. These steps in the synthesis are described in greater detail in J. Med. Chem. 1999, Vol. 41, pp. 3008–3014.

Preparation of the various intermediates 25, 26, and 27 and the Formula IV compounds are described in Examples 10 through 13 hereinafter.

EXAMPLE 10

TES Protected C,D-ring Sulfone (+)-25

A solution of methyl t-butyl sulfone (118 mg, 0.87 mmol) and THF (3.0 mL) was cooled to −78° C. and treated dropwise under argon with 0.61 mL (0.85 mmol) of a 1.4 M solution of n-BuLi in hexane. The solution was stirred for 15 minutes at −78° C. To the solution was added 0.3 mL of HMPA and then the solution was stirred for another 15 minutes. A precooled (−78° C.) solution of iodide 24 (78 mg, 0.17 mmol) in 2.0 mL of THF was added slowly via cannula. The reaction mixture was then warmed up to room temperature. The reaction was quenched with water, extracted with EtOAc, washed with brine, dried over anhydrous $MgSO_4$, concentrated in vacuo, and then purified by column chromatography (20% EtOAc/hexanes) to give 73 mg (92%) of the desired sulfone (+)-25 as a colorless oil: $[\alpha]^{25}_D$+18.5° (c 7.3, $CHCl_3$); $^1H$ NMR (400 MHz, $CDCl_3$) δ5.26 (s, 1H), 4.10 (d, J=2.0 Hz, 1H), 2.87 (t, J=7.8 Hz, 2H), 2.24 (t, J=13.2 Hz, 1H), 2.07 (m, 1H), 1.94–1.76 (m, 4H), 1.72–1.56 (m, 4H), 1.55–1.28 (m, 13H), 0.99 (s, J=5.2 Hz, 3H), 0.93 (t, J=7.8 Hz, 9H), 0.54 (q, J=7.9 Hz, 6H); $^{13}C$ NMR (100 MHz $CDCl_3$) δ159.41, 120.15, 68.85, 58.73, 54.99, 46.61, 45.68, 35.71, 35.64, 34.83, 31.55, 30.68, 23.39, 22.16, 18.87, 18.77, 17.98, 6.88, 4.84; IR (neat, $cm^{-1}$) 2943, 2872, 1455, 1284, 1108, 1079, 1026; HRMS m/z ($M^+$) calcd 456.3093 for $C_{25}H_{48}O_3SSi$, found 456.3090.

EXAMPLE 11

Deprotected C,D-ring Sulfone (+)-26

To a solution of silyl ether (+)-25 (83 mg, 0.18 mmol) in THF (3.0 mL) was added 0.45 mL (0.45 mmol) of a 1.0 M solution of TBAF in THF, and then it was stirred overnight at room temperature. The reaction mixture was quenched with water and extracted with EtOAc. The combined organic portions were washed with brine, dried, concentrated in vacuo and then purified by chromatography (20% EtOAc/ hexanes) to give 61 mg (99%) of the desired alcohol (+)-26 as a colorless oil: $[\alpha]^{25}_D$+4.2° (c 1.5, $CHCl_3$); $^1H$ NMR (400 MHz, $CDCl_3$) δ5.30 (d, J=1.2 Hz, 1H), 4.15 (s, 1H), 2.87 (t, J=8.0 Hz, 2H), 2.25 (t, J=13.4 Hz, 1H), 2.07 (m, 1H), 2.00–1.45 (m, 12H), 1.38 (s, 9H), 0.99 (d, J=6.8 Hz, 3H); $^{13}C$ NMR (100 MHz, $CDCl_3$) δ159.23, 120.26, 68.94, 58.75, 54.31, 46.28, 45.62, 35.56, 35.38, 33.75, 31.57, 30.15, 23.38, 22.06, 18.88, 18.37, 17.71; IR (neat, $cm^{-1}$) 3519, 2919, 1461, 1367, 1284, 1108; HRMS m/z ($M^+$) calcd 342.2229 for $C_{19}H_{34}O_3S$, found 342.2235.

EXAMPLE 12

C,D-ring Ketone (+)-27

To a solution of the C,D-ring alcohol (+)-26 (60 mg, 0.18 mmol) in $CH_2Cl_2$ (5.0 mL) were added 130 mg of oven-dried celite and pyridinium dichromate (PDC, 132 mg, 0.35 mmol) at room temperature. The reaction mixture was stirred overnight and then passed through a 2 cm pad of flash silica gel and washed with EtOAc. The filtrate was concentrated and purified by column chromatography (50% EtOAc/ hexanes) to give 56 mg (94/%) of the desired C,D-ring ketone (+)-27 as a colorless oil: $[\alpha]^{25}_D$+14.7° (c 5.2, $CHCl_3$); $^1H$ NMR (400 MHz, $CDCl_3$) δ5.27 (t, J=1.4 Hz, 1H), 2.86 (t, J=7.8 Hz, 2H), 2.81 (m, 1H), 2.40 (ddt, J=15.8, 10.6, 1.4 Hz, 1H), 2.29–2.19 (m, 2H), 2.17–1.90 (m, 4H), 1.90–1.58 (m, 5H), 1.56–1.40 (m, 1H), 1.36 (s, 9H), 1.04 (d, J=6.8 Hz, 3H), 0.77 (s, 3H); $^{13}C$ NMR (100 MHz, $CDCl_3$) δ210.72, 157.10, 120.67, 62.92, 58.73, 53.64, 45.37, 40.35, 35.40, 34.24, 32.64, 26.95, 23.86, 23.31, 21.47, 18.79, 17.24; IR (neat, $cm^{-1}$) 2954, 1713, 1455,1367, 1284, 1108; HRMS m/z ($M^+$) calcd 340.2072 for $C_{19}H_{32}O_3S$, found 340.2073.

EXAMPLE 13

Analogs Formula IV

A solution of 108 mg (0.19 mmol) of racemic phosphine oxide (A-ring) in 2.0 mL of anhydrous THF was cooled to −78° C. and treated with 107 μL (0.16 mmol, 1.5 M solution in THF) of phenyllithium under argon atmosphere. The mixture turned reddish orange and was stirred for 30 min at −78° C. To the solution was added dropwise a solution of 40 mg (0.12 mmol) of the C,D-ring ketone (+)-27 in 1.0 mL of anhydrous THF. The reaction kept going on until the reddish orange color faded to yellow (about 5 hours). The reaction was quenched by adding 3.0 mL of a 1:1 mixture of 2 N sodium potassium tartrate and 2 N $K_2CO_3$ solution. The reaction mixture was extracted with EtOAc, washed with brine, dried over anhydrous $MgSO_4$, concentrated in vacuo, and then purified by column chromatography (20% EtOAc/ hexanes) to afford 37 mg (45%) of the coupled product as a colorless oil.

The coupled product (37 mg, 0.053 mmol) was dissolved in 3.0 mL of anhydrous THF, and to this solution were added 0.21 mL (0.21 mmol) of a 1.0 M solution of TBAF in THF and 29 μL (0.21 mmol) of triethylamine. The reaction was run in darkness overnight, then extracted with EtOAc, washed with brine, dried over anhydrous $MgSO_4$, concentrated in vacuo and then purified by silica gel chromatography (90% EtOAc/hexanes) to give 19 mg (76%) of a mixture of two diastereomers as a colorless oil. The diastereomers were separated by reverse phase HPLC (C-18 semipreparative column, 49% $MeCN/H_2O$, 3.0 mL/min) to afford 6.3 mg (11%) of Formula IV-1 (1α, 3β, $t_R$ 47.9 min) and 4.1 mg (7%) of Formula IV-2 (1β, 3α, $t_R$ 43.2 min) as colorless oils. Formula IV-1: $[\alpha]^{25}_D$ +6.7° (c 0.6, EtOH); $^1$H NMR (400 MHz, CDCl$_3$) δ6.37 (d, J=11.2 Hz, 1H), 6.11 (d, J=10.4 Hz, 1H), 5.34 (s, 2H), 5.01 (s, 1H), 4.45 (m, 1H), 4.24 (m, 1H), 3.00–2.75 (m, 3H), 2.60 (d, J=12.8 Hz, 1H), 2.40–1.50 (m, 16H), 1.40 (s, 9H), 1.05 (d, J=6.8 Hz, 3H), 0.69 (s, 3H); $^{13}$C NMR (100 MHz, CDCl$_3$) δ158.85, 147.62, 142.31, 133.09, 124.83, 120.84, 116.91, 111.64, 70.63, 66.86, 58.81, 58.31, 50.04, 45.62, 45.14, 42.82, 35.53, 35.28, 32.65, 29.39, 28.74, 23.57, 23.46, 21.59, 18.73, 16.98; UV EtOH) $\lambda_{max}$ 263 nm (ε 12,000); IR (neat, cm$^{-1}$) 3425, 2919, 1284, 1108, 1049; HRMS m/z(M$^+$) calcd 476.2960 for C$_{28}$H$_{44}$O$_4$S, found 476.2952. Formula IV-2: $[\alpha]^{25}_D$ −8.9° (c 0.5, EtOH); $^1$H NMR (400 MHz, CDCl$_3$) δ6.39 (d, J=11.2 Hz, 1H), 6.09 (d, J=10.6 Hz, 1H), 5.32 (s, 2H), 5.01 (d, J=1.6 Hz, 1H), 4.45 (m, 1H), 4.22 (m, 1H), 2.94–2.76 (m, 3H), 2.62 (m, 1H), 2.42–1.46 (m, 16H), 1.41 (s, 9H), 1.05 (d, J=6.8 Hz, 3H), 0.68 (s, 3H); $^{13}$C NMR (100 MHz, CDCl$_3$) δ158.84, 147.02, 142.40, 132.88, 124.89, 120.83, 116.91, 113.00, 71.55, 66.74, 58.82, 58.30, 50.06, 45.63, 45.53, 42.73, 35.54, 35.26, 32:65, 29.43, 28.73, 23.56, 23.47, 21.61, 18.72, 16.99; UV EtOH) $\lambda_{max}$ 264 nm (ε 13,200); IR (neat, cm$^{-1}$) 3401, 2919, 1455, 1284, 1108, 1049; HRMS m/z (M$^+$) calcd 476.2960 for C$_{28}$H$_{44}$O$_4$S, found 476.2955.

Preparation of the Formula V materials is set forth in Scheme 4 as follows:

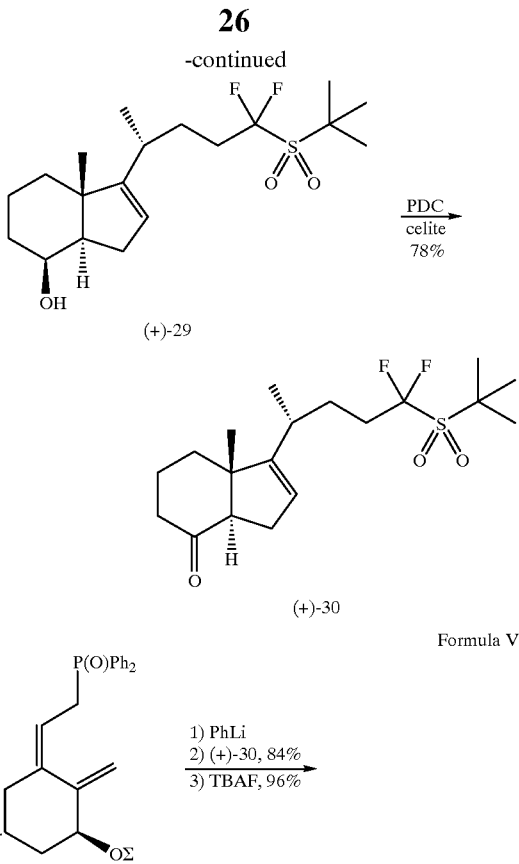

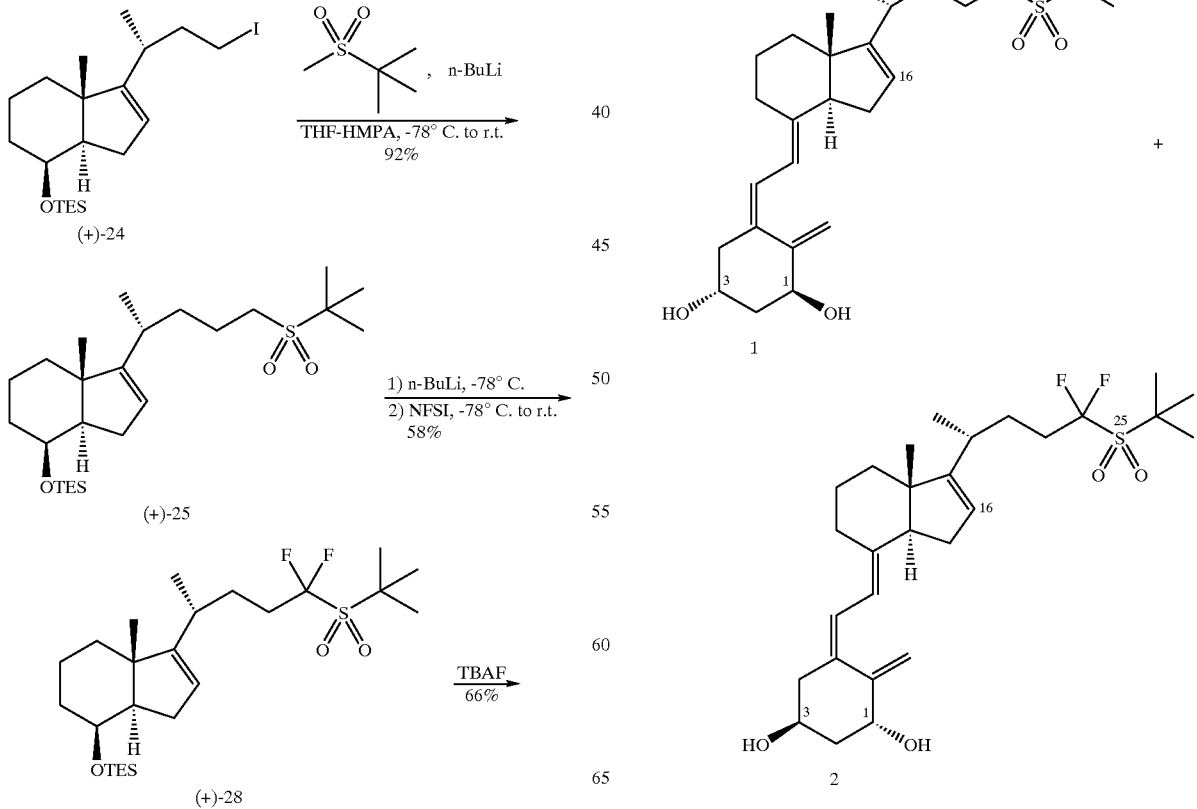

Scheme 4 begins with the same iodide derivative 24 and the next intermediate 25 as set forth in Scheme 3. Preparation of the various intermediates 28, 29, and 30 and the Formula V compounds is described in Examples 14 through 17 hereinafter.

EXAMPLE 14

Difluorinated C,D-ring Sulfone (+)-28

To a solution of the TES protected C,D-ring sulfone (+)-25 (56 mg, 0.12 mmol) in THF (3.0 ml) was added 0.18 mL (0.29 mmol) of a 1.6 M solution of n-BuLi in hexane at −78° C. After being stirred for 30 minutes, a precooled (−78° C.) solution of NFSI (N-fluorobenzenesulfonimide, 77 mg, 0.24 mmol) in 1.0 mL of THF was added slowly to the reaction mixture, and then it was warmed up to room temperature. The reaction was quenched with water and extracted with EtOAc. The combined organic portions were washed with brine, dried, and concentrated in vacuo. Purification by column chromatography (20% EtOAc/hexanes) gave a mixture of mono and di-fluorinated sulfones.

The mixture (58 mg) was dissolved in THF (3.0 ml) and the solution was cooled to −78° C. To the solution was added 0.18 mL of n-BuLi (1.6 M solution in hexane, 0.29 mmol) and the reaction mixture was stirred for 30 minutes at −78° C. A precooled (−78° C.) solution of NFSI (96 mg, 0.30 mmol) in 1.0 mL of THF was then added slowly via cannula. The reaction mixture was warmed up to room temperature, quenched with water, extracted with EtOAc, washed with brine and concentrated. Purification by column chromatography (20% EtOAc/hexanes) gave 35 mg (58%) of the desired difluoronated C,D-ring sulfone (+)-28 as a colorless oil: $[\alpha]^{25}_D$+16.7° (c 3.5, CHCl$_3$); $^1$H NMR (400 MHz, CDCl$_3$) δ5.30 (d, J=1.2 Hz, 1H), 4.11 (d, J=2.0 Hz, 1H), 2.45–2.02 (m, 4H), 1.94–1.58 (m, 9H), 1.56–1.20 (m, 10H), 1.02 (d, J=6.8 Hz, 3H), 1.00 (s, 3H), 0.95 (t, J=8.0 Hz, 9H), 0.56 (q, J=7.9 Hz, 6H); $^{13}$C NMR (100 MHz, CDCl$_3$) δ158.80, 129.63 (t, J=287.9 Hz), 120.94, 69.08, 63.30, 55.28, 46.81, 35.92, 35.10, 31.65, 30.99, 29.02 (t, J=19.3 Hz), 27.00, 24.36, 22.49, 18.91, 18.25, 7.17, 5.11; $^{19}$F NMR (376 MHz, CDCl$_3$, CFCl$_3$ as internal) δ−97.76 (t, J=16.9 Hz); IR (neat, cm$^{-1}$) 2955, 2933, 2876, 1458, 1324, 1136, 1082, 1029; HRMS m/z (M$^+$) calcd 492.2905 for C$_{25}$H$_{46}$F$_2$O$_3$SSi, found 492.2907.

EXAMPLE 15

Deprotected Difluoronated C,D-ring Alcohol (+)-29

A solution of silyl ether (+)-28 (89 mg, 0.18 mmol) in THF (2.0 mL) and 0.45 mL of 1.0 M solution of TBAF in THF was stirred overnight at room temperature. The mixture was quenched with water and extracted with EtOAc. The combined organic portions were washed with brine, dried, concentrated in vacuo and then purified by column chromatography (20% EtOAc/hexanes) to give 45 mg (66%) of the desired alcohol as a colorless oil: $[\alpha]^{25}_D$+3.4° (c 3.8, CHCl$_3$); $^1$H NMR (400 MHz, CDCl$_3$) δ5.34 (t, J=1.4 Hz, 1H), 4.16 (s, 1H), 2.34–1.36 (m, 23H), 1.03 (d, J=6.8 Hz, 3H), 1.02 (s, 3H); $^{13}$C NMR (100 MHz, CDCl$_3$) δ158.64, 129.52 (t, J=287.7 Hz), 121.04, 69.01, 63.29, 54.57, 46.47, 35.57, 33.96, 31.63, 30.42, 28.96 (t, J=19.8 Hz), 26.93, 24.32, 22.37, 18.50, 17.96; $^{19}$F NMR (376 MHz, CDCl$_3$, CFCl$_3$ as internal) δ−97.83 (m); IR (neat, cm$^{-1}$) 3568, 2930, 2870, 1458, 1320, 1134; HRMS m/z (M$^+$) calcd 378.2040 for C$_{19}$H$_{32}$F$_2$O$_3$S, found 378.2047.

EXAMPLE 16

C,D-ring Ketone (+)-30

A flame-dried 5 mL flask was charged with 40 mg (0.11 mmol) of the C,D-ring alcohol (+)-29, 3.0 mL of anhydrous THF, 100 mg of oven-dried celite and 100 mg (0.27 mmol) of PDC. The reaction mixture was stirred overnight at room temperature and then passed through a 2 cm pad of flash silica gel and washed with EtOAc. The filtrate was concentrated and purified by column chromatography (20% EtOAc/hexanes) to give 31 mg (78%) of the desired C,D-ring ketone (+)-30 as a colorless oil: $[\alpha]^{25}_D$+12.9° (c 3.4, CHCl$_3$); $^1$H NMR (400 MHz, CDCl$_3$) δ5.33 (d, J=1.2 Hz, 1H), 2.83 (dd, J=10.4, 6.4 Hz, 1H), 2.45 (dd, J=15.6, 10.8 Hz, 1H), 2.36–1.56 (m, 12H), 1.50(s, 9H), 1.09 (d, J=6.8 Hz, 3H), 0.80 (s, 3H); $^{13}$C NMR (100 MHz, CDCl$_3$) δ210.87, 156.51, 129.38 (t, J=287.8 Hz), 121.68, 63.36, 63.23, 53.83, 40.63, 34.50, 32.64, 28.85 (t, J=19.6 Hz), 27.31, 26.90, 24.31, 24.14, 21.70, 17.47; $^{19}$F NMR (376 MHz, CDCl$_3$, CFCl$_3$ as internal) δ−97.79 (m); IR (neat, cm$^{-1}$) 2939, 2873, 1718, 1458, 1377, 1320, 1130; HRMS m/z (M$^+$) calcd 376.1884 for C$_{19}$H$_{30}$F$_2$O$_3$S, found 376.1889.

EXAMPLE 17

Analogs Formula V

Racemic phosphine oxide (A-ring, 89 mg, 0.15 mmol) was dissolved in 2.0 mL of anhydrous THF and cooled to −78° C. under argon atmosphere. To this solution was added 100 μL (0.16 mmol) of phenyllithium (1.6 M solution in THF) dropwise. The mixture turned deep reddish orange and persisted. After stirring at −78° C. for 30 minutes, a precooled (−78° C.) solution of C,D-ring ketone (+)-30 (30 mg, 0.080 mmol) dissolved in 1.0 mL of anhydrous THF was added dropwise via cannula. The reaction kept going on until the reddish orange color faded to yellow (about 4 hours). The reaction was quenched by adding 3.0 mL of a 1:1 mixture of 2 N sodium potassium tartrate and 2 N K$_2$CO$_3$ solution. The reaction mixture was allowed to warm to room temperature, extracted with EtOAc, washed with brine, dried over anhydrous MgSO$_4$, filtered, concentrated in vacuo, and then purified by column chromatography (10% EtOAc/hexanes) to afford 50 mg (84%) of the coupled product as a colorless oil.

The coupled product (50 mg, 0.067 mmol) was dissolved in 3.0 mL of anhydrous THF with 37 μL of Et$_3$N, and to this solution was added 0.27 mL (0.27 mmol) of TBAF (1.0 M solution in THF) at room temperature. The reaction was run in darkness overnight, then extracted with EtOAc, washed with brine, dried over anhydrous MgSO$_4$, concentrated in vacuo and then purified by column chromatography (90% EtOAc/Hexanes) to give 33 mg (96%) of a mixture of two diastereomers as a colorless oil. The diastereomers were separated by reverse phase HPLC (C-18 semipreparative column, 52% MeCN/H$_2$O, 3.0 mL/min) to afford 16.6 mg (41%) of Formula V-1 (1α, 3β, $t_R$ 145.3 min) as a foaming solid and 7.0 mg (17%) of Formula V-2 (1β, 3α, $t_R$ 129.2 min) as a colorless oil. Formula V-1: $[\alpha]^{25}_D$+0.1° (c 1.7, CHCl$_3$); $^1$H NMR (400 MHz, CDCl$_3$) δ6.36 (d, J=11.2 Hz, 1H), 6.10 (d, J=11.2 Hz, 1H), 5.40–5.30 (m, 2H), 5.00 (s, 1H), 4.43 (dd J=8.0, 4.4 Hz, 1H), 4.23 (m, 1H), 2.81 (dd, J=12.0, 4.0 Hz, 1H), 2.59 (dd, J=13.2, 2.8 Hz, 1H), 2.43–2.13 (m, 5H), 2.09–1.96 (m, 2H), 1.95–1.63 (m, 9H), 1.51 (s, 9H), 1.07 (d, J=6.8 Hz, 3H), 0.68 (s, 3H); $^{13}$C NMR (100 MHz, CDCl$_3$) δ158.19, 147.85, 142.36, 133.43, 129.60 (t, J=287.7 Hz), 124.99, 121.67, 117.21, 111.88, 70.82, 67.07, 63.34, 58.52, 50.18, 45.35, 43.02, 35.42, 32.58, 29.65, 28.94, 28.70 (t, J=19.6 Hz), 26.81, 24.36, 23.77, 21.79, 17.05; $^{19}$F NMR (376 MHz, CDCl$_3$, CFCl$_3$ as internal) δ−97.86 (m); UV (EtOH) λ$_{max}$ 263 nm (ε 16,100); IR (neat, cm$^{-1}$) 3601, 2931, 2837, 1455, 1314, 1126, 1043; HRMS m/z (M$^+$) calcd 512.2772 for C$_{28}$H$_{42}$F$_2$O$_4$S, found 512.2781. Formula V-2: $[\beta]^{25}_D$ –24.1° (c 0.7, CHCl$_3$); $^1$H NMR (400 MHz, CDCl$_3$) δ6.39 (d, J=11.2 Hz, 1H), 6.10 (d, J=11.2 Hz, 1H), 5.35 (t, J=1.2 Hz, 1H), 5.32 (s, 1H), 5.01 (d, J=2.0 Hz, 1H), 4.44 (dd, J=6.0, 4.0 Hz, 1H), 4.22 (m, 1H), 2.82 (dd, J=11.8, 4.2 Hz, 1H), 2.62 (dd, J=13.2, 4.0 Hz, 1H), 2.42–2.12 (m, 5H), 2.10–1.96 (m, 2H), 1.95–1.55 (m, 9H), 1.52 (s, 9H), 1.07 (d, J=6.8 Hz, 3H), 0.68 (s, 3H); $^{13}$C NMR (100 MHz, CDCl$_3$) δ158.20, 147.22, 142.49, 133.18, 129.62 (t, J=288.0 Hz), 125.09, 121.66, 117.20, 113.29, 71.80, 66.96, 63.35, 58.53, 50.20, 45.78, 42.94, 35.40, 32.58, 29.70, 28.94, 28.69 (t, J=19.1 Hz), 26.82, 24.38, 23.77, 21.81, 17.07; $^{19}$F NMR (376 MHz, CDCl$_3$, CFCl$_3$ as internal) δ–97.88 (m); UV (EtOH) $\lambda_{max}$ 263 nm($\epsilon$ 15,000); IR (neat, cm$^{-1}$) 3683, 3601, 2931, 1314, 1132, 1043; HRMS m/z (M$^+$) calcd 512.2772 for C$_{28}$H$_{42}$F$_2$O$_4$S, found 512.2776.

Preparation of the Formula VI materials is set forth in Scheme 5 as follows:

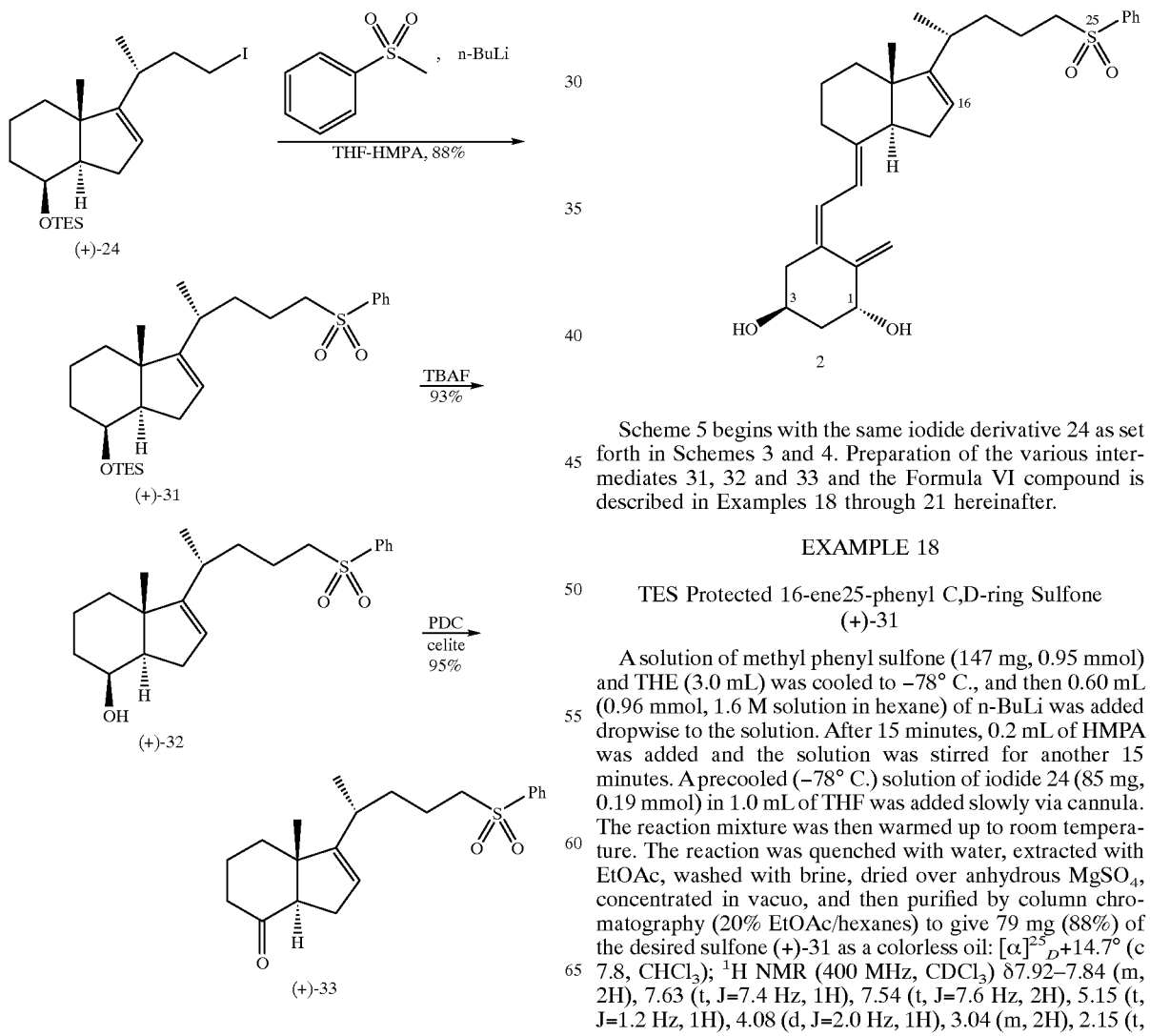

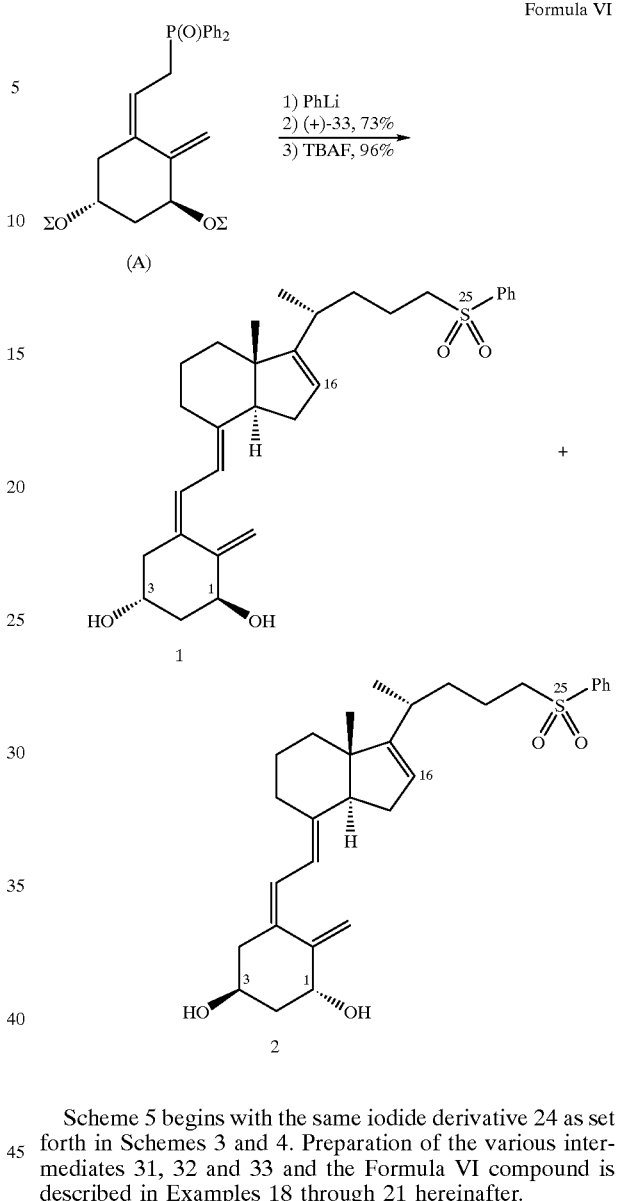

Scheme 5 begins with the same iodide derivative 24 as set forth in Schemes 3 and 4. Preparation of the various intermediates 31, 32 and 33 and the Formula VI compound is described in Examples 18 through 21 hereinafter.

EXAMPLE 18

TES Protected 16-ene25-phenyl C,D-ring Sulfone (+)-31

A solution of methyl phenyl sulfone (147 mg, 0.95 mmol) and THF (3.0 mL) was cooled to –78° C., and then 0.60 mL (0.96 mmol, 1.6 M solution in hexane) of n-BuLi was added dropwise to the solution. After 15 minutes, 0.2 mL of HMPA was added and the solution was stirred for another 15 minutes. A precooled (–78° C.) solution of iodide 24 (85 mg, 0.19 mmol) in 1.0 mL of THF was added slowly via cannula. The reaction mixture was then warmed up to room temperature. The reaction was quenched with water, extracted with EtOAc, washed with brine, dried over anhydrous MgSO$_4$, concentrated in vacuo, and then purified by column chromatography (20% EtOAc/hexanes) to give 79 mg (88%) of the desired sulfone (+)-31 as a colorless oil: $[\alpha]^{25}_D$ +14.7° (c 7.8, CHCl$_3$); $^1$H NMR (400 MHz, CDCl$_3$) δ7.92–7.84 (m, 2H), 7.63 (t, J=7.4 Hz, 1H), 7.54 (t, J=7.6 Hz, 2H), 5.15 (t, J=1.2 Hz, 1H), 4.08 (d, J=2.0 Hz, 1H), 3.04 (m, 2H), 2.15 (t, J=13.0 Hz, 1H), 2.01–1.76 (m, 3H), 1.73–1.22 (m, 10H), 0.95 (t, J=8.0 Hz, 9H), 0.92 (d, J=6.8 Hz, 3H), 0.87 (s, 3H), 0.55 (q, J=8.0 Hz, 6H); $^{13}$C NMR (100 MHz, CDCl$_3$) δ159.31, 139.19, 133.71, 129.32, 128.25, 120.35, 69.03, 56.58, 55.15, 46.72, 35.82, 35.06, 35.02, 31.52, 30.82, 22.50, 21.25, 18.86, 18.16, 7.14, 5.07; IR (neat, cm$^{-1}$) 2953, 2874, 1447, 1319, 1306, 1148, 1082, 1028; HRMS m/z (M$^+$) calcd 476.2780 for C$_{27}$H$_{44}$O$_3$SSi, found 476.2787.

EXAMPLE 19

Deprotected 25-phenyl C,D-ring Sulfone (O)-32

A solution of silyl ether (+)-31 (78 mg, 0.16 mmol) in THF (2.0 mL) and 0.41 mL of 1.0 M solution of TBAF in THF was stirred overnight at room temperature. The mixture was quenched with water and extracted with EtOAc. The combined organic portions were washed with brine, dried, concentrated in vacuo and then purified by column chromatography (20% EtOAc/hexanes) to give 55 mg (93%) of the desired alcohol (₥)-32 as a colorless oil: $[\alpha]^{25}_D$ –0.8° (c 5.8, CHCl$_3$); $^1$H 'NMR (400 MHz, CDCl$_3$) δ7.92–7.84 (m, 2H), 7.63 (t, J=7.4 Hz, 1H), 7.58–7.50 (m, 2H), 5.20 (t, J=1.4 Hz, 1H), 4.13 (d, J=2.4 Hz, 1H), 3.04 (m, 2H), 2.18 (t, J=13.2 Hz, 1H), 2.02–1.18 (m, 13H), 0.93 (d, J=6.8 Hz, 3H), 0.92 (s, 3H); $^{13}$C NMR (100 MHz, CDCl$_3$) δ159.20, 139.21, 133.78, 129.37, 128.20, 120.51, 69.12, 56.54, 54.49, 46.43, 35.52, 35.04, 33.98, 31.60, 30.32, 22.34, 21.20, 18.49, 17.89; IR (neat, cm$^{-1}$) 3535, 2926, 2864, 1447, 1305, 1147, 1086; HRMS m/z (M$^+$) calcd 362.1916 for C$_{21}$H$_{30}$O$_3$S, found 362.1913.

EXAMPLE 20

C,D-ring Ketone (+)-33

To a solution of the C,D-ring alcohol (+)-32 (55 mg, 0.15 mmol) in CH$_2$Cl$_2$ (3.0 mL) were added 114 mg of oven-dried celite and pyridinium dichromate (PDC, 114 mg, 0.30 mmol) at room temperature. The reaction mixture was stirred overnight and then passed through a 2 cm pad of flash silica gel and washed with EtOAc. The filtrate was concentrated and purified by column chromatography (50% EtOAc/hexanes) to afford 52 mg (95%) of the desired C,D-ring ketone (+)-33 as a colorless oil: $[\alpha]^{25}_D$+11.2° (c 5.1, CHCl$_3$); $^1$H NMR (400 MHz, CDCl$_3$) δ7.88–7.82 (m, 2H), 7.63 (t, J=7.4 Hz, 1H), 7.53 (t, J=7.6 Hz, 2H), 5.18 (t, J=1.4 Hz, 1H), 3.03 (t, J=7.8 Hz, 2H), 2.77 (dd, J=10.8, 6.4 Hz, 1H), 2.38–2.20 (m, 3H), 2.12–1.36 (m, 10H), 0.98 (d, J=6.8 Hz, 3H), 0.67 (s, 3H); $^{13}$C NMR (100 MHz, CDCl$_3$) δ210.93, 157.03, 139.13, 133.83, 129.38, 128.13, 120.91, 63.10, 56.37, 53.80, 40.58, 34.87, 34.40, 32.58, 27.14, 24.07, 21.80, 21.05, 17.32; IR (neat, cm$^{-1}$) 2943, 2861, 1708, 1443, 1302, 1143, 1085; HRMS m/z (M$^+$) calcd 360.1759 for C$_{21}$H$_{28}$O$_3$S, found 360.1758.

EXAMPLE 21

Analogs Formula VI

A solution of 89 mg (0.15 mmol) of recemic phosphine oxide (A-ring) in 2.0 mL of anhydrous THF was cooled to −78° C. and treated with 100 μL (0.15 mmol, 1.5 M solution in THF) of phenyllithium under argon atmosphere. The mixture turned reddish orange and was stirred for 30 min at −78° C. To the solution was added dropwise a solution of 52 mg (0.14 mmol) of the C,D-ring ketone (+)-33 in 1.0 mL of anhydrous THF. The reaction kept going on until the reddish orange color faded to yellow (about 4 hours). The reaction was quenched by adding 3.0 mL of a 1:1 mixture of 2 N sodium potassium tartrate and 2 N K$_2$CO$_3$ solution. The reaction mixture was extracted with EtOAc, washed with brine, dried over anhydrous MgSO$_4$, concentrated in vacuo, and then purified by column chromatography (20% EtOAc/hexanes) to afford 76 mg (73%) of the coupled product as a colorless oil.

The coupled product (76 mg, 0.10 mmol) was dissolved in 3.0 mL of anhydrous THF, and to this solution were added TBAF (0.41 mL, 0.41 mmol, 1.0 M solution in THF) and 59 μL of Et$_3$N. The reaction was run in darkness overnight, then quenched with water, extracted with EtOAc, washed with brine, dried over anhydrous MgSO$_4$, concentrated in vacuo and then purified by column chromatography (90% EtOAc/hexanes) to give 52 mg (96%) of a mixture of two diastereomers as a colorless oil. The diastereomers were separated by reverse phase HPLC (C-18 semipreparative column, 50% MeCN1H$_2$O, 3.0 mL/min) to afford 19.1 mg (28%) of Formula VI-1 (1α, 3β, t$_R$ 59.3 min) and 12.7 mg (18%) of Formula VI-2 (1β, 3α, t$_R$ 53.6 min) as colorless oils. Formula VI-1: $[\alpha]^{25}_D$–1.6° (c 1.9, CHCl$_3$); $^1$H NMR (400 MHz, CDCl$_3$) δ7.94–7.86 (m, 2H), 7.65 (t, J=7.4 Hz, 1H), 7.60–7.52 (m, 2H), 6.35 (d, J=11.2 Hz, 1H), 6.08 (d, J=11.2 Hz, 1H), 5.35 (d, J=1.6 Hz, 2H), 5.01 (s, 1H), 4.44 (dd, J=8.0, 4.0 Hz, 1H), 4.23 (m, 1H), 3.05 (t, J=8.0 Hz, 2H), 2.79 (dd, J=12.4, 4.4 Hz, 1H), 2.59 (dd, J=13.2, 2.8 Hz, 1H), 2.40–2.26 (m, 2H), 2.20–2.00 (m, 3H), 2.00–1.84 (m, 2H), 1.84–1.20 (m, 9H), 0.98 (d, J=6.8 Hz, 3H), 0.58 (s, 3H); $^{13}$C NMR (100 MHz, CDCl$_3$) δ158.80, 147.93, 142.36, 139.30, 133.81, 133.43, 129.41, 128.26, 124.98, 121.14, 117.16, 111.71, 70.76, 67.07, 58.47, 56.57, 50.16, 45.31, 43.08, 35.41, 34.98, 32.66, 29.55, 28.92, 23.74, 21.79, 21.02, 17.08; UV (EtOH) λ$_{max}$ 264 nm (ε 12,400); IR (neat, cm$^{-1}$)3613, 2919, 2837, 1443, 1302, 1143, 1043; HRMS m/z (M$^+$) calcd 496.2647 for C$_{30}$H$_{40}$O$_4$S, found 496.2635. Formula VI-2: $[\alpha]^{25}_D$–22.8° (c 1.3, CHCl$_3$); $^1$H NMR (400 MHz, CDCl$_3$) δ7.94–7.86 (m, 2H), 7.65 (t, J=7.4 Hz, 1H), 7.60–7.52 (m, 2H), 6.38 (d, J=11.2 Hz, 1H), 6.07 (d, J=11.2 Hz, 1H), 5.33 (s, 1H), 5.23 (d, J=1.2 Hz, 1H), 5.01 (d, J=1.6 Hz, 1H), 4.46 (dd, J=5.6, 4.0 Hz, 1H), 4.22 (m, 1H), 3.05 (t, J=8.0 Hz, 2H), 2.80 (dd, J=11.6, 4.0 Hz, 1H), 2.62 (dd, J=13.0, 3.8 Hz, 1H), 2.36–2.24 (m, 2H), 2.20–1.86 (m, 5H), 1.84–1.20 (m, 9H), 0.98 (d, J=6.8 Hz, 3H), 0.58 (s, 3H); $^{13}$C NMR (100 MHz, CDCl$_3$) δ158.83, 147.30, 142.48, 139.34, 133.81, 133.19, 129.42, 128.26, 125.07, 121.13, 117.15, 113.11, 71.75, 66.92, 58.48, 56.59, 50.18, 45.72, 42.99, 35.40, 35.00, 32.67, 29.59, 28.91, 23.72, 21.79, 21.01, 17.11; UV (EtOH) λ$_{max}$ 264 nm (ε 16,400); IR (neat, cm$^{-1}$) 3601, 2919, 2849, 1443, 1302, 1143, 1085, 1043; HRMS m/z (M$^+$) calcd 496.2647 for C$_{30}$H$_{40}$O$_4$S, found 496.2650.

Preparation of the Formula VII materials is described in Scheme 6 as follows:

Scheme 6
Synthesis of Formula VII Calcitriol Analogs

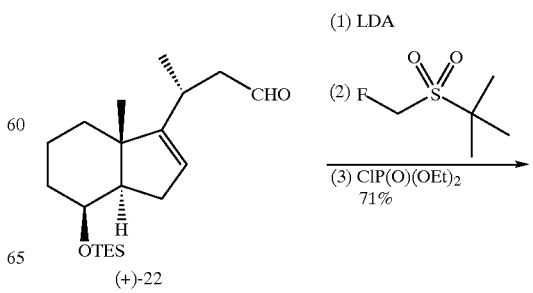

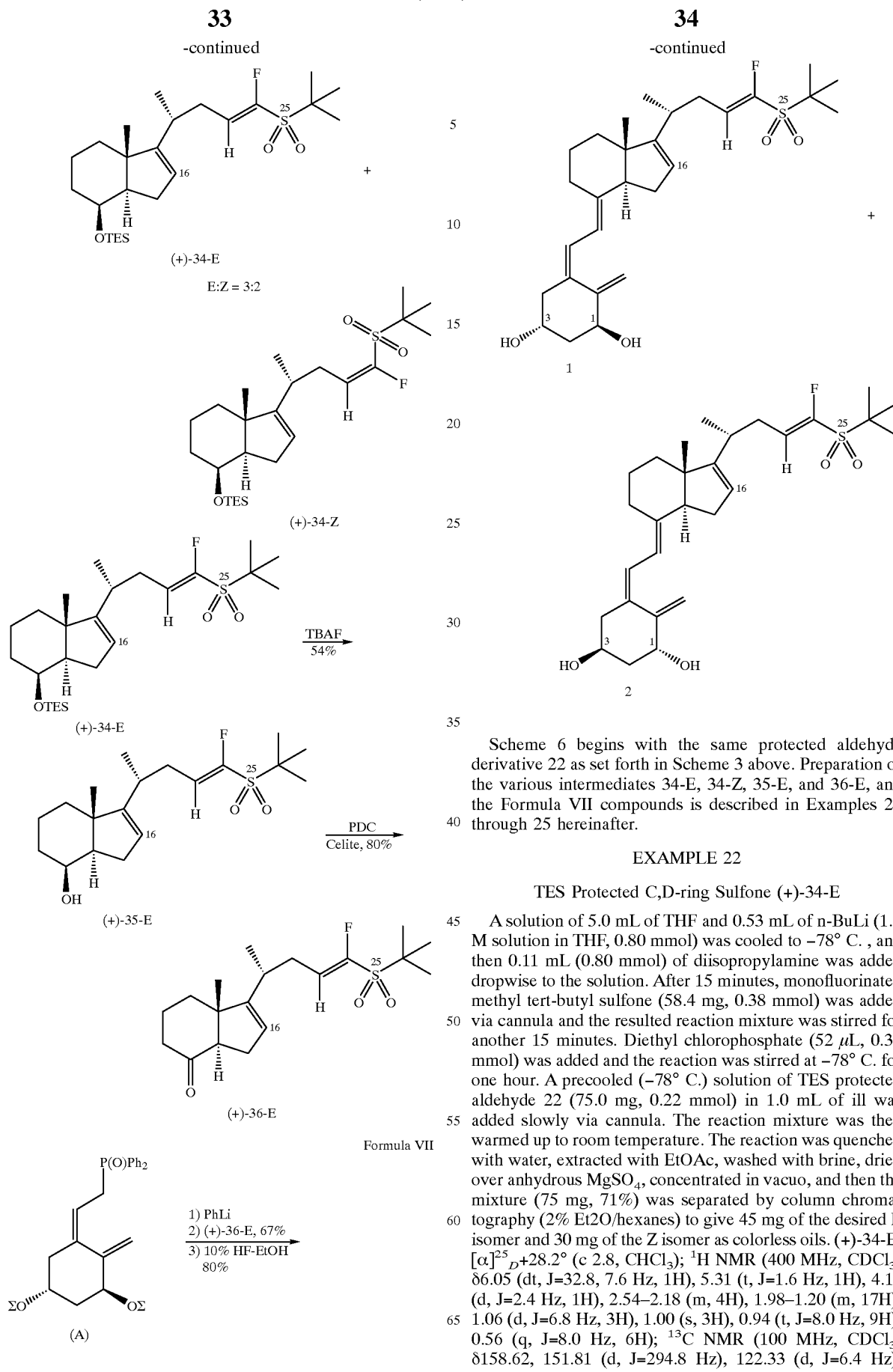

Scheme 6 begins with the same protected aldehyde derivative 22 as set forth in Scheme 3 above. Preparation of the various intermediates 34-E, 34-Z, 35-E, and 36-E, and the Formula VII compounds is described in Examples 22 through 25 hereinafter.

EXAMPLE 22

TES Protected C,D-ring Sulfone (+)-34-E

A solution of 5.0 mL of THF and 0.53 mL of n-BuLi (1.5 M solution in THF, 0.80 mmol) was cooled to −78° C., and then 0.11 mL (0.80 mmol) of diisopropylamine was added dropwise to the solution. After 15 minutes, monofluorinated methyl tert-butyl sulfone (58.4 mg, 0.38 mmol) was added via cannula and the resulted reaction mixture was stirred for another 15 minutes. Diethyl chlorophosphate (52 μL, 0.36 mmol) was added and the reaction was stirred at −78° C. for one hour. A precooled (−78° C.) solution of TES protected aldehyde 22 (75.0 mg, 0.22 mmol) in 1.0 mL of ill was added slowly via cannula. The reaction mixture was then warmed up to room temperature. The reaction was quenched with water, extracted with EtOAc, washed with brine, dried over anhydrous $MgSO_4$, concentrated in vacuo, and then the mixture (75 mg, 71%) was separated by column chromatography (2% Et2O/hexanes) to give 45 mg of the desired E isomer and 30 mg of the Z isomer as colorless oils. (+)-34-E: $[\alpha]^{25}_D$+28.2° (c 2.8, $CHCl_3$); $^1H$ NMR (400 MHz, $CDCl_3$) δ6.05 (dt, J=32.8, 7.6 Hz, 1H), 5.31 (t, J=1.6 Hz, 1H), 4.11 (d, J=2.4 Hz, 1H), 2.54–2.18 (m, 4H), 1.98–1.20 (m, 17H), 1.06 (d, J=6.8 Hz, 3H), 1.00 (s, 3H), 0.94 (t, J=8.0 Hz, 9H), 0.56 (q, J=8.0 Hz, 6H); $^{13}C$ NMR (100 MHz, $CDCl_3$) δ158.62, 151.81 (d, J=294.8 Hz), 122.33 (d, J=6.4 Hz), 121.38, 69.02, 59.73, 55.19, 46.95, 35.98, 35.01, 31.41, 31.33, 30.96, 23.47, 22.16, 19.05, 18.22, 7.15, 5.10; $^{19}$F NMR (376 MHz, CDCl$_3$, CFCl$_3$ as internal) δ–119.77 (d, J=33.5 Hz); IR (neat, cm$^{-1}$) 2954, 2931, 2860, 1666, 1455, 1320, 1132, 1026; HRMS m/z (M$^+$) pending.

EXAMPLE 23

Deprotected C,D-ring Alcohol (+)-35E

A solution of silyl ether (+)-34-E (73.5 mg, 0.16 mmol) and TBAF (0.39 mL, 1.0 M solution in THF, 0.39 mmol) in 2.0 mL of THF was stirred for 4 hours at room temperature. The mixture was quenched with water and extracted with EtOAc. The combined organic portions were washed with brine, dried, concentrated in vacuo and then purified by column chromatography (50% EtOAc/hexanes) to give 30 mg (54%) of the desired alcohol as a colorless oil: $[\alpha]^{25}_D$+ 6.8° (c 1.9, CHCl$_3$); $^1$H NMR (400 MHz, CDCl$_3$) δ6.05 (dt, J=33.2, 7.8 Hz, 1H), 5.36 (t, J=1.6 Hz, 1H), 4.17 (d, J=2.0 Hz, 1H), 2.55–2.20 (m, 4H), 2.06–1.30 (m, 17H), 1.06 (d, J=6.8 Hz, 3H), 1.03 (s, 3H); $^{13}$C NMR (100 MHz, CDCl$_3$) δ158.45, 151.92 (d, J=295.2 Hz), 122.07 (d, J=6.3 Hz), 121.51, 69.14, 59.72, 54.52, 46.63, 35.64, 34.03, 31.34, 31.32, 30.45, 23.48, 22.14, 18.64, 17.93; $^{19}$F NMR (376 MHz, CDCl$_3$, CFCl$_3$ as internal) δ–119.62 (d, J=33.5 Hz); IR (neat, cm$^{-1}$) 3542, 2919, 2872, 1666, 1455, 1137, 1114; HRMS m/z (M$^+$) pending.

EXAMPLE 24

C,D-ring ketone (+)-36-E

A flame-dried 5 mL flask was charged with 30.0 mg (0.084 mmol) of the C,D-ring alcohol (+)-35-E, 3.0 mL of anhydrous CH$_2$Cl$_2$, 70 mg of oven-dried celite and 63.0 mg (0.17 mmol) of PDC. The reaction mixture was stirred overnight at room temperature and then passed through a 2 cm pad of flash silica gel and washed with EtOAc. The filtrate was concentrated and purified by column chromatography (50% EtOAc/hexanes) to give 24.0 mg (78%) of the desired C,D-ring ketone (+)-36-E as a colorless oil: $[\alpha]^{25}_D$+26.0° (c 2.4, CHCl$_3$); $^1$H NMR (400 MHz, CDCl$_3$) δ6.03 (dt, J=32.8, 7.6 Hz, 1H), 5.35 (t, J=1.2 Hz, 1H), 2.85 (dd, J=10.8, 6.6 Hz, 1H), 2.60–2.20 (m, 6H), 2.18–1.60 (m, 5H), 1.38 (s, 9H), 1.13 (d, J=6.4 Hz, 3H), 0.80 (s, 3H); $^{13}$C NMR (100 MHz, CDCl$_3$) δ210.70, 156.35, 152.31 (d, J=295.7 Hz), 121.95, 121.38 (d, J=6.4 Hz), 63.15, 59.74, 53.90, 40.60, 34.56, 32.24, 31.25, 27.34, 24.12, 23.47, 21.62, 17.54; $^{19}$F NMR (376 MHz, CDCl$_3$, CFCl$_3$ as internal) δ–119.06 (d, J=33.1 Hz); IR (neat, cm$^{31\ 1}$) 2943, 1713, 1666, 1455, 1314, 1120, 1038; HRMS m/z (M$^+$) pending.

EXAMPLE 25

Analogs Formula VII

Racemic phosphine oxide (A-ring, 48.9 mg, 0.084 mmol) was dissolved in 2.0 mL of anhydrous THF and cooled to −78° C. under argon atmosphere. To this solution was added 65 μL (0.08 mmol) of phenyllithium (1.2 M solution in THF) dropwise. The mixture turned deep reddish orange and persisted. After stirring at −78° C. for 30 minutes, a pre-cooled (−78° C.) solution of C,D-ring ketone (+)-36-E (24.2 mg, 0.068 mmol) dissolved in 1.0 mL of anhydrous THF was added dropwise via cannula. The reaction kept going on until the reddish orange color faded to yellow (about 4 hours). The reaction was quenched by adding 3.0 mL of a 1:1 mixture of 2 N sodium potassium tartrate and 2 N K$_2$CO$_3$ solution. The reaction mixture was allowed to warm to room temperature, extracted with EtOAc, washed with brine, dried over anhydrous MgSO$_4$, filtered, concentrated in vacuo, and then purified by column chromatography (8% EtOAc/hexanes) to afford 33 mg (67%) of the coupled product as a colorless oil.

The coupled product (31 mg, 0.043 mmol) was dissolved in 2.0 mL of anhydrous ethanol, and then 0.34 mL of HF (49% solution in water) was added and the resulted reaction mixture was stirred for 1 hour at room temperature. The reaction was quenched with diluted NaHCO$_3$ solution and extracted with EtOAc, washed with brine, dried over anhydrous MgSO$_4$, concentrated in vacuo and then purified by column chromatography (80% EtOAc/Hexanes) to give 17.0 mg (80%) of a mixture of two diastereomers as a colorless oil. The diastereomers were separated by reverse phase HPLC (C-18 semipreparative column, 52% MeCN/H$_2$O, 3.0 mL/min) to afford 5.7 mg (17%) of Formula VII-1 (1α, 3β, $t_R$ 77.3 min) as a foaming solid and 4.2 mg (12%) of Formula VII-2 (1β, 3α, $t_R$ 70.4 min) as a colorless oil. Formula VII-1: $[\alpha]^{25}_D$+3.2° (c 0.57, CHCl$_3$); $^1$H NMR (400 MHz, CDCl$_3$) δ6.36(d, J=11.2 Hz, 1H), 6.10 (d, J=10.8 Hz, 1H), 6.05 (dt, J=33.2, 7.6 Hz, 1H), 5.37 (s, 1H), 5.34 (t, J=1.6 Hz, 1H), 5.00 (s, 1H), 4.44 (dd, J=7.8, 4.2 Hz, 1H), 4.24 (m, 1H), 2.82 (dd, J=12.2, 4.6 Hz, 1H), 2.60 (d, J=13.6 Hz, 1H), 2.54–1.18 (m, 23H), 1.10 (d, J=6.4 Hz, 3H), 0.69 (s, 3H); $^{13}$C NMR (100 MHz, CDCl$_3$) δ158.03, 152.01 (d, J=295.3 Hz), 147.86, 142.11, 133.56, 124.97, 122.12, 121.88 (d, J=6.3 Hz), 117.36, 111.90, 70.89, 67.07, 59.73, 58.51, 50.20, 45.37, 43.08, 35.46, 32.30, 31.26, 29.66, 28.90, 23.72, 23.50, 21.52, 17.21; $^{19}$F NMR (376 MHz, CDCl$_3$, CFCl$_3$ as internal) δ–119.50 (d, J=33.1 Hz); UV (EtOH) λ$_{max}$ 263 nm (ε 14,700); IR (CHCl$_3$, cm$^{-1}$) 3707, 3601, 2919, 1654, 1455, 1314, 1220, 1038; HRMS m/z (M$^+$) pending. Formula VII-2: $[\beta]^{25}_D$–16.7° (c 0.42, CHCl$_3$); $^1$H NMR (400 MHz, CDCl$_3$) δ6.38 (d, J=11.6 Hz, 1H), 6.09 (d, J=10.4 Hz, 1H), 6.05 (dt, J=33.6, 7.6 Hz, 1H), 5.37 (s, 1H), 5.33 (s, 1H), 5.01 (d, J=1.6 Hz, 1H), 4.46 (m, 1H) 4.22 (m, 1H), 2.82 (dd, J=12.0, 4.4 Hz, 1H), 2.62 (dd, J=13.2, 3.6 Hz, 1H), 2.56–1.20 (m, 23H), 1.10 (d, J=6.8 Hz, 3H), 0.69 (s, 3H); $^{13}$C NMR (100 MHz, CDCl$_3$) δ158.03, 152.01 (d, J=295.7 Hz), 147.34, 142.20, 133.38, 125.02, 122.12, 121.89 (d, J=5.9 Hz), 117.36, 113.03, 71.65, 67.00, 59.73, 58.51, 50.22, 45.71, 43.01, 35.45, 32.32, 31.27, 29.70, 28.89, 23.71, 23.51, 21.54, 17.23; $^{19}$F NMR (376 MHz, CDCl$_3$, CFCl$_3$ as internal) δ–119.51 (d, J=32.0 Hz); UV (EtOH) λ$_{max}$ 263 nm (ε 14,900); IR (CHCl$_3$, cm$^{-1}$) 3601, 2919, 2849, 1655, 1455, 1314, 1214, 1038; HRMS m/z (M$^+$) pending.

Preparation of the Formula VIII materials is described in Scheme 7 as follows:

Scheme 7
Synthesis of Formula VIII Calcitriol Analogs

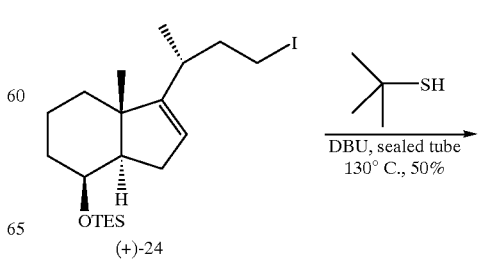

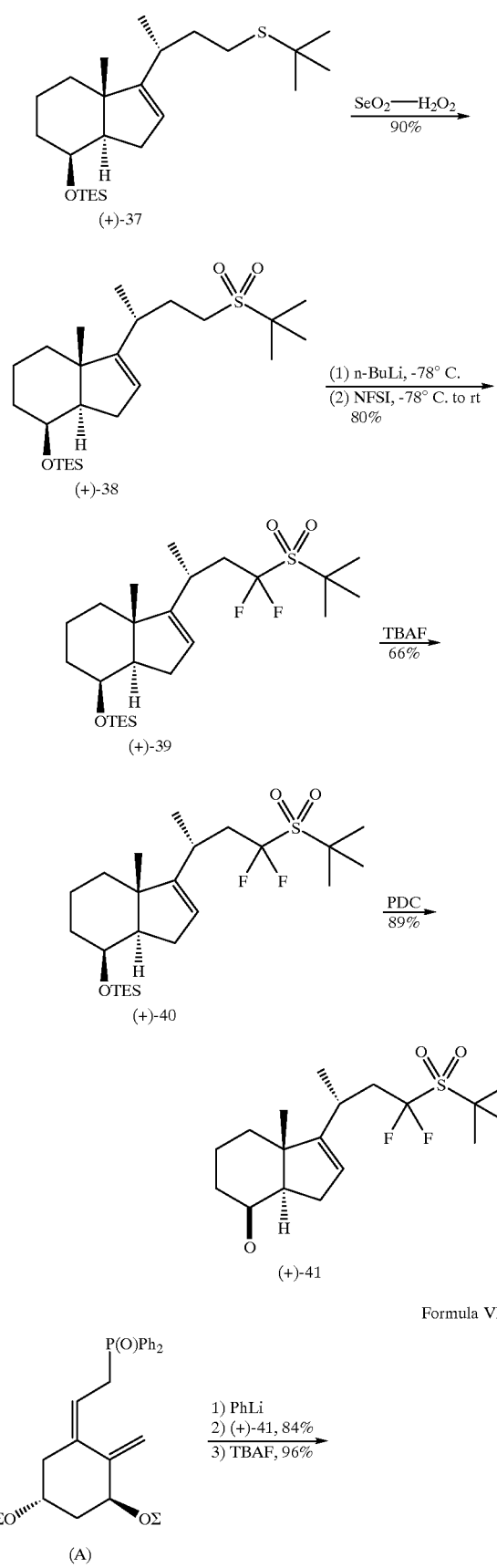

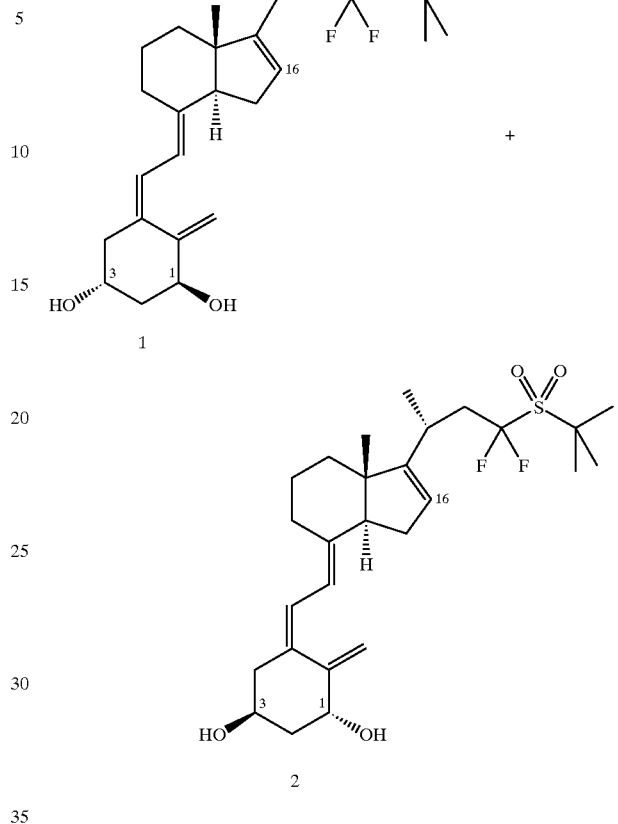

Formula VIII

Scheme 7 begins with the same iodide derivative 24 as set forth in Schemes 3, 4, and 5. Preparation of the various intermediates, 37, 38, 39, 40, and 41, and the Formula VIII compounds is described in Examples 26 through 29 hereinafter.

EXAMPLE 26

Difluorinated C,D-ring Sulfone (+)-39

To a solution of the TES protected C,D-ring sulfone (+)-38 (64 mg, 0.15 mmol) in THF (3.0 mL) was added 0.29 mL (0.58 mmol) of a 2.0 M solution of n-BuLi in pentane at −78° C. Afer being stirred for 30 minutes, a precooled (−78° C.) solution of NFSI (N-fluorobenzenesulfonimide, 127 mg, 0.41 mmol) in 1.0 mL of THF was added slowly to the reaction mixture, and then it was warmed up to room temperature. The reaction was quenched with water and extracted with EtOAc. The combined organic portions were washed with brine, dried, and concentrated in vacuo. Purification by column chromatography (20% EtOAc/hexanes) gave a mixture of mono and di-fluorinated sulfones.

The mixture was dissolved in THF (3.0 mL) and the solution was cooled to −78° C. To the solution was added 0.29 mL of n-BuLi (2.0 M solution in pentane, 0.58 mmol) and the reaction mixture was stirred for 30 minutes at −78° C. A precooled (−78° C.) solution of NFSI (127 mg, 0.41 mmol) in 1.0 mL of THF was then added slowly via cannula. The reaction mixture was warned up to room temperature, quenched with water, extracted with EtOAc, washed with brine and concentrated. Purification by column chromatography (20% EtOAc/hexanes) gave 55 mg (80%) of the desired difluoronated C,D-ring sulfone (+)-39 as a colorless oil: $[\alpha]^{25}_D$+21.9° (c 5.5, CHCl$_3$); $^1$H NMR (400 M , CDCl$_3$) δ5.37 (s, 1H), 4.12 (s, 1H), 2.68–2.18 (m, 4H), 1.96–1.30 (m, 17H), 1.12 (d, J=5.6 Hz, 3H), 1.04 (s, 3H), 0.94 (t, J=7.8 Hz, 9H), 0.56 (q, J=8.0 Hz, 6H); $^{13}$C NMR (100 MHz, CDCl$_3$) δ158.94, 129.52 (t, J=289.2 Hz), 121.67, 69.04, 63.31, 55.13, 47.36, 35.94, 35.05, 31.00, 25.44, 24.44, 23.91, 22.89, 19.01, 18.22, 7.13, 5.11; $^{19}$F NMR (376 MHz, CDCl$_3$, CFCl$_3$ as internal) δ–96.24 (ddd, J=219.2, 31.9, 6.6 Hz), –97.83 (ddd, J=219.6, 29.9, 5.5 Hz); IR (neat, cm$^{-1}$) 2934, 2876, 1458, 1320, 1134, 1029; HRMS m/z (M$^+$) pending.

EXAMPLE 27

Deprotected Difluoronated C,D-ring Alcohol (+)-40

A solution of silyl ether (+)-39 (55 mg, 0.11 mmol) in THF (2.0 mL) and 0.29 mL (0.29 mmol) of 1.0 M solution of TBAF in THF was stirred overnight at room temperature. The mixture was quenched with water and extracted with EtOAc. The combined organic portions were washed with brine, dried, concentrated in vacuo and then purified by column chromatography (20% EtOAc/hexanes) to give 27 mg (66%) of the desired alcohol as a colorless oil: $[\alpha]^{25}_D$+9.3° (c 2.7, CHCl$_3$); $^1$H NMR (400 MHz, CDCl$_3$) δ5.41 (d, J=1.2 Hz, 1H), 4.17 (d, J=2.4 Hz, 1H), 2.72–2.20 (m, 4H), 2.06–1.32 (m, 17H), 1.13 (d, J=6.0 Hz, 3H), 1.06 (s, 3H); $^{13}$C NMR (100 MHz, CDCl$_3$) δ158.70, 129.45 (t, J=289.7 Hz), 121.75, 69.17, 63.38, 54.45, 47.01, 35.96 (t, J=18.6 Hz), 35.60, 34.00, 30.46, 25.44, 24.42, 22.89, 18.57, 17.94; $^{19}$F NMR (376 ZT7, CDCl$_3$, CFCl$_3$ as internal) δ–96.22 (ddd, J=219.6, 32.4, 8.0 Hz), δ–97.76 (ddd, J=219.6, 29.7, 6.8 Hz); IR (neat, cm$^{-1}$) 3566, 3448, 2931, 2860, 1455, 1314, 1126; HRMS m/z (M$^+$) pending.

EXAMPLE 28

C,D-ring ketone (+)-41

A flame-dried 5 mL flask was charged with 27 mg (0.074 mmol) of the C,D-ring alcohol (+)-40, 3.0 mL of anhydrous THF, 100 mg of oven-dried celite and 69 mg (0.19 mmol) of PDC. The reaction mixture was stirred overnight at room temperature and then passed through a 2 cm pad of flash silica gel and washed with EtOAc. The filtrate was concentrated and purified by column chromatography (20% EtOAc/hexanes) to give 24 mg (89%) of the desired C,D-ring ketone (+)-41 as a colorless oil: $[\alpha]^{25}_D$+17.5° (c 2.5, CHCl$_3$); $^1$H NMR (400 MHz, CDCl$_3$) δ5.41 (s, 1H), 2.84 (dd, J=10.4, 6.4 Hz, 1H), 2.74–2.22 (m, 6H), 2.16–1.74 (m, 5H), 1.51 (s, 9H), 1.19 (d, J=6.4 Hz, 3H), 0.84 (s, 3H); $^{13}$C NMR (100 MHz, CDCl$_3$) δ210.76, 156.38, 129.20 (t, J=289.9 Hz), 122.29, 63.47, 63.12, 54.14, 40.62, 36.03 (t, J=18.5 Hz), 34.54, 27.36, 26.48 (t, J=2.7 Hz), 24.41 (t, J=2.6 Hz), 24.11, 22.56, 17.50; $^{19}$F NMR (376 MHz, CDCl$_3$, CFCl$_3$ as internal) δ–96.20 (ddd, J=219.8, 28.9, 9.2 Hz), δ–97.49 (ddd, J=219.8, 28.9, 10.3 Hz); IR (neat, cm$^{-1}$) 2943, 1713, 1314, 1132; HRMS m/z (M$^+$) pending.

EXAMPLE 29

Analogs Formula VIII

Racemic phosphine oxide (A-ring, 43.4 mg, 0.075 mmol) was dissolved in 1.0 mL of anhydrous THF and cooled to −78° C. under argon atmosphere. To this solution was added 58 μL (0.070 mmol) of phenyllithium (1.2 M solution in THF) dropwise. The mixture turned deep reddish orange and persisted. After stirring at −78° C. for 30 minutes, a pre-cooled (−78° C.) solution of C,D-ring ketone (+)-41 (24.8 mg, 0.068 mmol) dissolved in 1.0 mL of anhydrous THF was added dropwise via cannula. The reaction kept going on until the reddish orange color faded to yellow (about 4 hours). The reaction was quenched by adding 3.0 mL of a 1:1 mixture of 2 N sodium potassium tartrate and 2 N K$_2$CO$_3$ solution. The reaction mixture was allowed to warm to room temperature, extracted with EtOAc, washed with brine, dried over anhydrous MgSO$_4$, filtered, concentrated in vacuo, and then purified by column chromatography (10% EtOAc/hexanes) to afford 37.2 mg (75%) of the coupled product as a colorless oil.

The coupled product (37.2 mg, 0.051 mmol) was dissolved in 3.0 mL of anhydrous THF with 29 μL of Et$_3$N, and to this solution was added 0.20 mL (0.20 mmol) of TBAF (1.0 M solution in THF) at room temperature. The reaction was run in darkness overnight, then extracted with EtOAc, washed with brine, dried over anhydrous MgSO$_4$, concentrated in vacuo and then purified by column chromatography (90% EtOAc/Hexanes) to give 18.6 mg (73%) of a mixture of two diastereomers as a colorless oil. The diastereomers were separated by reverse phase HPLC (C-18 semipreparative column, 52% MeCN/H$_2$O, 3.0 mL/min) to afford 7.4 mg (22%) of Formula VIII-1 (1α, 3β, $t_R$ 90.7 min) as a foaming solid and 4.3 mg (13%) of Formula VIII-2 (1β, 3α, $t_R$ 84.3 min) as a colorless oil. Formula VIII-1: $[\beta]^{25}_D$+2.1° (c 0.7, CHCl$_3$); $^1$H NMR (400 MHz, CDCl$_3$) δ6.37 (d, J=11.6 Hz, 1H), 6.10 (d, J=11.2 Hz, 1H), 5.42 (s, 1H), 5.33 (s, 1H), 5.00 (s, 1H), 4.44 (dd, J=7.2, 4.0 Hz, 1H), 4.24 (m, 1H), 2.82 (dd, J=11.8, 4.2 Hz, 1H), 2.74–2.50 (m, 3H), 2.44–2.16 (m, 5H), 2.10–1.48 (m, 16H), 1.17 (d, J=6.8 Hz, 3H), 0.72 (s, 3H); $^{13}$C NMR (100 MHz, CDCl$_3$) δ158.32, 147.83, 142.25, 133.45, 129.44 (t, J=290.0 Hz), 125.03, 122.26, 117.30, 111.92, 70.91, 67.08, 63.40, 58.42, 50.50, 45.39, 43.05, 35.98 (t, J=18.6 Hz), 35.44, 29.67, 28.90, 26.49, 24.45, 23.71, 22.42, 17.14; $^{19}$F NMR (376 MHz, CDCl$_3$, CFCl$_3$ as internal) δ–96.17 (ddd, J=218.6, 32.0, 8.1 Hz), δ–97.64 (ddd, J=219.8, 29.7, 8.5 Hz); UV EtOH) $\lambda_{max}$ 263 nm (ε 16,900); IR (CHCl$_3$, cm$^{-1}$) 3601, 2931, 2849, 1649, 1602, 1455, 1314, 1132, 1043; HRMS m/z (M$^+$) pending. Formula VIII-2: $[\alpha]^{25}_D$–19.3° (c 0.4, CHCl$_3$); $^1$H NMR (400 MHz, CDCl$_3$) δ6.38 (d, J=11.2 Hz, 1H), 6.09 (d, J=11.2 Hz, 1H), 5.42 (s, 1H), 5.32 (s, 1H), 5.01 (d, J=1.2 Hz, 1H), 4.45 (m, 1H), 4.22 (m, 1H), 2.82 (dd, J=12.0, 4.4 Hz, 1H), 2.74–2.50 (m, 3H) 2.44–2.16 (m, 5H), 2.10–1.48 (m, 16H), 1.17 (d, J=6.8 Hz, 3H), 0.72 (s, 31); $^{13}$C NMR (100 MHz, CDCl$_3$) δ158.34, 147.32, 142.32, 133.26, 129.45 (t, J=294.7 Hz), 125.07, 122.26, 117.29, 113.07, 71.70, 66.99, 63.40, 58.41, 50.51, 45.73, 42.98, 35.99 (t, J=18.6 Hz), 35.43, 29.70, 28.89, 26.49, 24.46, 23.71, 22.42, 17.14; $^{19}$F NMR (376 MHz, CDCl$_3$, CFCl$_3$ as internal) δ–96.17 (dd, J=222.0, 28.4 Hz), δ–97.69 (dd, J=219.6, 28.9 Hz); UV (EtOH) $\lambda_{max}$ 262 nm (ε 14,000); IR (CHCl$_3$, cm$^{-1}$) 3601, 2931, 2849, 1455, 1314, 1132, 1038; HRMS m/z (M$^+$) pending.

Preparation of the Formula IX materials is described in Scheme 8 as follows:

Scheme 8
Synthesis of Formula IX Calcitriol Analogs

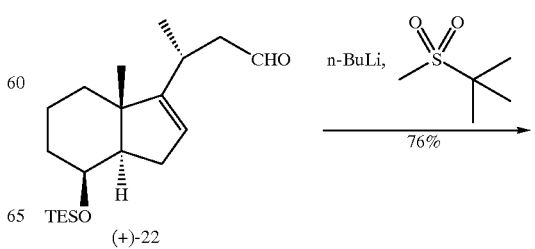

41
-continued

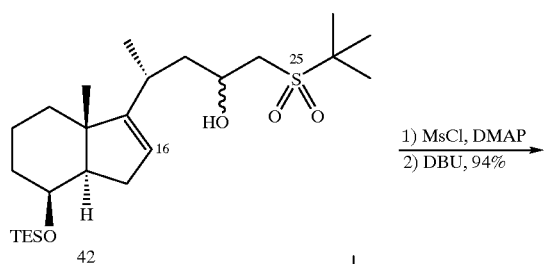

1) MsCl, DMAP
2) DBU, 94%

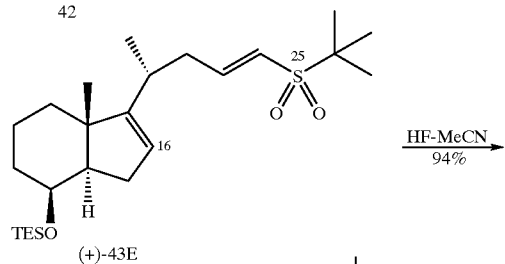

HF-MeCN
94%

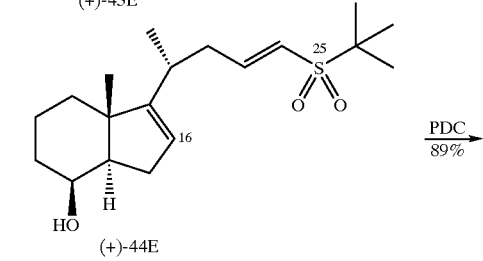

PDC
89%

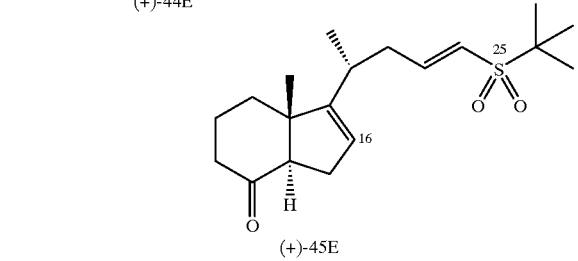

Formula IX

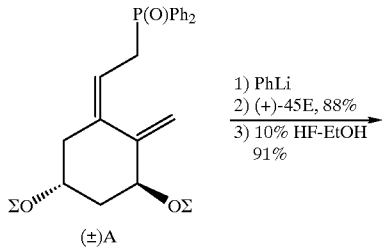

1) PhLi
2) (+)-45E, 88%
3) 10% HF-EtOH
91%

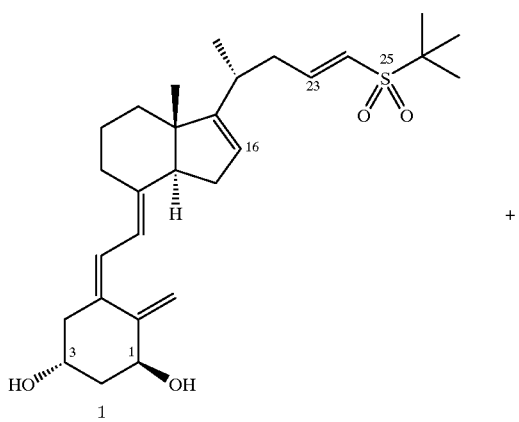

+

42
-continued

Scheme 8 begins with the same aldehyde derivative as set forth in Schemes 3 and 6. Preparation of the various intermediates, 42, 43E, 44E, and 45E, and the Formula IX compounds is described in Examples 30 through 34 hereinafter.

EXAMPLE 30

16-Ene-23-Hydroxy-25-Sulfones 42

To a solution of methyl t-butylsulfone (103 mg, 0.76 mmol) in 10 mL of THF was added 0.52 mL of n-BuLi (1.60 M, 0.83 mmol) dropwise at −78° C. After 1 h at −78° C., a solution of aldehyde (+)-22 (45 mg, 0.13 mmol) in 10 mL of THF was added dropwise at −78° C. After 2 h at −78° C., the reaction mixture was quenched with saturated ammonium chloride solution (20 mL) and extracted with EtOAc (50 mL×3). The combined organic portions were washed with brine (30 mL), dried over $MgSO_4$ and concentrated. The crude product was purified by flash column chromatography (33% EtOAc/hexanes) to give 45 mg (76%) of diastereomeric alcohols 42 as colorless oils: $^1H$ NMR (400 MHz, $CDCl_3$) δ5.33 and 5.27 (two s, 1H), 4.48 and 4.38 (two s, 1H), 4.12 (s, 1H), 3.47 and 3.37 (two s, 1H), 3.09–2.94 (m, 2H), 2.41 (m, 1H), 2.26 (m, 1H), 1.91–1.41 (m, 13H), 1.42 and 1.41 (two s, 9H), 1.04 (m, 6H), 0.95 and 0.94 (t, J=8.0 Hz, 9H), 0.56 and 0.55 (q, J=8.0 Hz, 6H); IR (neat, $cm^{-1}$) 3523, 2932, 1290, 1114; HRMS m/z ($M^+$) calcd 472.3043 for $C_{25}H_{48}O_4SSi$, found 472.3037.

EXAMPLE 31

16,23-Diene-25-Sulfone (+)-43E

To a solution of alcohols 42 (42 mg, 0.089 mmol) in 10 mL of dry $CH_2Cl_2$ was added 0.20 mL of triethylamine and methanesulfonyl chloride (0.050 mL, 0.65 mmol) at 0° C. The mixture was stirred for 1 h at 0° C. The solution was concentrated in vacuo. The residue was diluted with brine (20 mL) and extracted with EtOAc (30 mL×3). The combined organic portions were dried over $MgSO_4$ and concentrated. The crude mesylates were used for the next step without further purification.

To a solution of the mesylates in 7 mL of dry benzene was added 1,8-diazabicyclo[5.4.0]undec-7-ene (0.050 mL, 0.33 mmol). The solution was gently refluxed for 15 min and then allowed to cool to room temperature. The reaction mixture was diluted with brine (20 mL) and extracted with EtOAc (30 mL×3). The combined organic portions were dried over $MgSO_4$ and concentrated. The crude product was purified by flash chromatography (33% EtOAc/hexanes) to give 38 mg (94%) of the unsaturated sulfone (+)-43E as a colorless oil: $[\alpha]^{25}_D$+20.0 (c 1.4, $CHCl_3$); $^1$H NMR (400 MHz, $CDCl_3$) δ6.81 (dt, J=14.8, 7.6 Hz, 1H), 6.23 (d, J=15.2 Hz, 1H), 5.29 (s, 1H), 4.11 (s, 1H), 2.51 (m, 1H), 2.41–2.02 (m, 3H), 1.91 (m, 2H), 1.73–1.37 (m, 10H), 1.04 (d, J=6.4 Hz, 3H), 1.01 (s, 3H), 0.94 (t, J=8.0 Hz, 9H), 0.56 (q, J=8.0 Hz, 6H); $^{13}$C NMR (100 MHz, $CDCl_3$) δ158.38, 150.43, 124.31, 121.34, 68.75, 58.17, 54.95, 46.75, 38.76, 35.78, 34.74, 30.91, 30.70, 23.23, 21.83, 18.84, 17.96, 6.88, 4.83; IR (neat, $cm^{-1}$) 2932, 1294, 1115; HRMS m/z pending.

EXAMPLE 32

16,23-Diene-8-Hydroxy-25-Sulfone (+)-44E

To a solution of the sulfone (+)-43E (24 mg, 0.053 mmol) in 10 mL of acetonitrile was added hydrofluoric acid (2% in $H_2O$, 0.10 mL, 0.10 mmol) at 0° C. After 2 h at 0° C., the reaction mixture was quenched with saturated $NaHCO_3$ solution (20 mL) and extracted with EtOAc (30 mL×3). The combined organic layers were washed with brine (30 mL), dried over $MgSO_4$ and concentrated. The crude product was purified by flash chromatography (50% EtOAc/hexanes) to give 17 mg (94%) of the alcohol (+)-44E as a colorless oil: $[\alpha]^{25}_D$+5.9 (c 2.9, $CHCl_3$); $^1$H NMR (400 MHz, $CDCl_3$) δ6.82 (dt, J=15.2, 7.6 Hz, 1H), 6.25 (dt, J=15.2, 1.6 Hz, 1H), 5.35 (s, 1H), 4.18 (s, 1H), 2.54–2.22 (m, 4H), 2.02–1.52 (m, 14H), 1.35 (s, 9H), 1.06 (d, J=8.0 Hz, 3H), 1.05 (s, 3H); $^{13}$C NMR (100 MHz, $CDCl_3$) δ158.30, 150.22, 124.45, 121.45, 68.89, 58.19, 54.31, 46.46, 38.72, 35.47, 33.79, 30.99, 30.22, 23.28, 21.84, 18.46, 17.70; IR (neat, $cm^{-1}$) 3526, 2927, 1290, 1120; HRMS m/z $(M+NH_4^+)$ calcd 358.2416 for $C_{19}H_{32}O_3S$, found 358.2408.

EXAMPLE 33

16,23-Diene-8-Keto-25-Sulfone (+)-45E

To a solution of the alcohol (+)-44E (28 mg, 0.083 mmol) in 10 mL of dry $CH_2Cl_2$ was added 57 mg of oven dried celite and pyridinium dichlomate (57 mg, 0.15 mmol) at rt. After 16 h, the reaction mixture was filtered through a flash silica gel pad, and then eluted with EtOAc. The filtrate was concentrated and purified by flash chromatography (50% EtOAc/hexanes) to give 25 mg (89%) of the ketone (+)-45E as a colorless oil: $[\alpha]^{25}_D$+22.2 (c 2.0, $CHCl_3$); $^1$H NMR (400 MHz, $CDCl_3$) δ6.78 (dt, J=15.2, 7.6 Hz, 1H), 6.25 (d, J=15.2 Hz, 1H), 5.33 (s, 1H), 2.85 (m, 1H), 2.55–2.27 (m, 6H), 2.15–1.74 (m, 7H), 1.33 (s 9H), 1.11 (d, J=6.4 Hz, 3H), 0.81 (s, 3H); $^{13}$C NMR (100 MHz, $CDCl_3$) δ210.43, 156.21, 149.49, 124.89, 121.80, 62.89, 58.19, 53.69, 40.34, 38.56, 34.35, 27.09, 23.86, 23.25, 21.35, 17.32; IR (neat, $cm^{-1}$) 2935, 1715, 1289, 1113; HRMS m/z $(M+NH_4^+)$ calcd 356.2259 for $C_{19}H_{30}O_3S$, found 356.2266.

EXAMPLE 34

16,23-Diene-25-Sulfone Analogs (−)-Formula IX-1 and (−)-Formula IX-2

To a solution of racemic phosphine oxide (±)-A (60 mg, 0.10 mmol) in 1 mL of anhydrous THF was treated dropwise with phenyllithium (1.22 M in cyclohexane-ether, 0.082 mL, 0.10 mmol) at −78° C. The resulting reddish orange solution was stirred at −78° C. for 30 min and then a solution of the ketone (+)-45E (24 mg, 0.071 mmol) in 1 mL of anhydrous THF was added dropwise. The reaction mixture was stirred until reddish color tuned to pale yellow, and then quenched with 3 ml of a 1:1 mixture of 2 N sodium potassium tartrate solution and 2 N $K_2CO_3$ solution. The aqueous layer was extracted with EtOAc (50 mL×3). The combined organic portions were washed with brine (50 mL), dried over $MgSO_4$, and concentrated. The residue was purified by preparative TLC (EtOAc) to give 44 mg (88%) of the coupled product as a colorless oil.

To a solution of the coupled product (44 mg, 0.062 mmol) in 2 mL of anhydrous ethanol was added hydrofluoric acid (49% in $H_2O$, 0.50 mL, 12.3 mmol). The solution was stirred at rt for 2 h in dark. The reaction mixture was quenched with $NaHCO_3$ solution (20 mL) and the aqueous layer was extracted with EtOAc (30 mL×3). The combined organic portions were washed with brine (20 mL), dried over $MgSO_4$, and concentrated. The residue was purified by preparative TLC (EtOAc) to give 27 mg (91%) of diastereomeric diols Formula IX as colorless oils. The diastereomers were separated by reverse phase HPLC (C-18 semi preparative column, 52% MeCN/48% $H_2O$, 3 mL/min) to give 12 mg (36%) of (−)-Formula IX-1 (1α,3β, $t_R$ 30.2 min) and 9 mg (27%) of(−)-Formula IX-2 (1β,3α, $t_R$ 27.1 min) as colorless oils. (−)-Formula IX-1: $[\alpha]^{25}_D$−2.5 (c 1.1, $CHCl_3$); $^1$H NMR (400 MHz, $CDCl_3$) δ6.81 (dt, J=15.2, 7.4 Hz, 1H), 6.36 (d, J=11.2 Hz, 1H), 6.24 (d, J=15.2 Hz, 1H), 6.10 (d, J=11.6 Hz, 1H), 5.34 (two s, 2H), 5.00 (s, 1H), 4.44 (m, 1H), 4.24 (m, 1H), 2.88 (dd, J=12.4, 4.2 Hz, 1H), 2.61–2.48 (m, 3H), 2.38–2.14 (m, 7H), 2.06–1.51 (m, 18H), 1.34 (s, 9H), 1.09 (d, J=6.4 Hz, 3H), 0.70 (s, 3H); $^{13}$C NMR (100 MHz, $CDCl_3$) δ157.86, 150.15, 147.63, 141.81, 133.37, 124.70, 124.50, 122.98, 117.14, 111.64, 70.62, 66.83, 58.28, 58.21, 50.02, 45.12, 42.84, 38.64, 35.29, 32.00, 29.43, 28.67, 23.49, 23.29, 21.29, 17.03; IR (neat, $cm^{-1}$) 3606, 2931, 1291, 1113; UV (EtOH) $\lambda_{max}$ 263 nm (ε 11,793); HRMS m/z pending. (−)-Formula IX-2: $[\alpha]^{25}_D$−10.9 (C 0.8, $CHCl_3$); $^1$H NMR (400 MHz, $CDCl_3$) δ6.81 (dt, J=15.2, 7.6 Hz, 1H), 6.38 (d, J=11.6 Hz, 1H), 6.24 (d, J=15.2 Hz, 1H), 6.09 (d, J=11.2 Hz, 1H), 5.35 and 5.33 (two s, 2H), 5.01 (s, 1H), 4.46 (m, 1H), 4.23 (m, 1H), 2.83 (dd, J=12.8, 4.0 Hz, 1H) 2.46–2.48 (m, 3H), 2.34–2.15 (m, 7H), 2.05–1.52 (m, 20H), 1.35 (s, 9H), 1.09 (d, J=6.4 Hz, 3H), 0.69 (s, 3H) ); $^{13}$C NMR (100 MHz, $CDCl_3$) δ157.86, 150.15, 147.09, 141.91, 133.18, 124.76, 124.52, 121.98, 117.14, 112.82, 71.42, 66.74, 58.28, 58.22, 50.03, 45.47, 42.78, 38.64, 35.28, 32.01, 29.47, 28.66, 23.48, 23.30, 21.32, 17.05; R (neat, $cm^{-1}$) 3606, 2931, 1291, 1112; UV (EtOH) $\lambda_{max}$ 263 nm (ε 11,572); .HRMS m/z pending.

Preparation of the Formula X materials is described in Scheme 9 as follows:

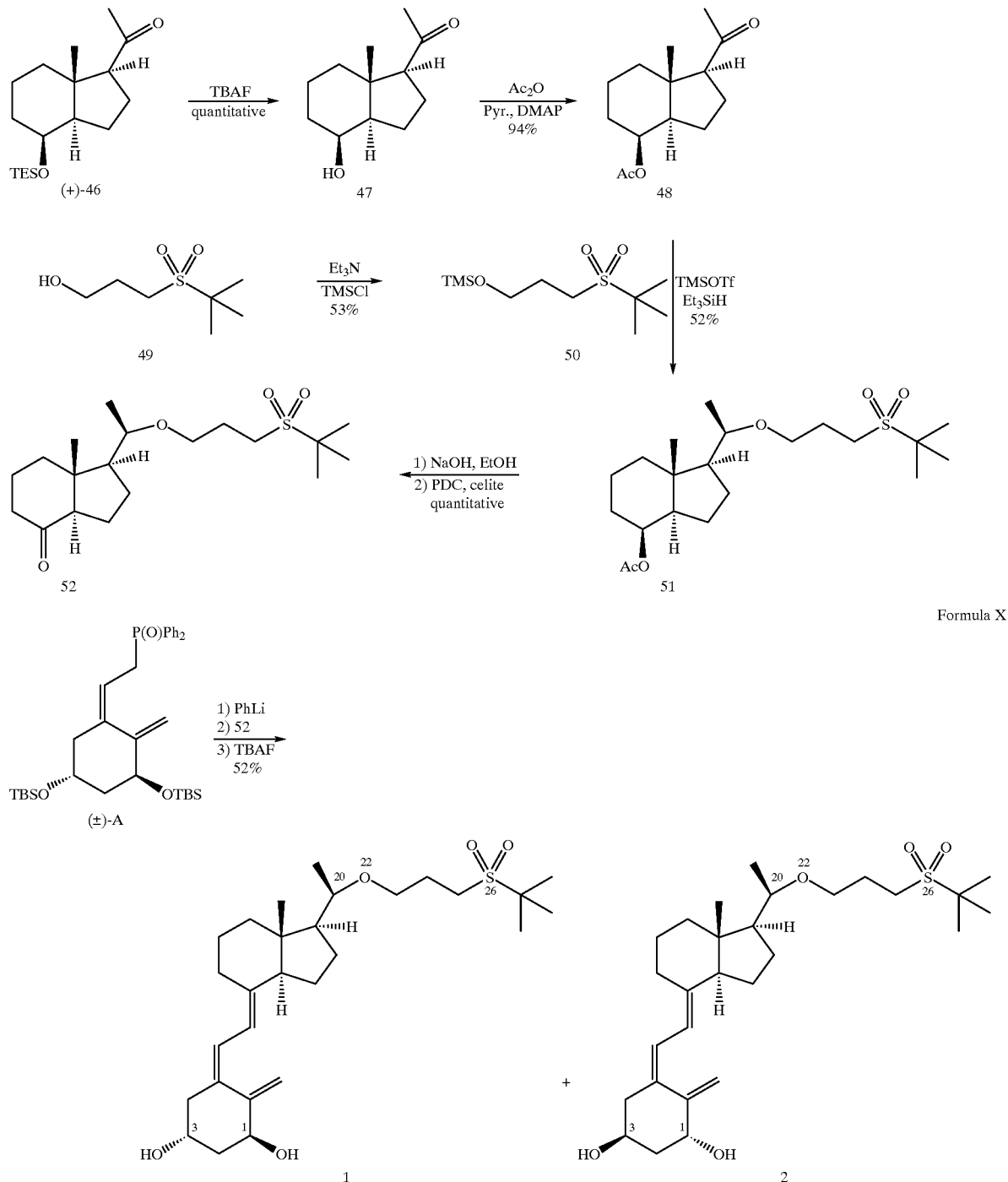

Scheme 9 begins with a ketone derivative 46, the preparation of which is described in Posner et al; *J. Org. Chem.* Vol. 62. 1997 at pp. 3299–3314 and also uses t-butyl, 3-hydroxypropyl sulfone 49 as a reagent. Preparation of the various intermediates 47, 48, 50, 51 and 52 and the Formula X compounds is described in Examples 35 through 40 hereinafter.

EXAMPLE 35

Hydroxy Ketone 47

To a solution of (triethylsilyloxy)ketone (+)-46 (78 mg, 0.225 mmol) in 5 mL of THF at 0° C. was added 338 µL (0.338 mmol, 1.0 M in THF) of tetrabutylammonium fluoride dropwise via syringe. The reaction mixture was brought to rt and stirred for 5 h, after which the solvent was evaporated. The crude mixture was purified by column chromatography (20% EtOAc/hexanes) to give 48 mg of the desired hydroxy ketone 47 in quantitative yield: $^1$H NMR (CDCl$_3$) δ4.07 (m, 1H), 2.45 (t, J=8.8 , 1H), 2.05 (s, 3H), 0.82 (s, 3H); $^{13}$C NMR (CDCl$_3$) δ209.4, 68.5, 64.1, 52.6, 43.3, 39.4, 33.3, 31.4, 22.5, 21.6, 17.3, 15.1; $[α]_{25}{}^D$, IR, HRMS pending.

EXAMPLE 36

Acetoxy Ketone 48

To a solution of hydoxy ketone 47 (48 mg, 0.245 mmol) in 2.2 mL of CH$_2$Cl$_2$ at 0° C. was added DMAP (1 mg, 0.03 mmol), pyridine (44 μL, 0.539 mmol), and Ac$_2$O (46 μL, 0.489 mmol) sequentially and the resulting solution stirred for 5 h while warming to rt. Following concentration, the reaction mixture was passed through flash silica gel (10% EtOAc/hexanes) to afford acetoxy ketone 48 as a pale yellow oil (55 mg, 94%): $^1$H NMR (CDCl$_3$) δ5.08 (m, 1H), 2.42 (t, J=8.8 Hz, 1H), 2.02 (s, 3H), 1.94 (s, 3H), 0.73 (s, 3H); $^{13}$C NMR (CDCl$_3$) δ208.7, 170.4, 70.3, 63.6, 51.2, 43.1, 38.8, 31.3, 30.1, 22.5, 21.4, 21.0, 17.6, 14.5; $[α]^{25}{}_D$, IR, HRMS pending

EXAMPLE 37 t-Butyl 3-(Trimethylsilyloxy)-propyl Sulfone 50

To a solution of t-Butyl 3-hydroxypropyl sulfone[1] 49 (1.01 g, 5.60 mmol) in 25 mL of CH$_2$Cl$_2$ was added Et$_3$N (1.17 mL, 8.40 mmol) and then TMSCI (0.78 mL, 6.16 mL). The resulting solution was stirred for 1 h, cooled to 0° C., and quenched with saturated NaHCO$_3$ (5 mL). After warming, the reaction mixture was diluted with H$_2$O (10 mL), extracted with CH$_2$Cl$_2$ (3×15 mL), dried over Na$_2$SO$_4$, filtered, and concentrated to a red oil. Rapid column chromatography (25% EtOAc/hexanes) afforded the desired product 50 as a clear, colorless oil (0.75 g, 53% from 2-methyl-2-propanethiol[1]): 1H NMR (CDCl$_3$) δ3.71 (t, J=5.8 Hz, 2H), 3.00 (t, J=7.8 Hz, 2H), 2.07 (m, 2H), 1.4 (s, 9H), 0.09 (s, 9H); $^{13}$C NMR (CDCl$_3$) δ60.7, 58.8, 42.5, 23.8, 23.3, −0.63; IR (neat, cm$^{−1}$) 2959, 2906, 2875, 1301–1249, 1113; HRMS submitted

EXAMPLE 38

Acetoxy Sulfone 51

To a solution of ketone 48 (24 mg, 0.101 mmol) in 1 mL of CH$_2$Cl$_2$ at −78° C. was added 35 mg (0.138 mmol) of (trimethylsilyl)ether 50 in 0.350 mL of CH$_2$Cl$_2$. To this solution was added TMSOTf (0.019 mL, 0.105 mmol) via syringe and the resulting solution stirred at −78° C. for 1 h. Et$_3$SiH (0.017 mL, 0.105 mmol) was added via syringe and the reaction mixture brought to rt. After 4 h, the reaction was ceased by the addition of a saturated NaHCO$_3$ solution (1 mL). This mixture was diluted with H$_2$O (10 mL), extracted with CH$_2$Cl$_2$ (3×), dried over MgSO$_4$, filtered, concentrated, and passed through flash silica gel (25% EtOAc/hexanes) to afford the acetoxy sulfone 51 as a clear, colorless oil (21.0 mg, 52%): $^1$H NMR (CDCl$_3$) δ5.14 (m, 1H), 3.69 (dt, J=9.2, 6.0 Hz, 1H), 3.35 (dt, J=9.2, 6.0 Hz, 1H), 3.30 (m, 1H), 3.04 (t, J=7.8 Hz, 2H), 2.13 (m, 2H), 2.03 (s, 3H), 1.83 (m, 1H), 1.41 (s, 9H), 1.05 (d, J=6.0 Hz, 3H), 0.88 (s, 3H); $^{13}$C NMR (CDCl$_3$) δ170.8, 77.7, 71.1, 65.8, 58.8, 56.6, 50.9, 43.2, 41.8, 40.0, 30.6, 24.7, 23.4, 22.8, 21.7, 21.4, 18.1, 17.8, 13.7; $[α]_D{}^{25}$, IR, HRMS pending

EXAMPLE 39

C,D-Ring Ketone 52

To a solution of acetoxy sulfone 51 (18 mg, 0.045 mmol) in 2 mL of EtOH was added 10 M NaOH$_{(aq)}$(1 mL) dropwise. After stirring for 3 h, the reaction mixture was cooled to 0° C., diluted with Et$_2$O (1 mL), neutralized with 10% HCl$_{(aq)}$(1 mL), extracted with EtOAc (3×5 mL), the combined organics washed with brine, dried over MgSO$_4$, filtered, and concentrated to afford the crude alcohol (16 mg). This alcohol (16 mg) was then dissolved in 4 mL CH$_2$Cl$_2$, and to this solution was added celite (25 mg) and PDC (25 mg, 0.067 mmol). After stirring for 12 h, the suspension was passed through a short plug of celite and rinsed with CH$_2$Cl$_2$. The filtrate was then concentrated and passed through a short plug of flash silica gel (35% EtOAc/hexanes) to give the desired ketone 52 (16 mg) as a white solid in quantitative yield. $^1$H NMR (CDCl$_3$) δ3.69 (dt, J=9.2, 6.0 Hz, 1H), 3.36 (dt, J=9.2, 6.0 Hz, 1H), 3.29 (m, 1H), 3.01 (dt, J=7.7, 3.0 Hz, 2H), 2.45 (dd, J=11.2, 7.2 Hz, 1H), 1.41 (s, 9H) 1.08 (d, J=6.0 Hz, 3H), 0.64 (s, 3H); $^{13}$C NMR (CDCl$_3$) δ211.8, 77.5, 65.9, 61.4, 58.9, 56.7, 49.8, 42.9, 41.1, 39.0, 25.0, 24.1, 23.4, 21.7, 19.3, 18.2, 13.1; mp, $[α]_D{}^D$, IR, HRMS pending

EXAMPLE 40

20-Epi-22-oxa-26-sulfone Formulas X-1 and X-2

Racemic phosphine oxide (±)-A (51 mg, 0.087 mmol) was dissolved in 1 mL of THF and cooled to −78° C. under argon. To this solution was added 51 μL (0.086 mmol 1.69 M in cyclohexane/Et$_2$O) of PhLi dropwise via syringe. The deep orange solution was stirred for 30 min, at which time a cold solution of C,D-ring ketone 52 (31 mg, 0.082 mmol) in 0.7 mL of THF was added dropwise via cannula. The resulting solution was stirred at −78° C. in the dark for approximately 4 h and then quenched with 3 mL of a 2:1 (v:v) mixture of 2 N sodium potassium tartrate and 2 N potassium carbonate. Upon warming to rt, the reaction mixture was extracted with EtOAc (3×20 mL), dried over MgSO$_4$, filtered, concentrated and purified by silica gel column chromatography (20% EtOAc/1% NEt$_3$/hexanes) to afford 43 mg (72% based on 52) of the coupled product as a yellow oil. This oil was immediately dissolved in 10 mL of THF with 20 μL of NEt$_3$. To this solution was added 178 μL (0.178 mmol, 1.0 M in THF) of tetrabutylammonium fluoride dropwise via syringe. The reaction mixture was stirred for 16 h in the dark, after which the solvent was evaporated and the crude mixture purified by column chromatography (1% NEt$_3$/EtOAc) to give 21 mg (71%) of a mixture of two diastereomers Formula X-1 and Formula X-2. This diastereomeric mixture was purified by reversed-phase HPLC (C-18 semipreparative column, 40% MeCN/H$_2$O, 3 mL/min) giving Formula X-1 (1α, 3β, $t_R$ 70.7 min) and Formula X-2 (1β, 3α, $t_R$ 66.6 min): Formula X-1 (1α, 3β): $^1$H NMR (CDCl$_3$) δ6.38 (d, J=11.2 Hz, 1H), 6.00 (d, J=11.2 Hz, 1H), 5.32 (m, 1H), 4.99 (m, 1H), 4.46–4.40 (m, 1H), 4.26–4.19 (m, 1H), 3.70 (dt, J=9.2, 6.0 Hz, 1H), 3.34 (dt, J=9.2, 6.0 Hz, 1H), 3.29 (m, 1H), 3.03 (m, 2H), 2.83 (dd, J=13.2, 4.4 Hz, 1H), 2.60 (dd, J=13.2, 3.6 Hz, 1H), 2.29 (dd, J=13.4, 6.4 Hz, 1H), 1.41(s, 9H) 1.08 (d, J=5.6 Hz, 3H), 0.55 (s, 3H); $^{13}$C NMR, UV, $[α]^{25}{}_D$−50.8 (c 4.4, CHCl$_3$); Formula X-2 (1β, 3α): $^1$H NMR (CDCl$_3$) δ6.39 (d, J=11.6 Hz, 1H), 5.99 (d, J=11.2 Hz, 1H), 5.31 (m, 1H), 5.00 (m, 1H), 4.47–4.41 (m, 1H), 4.26–4.19 (m, 1H), 3.71 (dt, J=9.2, 6.0 Hz, 1H), 3.35 (dt, J=9.2, 6.0 Hz, 1H), 3.29 (m, 1H), 3.04 (m, 2H), 2.83 (dd, J=13.2, 4.0 Hz, 1H), 2.61 (dd, J=13.2, 4.0 Hz, 1H), 2.30 (dd, J=13.0, 7.6 Hz, 1H), 1.41 (s, 9H) 1.08 (d, J=5.6 Hz, 3H), 0.55 (s, 3H); $^{13}$C NMR, UV, $[α]^{25}{}_D$−36.2 (c 3.0, CHCl$_3$).

Via synthesis procedures similar to those set forth in the examples herein, it is possible to prepare related 23-oxa-25-sulfones and 20-epi-22-oxa-sulfones. Such compounds have the generic structures shown in Formulas XI and XII as follows:

Formula XI

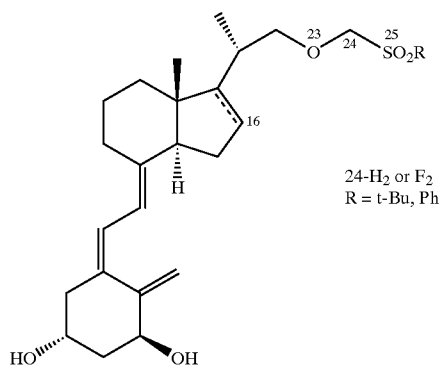

23-oxa-25-sulfones

24-H$_2$ or F$_2$
R = t-Bu, Ph

Formula XII

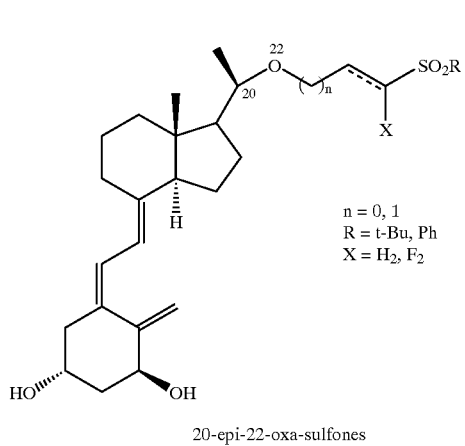

20-epi-22-oxa-sulfones n = 0, 1
R = t-Bu, Ph
X = H$_2$, F$_2$

Via conventional organic synthesis procedures starting from materials described herein, it is also possible to prepare related 16-ene-alkenylsulfones and 16-ene-alkynylsulfones. Such compounds have the generic structure shown in Formula XIII as follows:

Formula XIII

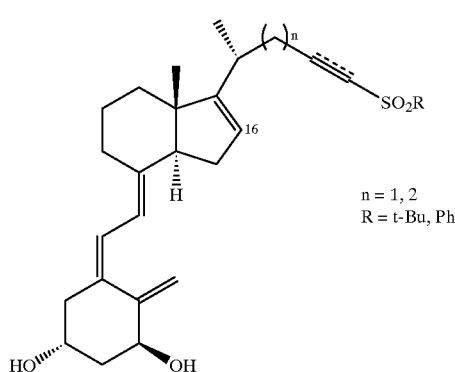

16-ene-alkenylsulfones and 16-ene-alkynylsulfones n = 1, 2
R = t-Bu, Ph

Scheme 10
Synthesis of 20-Epi-22-oxi-26-p-methoxyphenyl
Sulfone Analogs 15a and 15b:

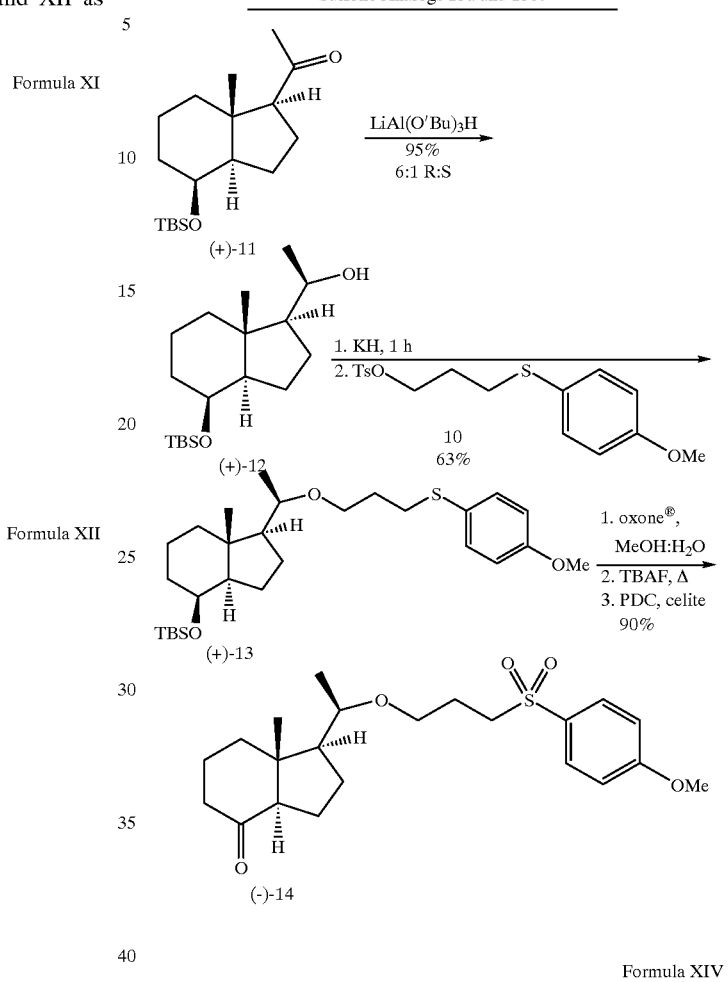

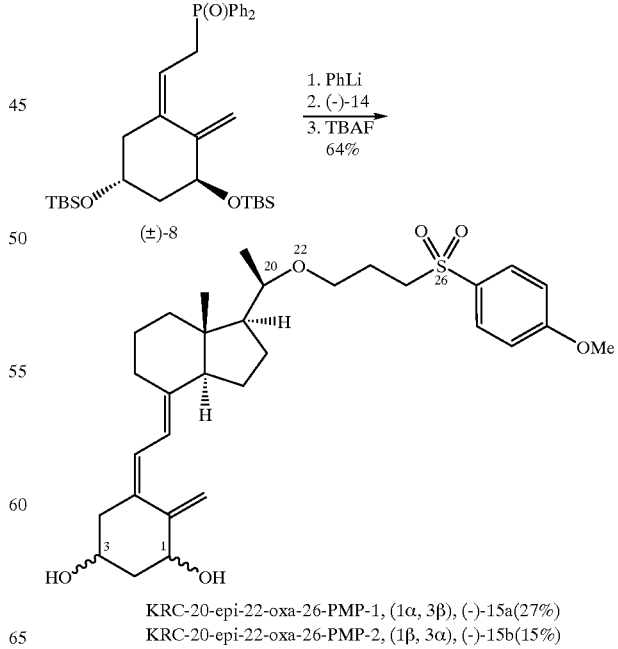

KRC-20-epi-22-oxa-26-PMP-1, (1α, 3β), (-)-15a(27%)
KRC-20-epi-22-oxa-26-PMP-2, (1β, 3α), (-)-15b(15%)

EXAMPLE 41

4-[(Methoxy)phenyl]-3-tosyloxypropyl Sulfide 10

To a solution of NaOH (0.572 g, 14.3 mmol) in EtOH (12 mL) at 0° C. was added dropwise via syringe 4-methoxythiophenol (1.75 mL, 14.3 mmol) over 2 min. The resulting solution was warmed to rt and stirred for 30 min. Upon dropwise addition of 3-chloro-1-propanol (1.19 mL, 14.3 mmol), the reaction mixture was heated to reflux and stirred overnight. The resulting suspension was filtered to remove NaCl, which was rinsed thoroughly with $CH_2Cl_2$. The filtrate was neutralized with 1 M HCl (12 mL), diluted with $H_2O$ (20 mL), extracted with $CH_2Cl_2$ (3×20 mL), washed with $H_2O$, dried over $Na_2SO_4$, filtered, and concentrated to a pale yellow oil which solidified on standing.

A portion of this pale yellow solid (613 mg, 2.66 mmol) was dissolved in $CH_2Cl_2$ (17 mL) and cooled to 0° C. To this solution was added DMAP (390 mg, 3.19 mmol) and TsCl (558 mg, 2.93 mmol), and the resulting solution was allowed to stir with gradual warming to rt overnight. The reaction mixture was quenched with 10% $HCl_{(aq)}$ (5 mL), partitioned between $CH_2Cl_2$ and $H_2O$, extracted with $CH_2Cl_2$ (3×20 mL), dried over $Na_2SO_4$, filtered, concentrated, and purified by column chromatography (30–50% EtOAc/hexanes) to give the desired tosylate (448 mg, 44%) as a clear oil: $^1$H NMR (CDCl$_3$) δ7.77 (dt, J=8.4, 1.6 Hz, 2H), 7.34 (m, 2H), 7.27 (dt, J=9.0, 2.2 Hz, 2H), 6.82 (dt, J=9.0, 2.2 Hz, 2H), 4.13 (t, J=6.0 Hz, 2H), 3.78 (s, 3H), 2.80 (t, J=7.0 Hz, 2H), 2.44 (s, 3H), 1.86 (m, 2H); $^{13}$C NMR (CDCl$_3$) δ159.10, 144.77, 133.58, 132.82, 129.81, 127.81, 125.15, 114.57, 68.61, 55.26, 31.62, 28.35, 21.59; IR (neat) 3063, 2957, 2834, 1594, 1571, 1494, 1462, 1441, 1359, 1284, 1244, 1187, 1174, 1096, 1030; HRMS: calcd for $C_{17}H_{20}O_4S_2$ 352.0803, found 352.0804.

EXAMPLE 42

R-Alcohol (+)-12

To a stirred solution of (t-butyldimethylsilyloxy)ketone (+)-11$^1$ (803 mg, 2.59 mmol) in THF (50 mL) at −78° C. was added lithium tri-tert-butoxyaluminohydride (7.76 mL, 1.0 M in THF) dropwise via syringe. The reaction mixture was brought to rt slowly overnight. The reaction was quenched with a saturated aqueous $NH_4Cl$ solution (15 mL) and the resulting mixture was extracted with EtOAc (3×25 mL), dried with brine and $MgSO_4$, filtered, and concentrated. The crude mixture was purified on short path silica gel (5–10% EtOAc/hexanes) to give 658 mg (81%) of the desired R-alcohol (+)-12 and 113 mg (14%) of the S-alcohol, both having spectroscopic and physical characteristics analogous to those reported previously.$^2$

EXAMPLE 43

8β-[(t-Butyldimethylsilyl)oxy]-20-epi-22-oxa-26-p-methoxyphenyl Sulfone (+)-13

Potassium hydride (63 mg of a 35 wt. % dispersion in mineral oil—approximately 22 mg, 0.54 mmol dry weight) was rinsed and dried according to methods described by Brown.$^3$ To a suspension of the resulting dry KH in THF (1.0 mL) was added a solution of alcohol (+)-12 (50 mg, 0.16 mmol) in THF (2.2 mL) dropwise via syringe. The resulting yellow solution was stirred for 1 h. Then tosylate 10 (123 mg, 0.32 mmol) in THF (0.88 mL) was added via syringe. After 3 h, the reaction was cautiously diluted with EtOAc and $H_2O$, and extracted with EtOAc (3×15 mL). The combined organic phases were dried over $MgSO_4$, filtered, concentrated and purified on flash silica gel (2–5% EtOAc/hexanes) to afford 50 mg (63%) of the desired ether (+)-13 with 11 mg (22%) of recovered alcohol (+)-12: $[\alpha]_D^{25}$+1.63 (c 3.0, CHCl$_3$); $^1$H NMR (CDCl$_3$) δ7.34 (dt, J=9.0, 2.2 Hz, 2H), 6.83 (dt, J=9.0, 2.2 Hz, 2H), 4.00 (m, 1H), 3.79 (s, 3H), 3.62 (dt, J=9.0, 6.0 Hz, 1H), 3.31–3.22 (m, 2H), 2.91 (t, J=7.2 Hz, 2H), 2.02 (dt, J=12.4, 2.8 Hz, 1H), 1.85–1.05 (m, 13H), 1.04 (d, J=6.0, 3H), 0.93 (s, 3H), 0.89 (s, 9H), 0.01 (s, 3H), 0.01 (s, 3H); $^{13}$C NMR (CDCl$_3$) δ158.75, 133.02 126.53, 114.47, 77.71, 69.29, 66.24, 57.08, 55.29, 52.61, 42.00, 40.56, 34.59, 32.94, 29.92, 25.80, 24.95, 23.20, 18.22, 18.01, 17.63, 14.46, −4.79, −5.19; IR (neat) 3002, 2949, 2928, 2855, 1593, 1494, 1471, 1462, 1454, 1284, 1245, 1168, 1104, 1078, 1034, 1019; HRMS: calcd for $C_{28}H_{48}O_3SSi$ 492.3093, found 492.3093.

EXAMPLE 44

C,D-Ring Ketone (−)-14

Oxone® (20% aqueous solution: 68 mg, 0.11 mmol in 275 μL $H_2o$) was added dropwise to a stirred solution of ether (+)-13 in MeOH (1.0 mL). The resulting solution was stirred for 2 d, with additional oxone® solution being added to consume starting material. Upon dilution with $H_2O$ and extraction with CHCl$_3$, the combined organics were dried, filtered and concentrated to give a crude mixture of sulfones (C8-OTBS : C8-OH), which was immediately dissolved in THF (3.5 mL) and treated with TBAF (400 μL, 1.0 M in THF). The resulting solution was stirred at reflux for 2 d, with additional TBAF solution being added to consume starting material. The reaction mixture was cooled to rt, diluted with EtOAc and $H_2O$ (10 mL each), extracted with EtOAc (3×10 mL), dried, filtered, and concentrated to give crude hydroxy sulfone which was carried forward.

To crude hydroxy sulfone in $CH_2C_2$ (8 mL) was added celite (57 mg) and PDC (57 mg, 0.15 mmol) and the resulting brown suspension was stirred overnight. Upon filtration through celite®, the reaction mixture was concentrated and passed through a short pad of flash silica gel (40% EtOAc/hexanes) to afford the desired C,D-ring ketone (−)-14 as a pale yellow oil (37 mg, 90% from (+)-13): $[\alpha]^{25}_D$ −40.8 (c 3.0, CHCl$_3$); $^1$H NMR (CDCl$_3$) δ7.80 (dt, J=9.2, 2.2 Hz, 2H), 7.00 (dt, J=9.2, 2.2 Hz, 2H), 3.86 (s, 3H), 3.54 (dt, J=9.2, 6.2 Hz, 1H), 3.28–3.06 (m, 5H), 2.45–2.38 (dd, J=11.2, 7.6 Hz, 1H), 2.28–1.07 (m, 12H), 1.01 (d, J=6.0, 3H), 0.57 (s, 3H); $^{13}$C NMR (CDCl$_3$) δ211.76, 163.64, 130.52, 130.09, 114.37, 77.41, 65.38, 61.31, 56.59, 55.63, 53.97, 49.68, 41.01, 38.85, 24.91, 24.03, 23.92, 19.25, 18.09, 12.98; IR (neat) 2961, 2874, 1708, 1595, 1578, 1498, 1317, 1298, 1260, 1226, 1140, 1108, 1089, 1023; HRMS: calcd for $C_{22}H_{32}O_5S$ 408.1970, found 408.1976.

EXAMPLE 45

20-Epi-22-oxa-26-p-methoxyphenyl Sulfone Analogs 15a and 15b

Racemic phosphine oxide (±)-8 (78 mg, 0.13 mmol) was dissolved in 1.3 mL of THF and cooled to −78° C. under argon. To this solution was added 88 μL (0.13 mmol, 1.5 M in cyclohexane/Et$_2$O) of PhLi dropwise via syringe. The deep orange solution was stirred for 30 min, at which time a cold (−78° C.) solution of C,D-ring ketone (−)-14 (36 mg, 0.087 mmol) in 1.2 mL of THF was added dropwise via cannula. The resulting solution was stirred in the dark at −78° C. for approximately 3 h, and for an additional 1 h at −60° C. The reaction mixture was quenched with 3 mL of a 2:1 (v:v) mixture of 2 N sodium potassium tartrate and 2 N potassium carbonate. Upon warming to rt, the reaction mixture was diluted with H$_2$O, extracted with EtOAc (4×20 mL), dried over MgSO$_4$, filtered, concentrated and purified by silica gel column chromatography (20% EtOAc/hexanes-<0.1% NEt$_3$) to afford 40 mg (64% based on (−)-14) of the coupled product as a yellow oil.

This oil was immediately dissolved in THF (10 mL) with 10 μL of NEt$_3$. To this solution was added 170 μL (0.17 mmol, 1.0 M in THF) of tetrabutylammonium fluoride dropwise via syringe. The reaction mixture was stirred for 16 h in the dark, after which the solvent was evaporated and the crude mixture purified by column chromatography (1% NEt$_3$/EtOAc) to give 27 mg (90%) of a mixture of two diastereomers 15a and 15b. This diastereomeric mixture was purified by reversed-phase HPLC (C-18 semipreparative column, 43% MeCN/H$_2$O, 3 mL/min) giving 15a (27%, t$_R$ 93.8 min) and 15b (15%, t$_R$ 88.9 min): 15a (1α, 3β): [α]$_D^{25}$ −44.6 (c 2.5, CHCl$_3$); $^1$H NMR (CDCl$_3$) δ7.81 (dt, J=8.8, 2.0 Hz, 2H), 7.01 (dt, J=8.8, 2.0 Hz, 2H), 6.37 (d, J=11 Hz, 1H), 5.98 (d,, J=11 Hz, 1H), 5.31 (m, 1H), 4.98 (m, 1H), 4.45–4.38 (m, 1H), 4.26–4.19 (m, 1H), 3.54 (dt, J=9.2, 6.2 Hz, 1H), 3.28–3.06 (m, 5H), 2.85–2.76 (dd, J=12.2, 3.0 Hz, 1H), 2.63–2.54 (dd, J=12.2, 3.0 Hz, 1H), 2.34–2.26 (dd, J=13.3, 6.8 Hz, 1H), 2.06–1.04 (m, 19H), 1.01 (d, J=6.0, 3H), 0.49 (s, 3H); $^{13}$C NMR (CDCl$_3$) δ163.65, 147.61, 142.86, 132.98, 130.63, 130.17, 124.88, 117.02, 114.40, 111.73, 78.19, 70.77, 66.80, 65.45, 56.66, 55.75, 55.67, 54.12, 45.71, 45.21, 42.84, 40.34, 29.06, 25.04, 24.01, 23.49, 22.40, 18.22, 12.63; IR (neat) 3706–3115 (br), 3019, 2945, 2872, 1644, 1595, 1578, 1497, 1443, 1413, 1372, 1317, 1296, 1261, 1219, 1165, 1139, 1109, 1088, 1057, 1027; UV (MeOH) λ$_{max}$ 240 (ϵ20,102), 264 nm (ϵ13,165); HRMS: calcd for C$_{31}$H$_{44}$O$_6$S 544.2859, found 544.2857. 15b (1β, 3α): [α]$_D^{25}$ −43.0 (c 4.1, CHCl$_3$); $^1$H NMR (CDCl$_3$) δ7.81 (dt, J=8.8, 2.0 Hz, 2H), 7.01 (dt, J=8.8, 2.0 Hz, 2H), 6.38 (d, J=11.2 Hz, 1H), 5.98 (d, J=11.2 Hz, 1H), 5.30 (m, 1H), 4.99 (m, 1H), 4.46–4.40 (m, 1H), 4.26–4.18 (m, 1H), 3.55 (dt, J=9.2, 6.2 Hz, 1H), 3.28–3.06 (m, 5H), 2.85–2.76 (dd, J=12.2, 3.0 Hz, 1H), 2.63–2.54 (dd, J=12.2, 3.0 Hz, 1H), 2.34–2.26 (dd, J=13.3, 6.8 Hz, 1H), 2.06–1.04 (m, 19H), 1.01 (d, J=6.0, 3H), 0.49 (s, 3H); $^{13}$C NMR (CDCl$_3$) δ163.65, 147.29, 142.93, 132.82, 130.65, 130.18, 124.91, 117.01, 114.41, 112.45, 78.19, 71.29, 66.78, 65.46, 56.66, 55.75, 55.67, 54.12, 45.72, 45.44, 42.82, 40.33, 29.03, 25.04, 24.01, 23.48, 22.43, 18.22, 12.65; IR (neat) 3686–3076 (br), 2947, 2926, 2871, 1595, 1578, 1498, 1458, 1438, 1372, 1317, 1296, 1260, 1220, 3.: 1139, 1109, 1089, 1053, 1025; UV (MeOH) λ$_{max}$ 240 (ϵ17,201), 261 nm (ϵ10,346); HRMS: calcd for C$_{31}$H$_{44}$O$_6$S 544.2859, found 544.2857.

EXAMPLE 46

20-Epi-22-oxa-25-difluoro-26-tert-butyl Sulfone Analogs 25a and 25b

Formula XV

KRC-20-epi-22-oxa-25-F$_2$-26-SO$_2$-1, (1α, 3β), 25a (31%)
KRC-20-epi-22-oxa-25-F$_2$-26-SO$_2$-2, (1β, 3α), 25b (9%)

20-Epi-22-oxa-25-difluoro-26-tert-butyl Sulfone Analogs 25a and 25b

Racemic phosphine oxide (±)-8 (70 mg, 0.12 mmol) was dissolved in 1.2 ML of THF and cooled to −78° C. under argon. To this solution was added 80 μL of n-BuLi (0.12 mmol, 1.53 M in hexanes) dropwise via syringe. The deep red solution was stirred for 1 h, at which time a cold (−78° C.) solution of C,D-ring ketone (−)-24 (24 mg, 0.061 mmol) in 1.0 mL of THF was added dropwise via cannula. The resulting solution was stirred at −78° C. in the dark for approximately 3 h, then slowly warmed to 40° C. over 2 h. The reaction mixture was quenched with $H_2O$ (1 mL), warmed to rt, extracted with $Et_2O$ (3×10 mL), washed with brine, dried over $MgSO_4$, filtered, concentrated and purified by silica gel column chromatography (5–40% EtOAc/hexanes) to afford 43 mg of the coupled product as a clear oil.

This oil was immediately dissolved in 3.0 mL of EtOH. To this solution was added 100 μL of an aqueous HF solution (49% wt) dropwise via syringe. The reaction mixture was stirred for 4 h in the dark, which, after general aqueous workup and column chromatography (75% EtOAc/hexanes), yielded 30 mg [93% from (−)-24] of a mixture of diastereomers 25a and 25b. This diastereomeric mixture was purified by reversed-phase HPLC (C-18 semipreparative column, 49% $MeCN/H_2O$, 3 ml/min) giving 10 mg (31%) of 25a (1α, 3β, $t_R$ 111 min) and 3.0 mg (9%) of 25b (1β, 3α, $t_R$ 105 min): 25a (1α, 3β): $^1H$ NMR (CDCl$_3$) δ6.38 (d, J=11 Hz, 1H), 5.99 (d, J=11 Hz, 1H), 5.32 (m, 1H), 4.99 (m, 1H), 4.45–4.39 (m, 1H), 4.264.17 (m, 1H), 3.84 (m, 1H), 3.51 (m, 1H), 3.31 (m, 1H), 2.82 (dd, J=16, 4.3 Hz, 1H 1H), 2.60 (m, 3H), 2.31 (dd, J=18, 8.8 Hz, 1H), 1.52 (s, 9H) 1.09 (d, J=5.6 Hz, 3H), 0.54 (s, 3H); $^{13}C$ NMR (CDCl$_3$) δ147.62, 143.12, 132.82, 124.98, 116.94, 111.71, 78.56, 70.80, 66.83, 60.05, 56.58, 55.82, 45.76, 45.23, 42.84, 40.17, 31.47, 29.12, 25.09, 24.14, 23.52, 22.42, 18.12, 12.53; HRMS: calcd for $C_2H_{44}F_2O_5S$ 530.2878, found 530.2877; 25b (1β, 3α): $^1H$ NMR (CDCl$_3$) δ6.40 (d, J=12 Hz, 1H), 5.98 (d, J=12 Hz, 1H), 5.31 (m, 1H), 5.00 (m, 1H), 4.44 (m, 1H), 4.23 (m, 1H), 3.85 (m, 1H), 3.52 (m, 1H), 3.31 (m, 1H), 2.82 (dd, J=16, 4.3 Hz, 1H 1H), 2.59 (m, 3H), 2.29 (dd, J=18, 8.8 Hz, 1H), 1.52 (s, 9H) 1.09 (d, J=6.0 Hz, 3H), 0.54 (s, 3H); $^{13}C$ NMR (CDCl$_3$) δ147.28, 143.18, 132.68, 125.00, 116.94, 112.49, 78.57, 71.35, 66.80, 60.06, 56.58, 55.82, 45.78, 45.48, 42.82, 40.16, 31.48, 29.10, 25.09, 24.14, 23.52, 22.45, 18.13, 12.55; HRMS: calcd for $C_{28}H_{44}F_2O_5S$ 530.2878, found 530.2877; $^{19}F$ NMR, UV, $[\alpha]_D^{25}$, IR pending.

Through the use of similar methods, 27-t-butyl sulfone and 26-methyl sulfone analogs can be synthesized as shown in Schemes 11 and 12.

[1] Fernandez, B.; Perez, J. A. M.; Granja, J. R.; Castedo, L.; Mourino, A. *J. Org. Chem.* 1992, 57, 3173–3178.

[2] Posner, G. H.; White, Dolan, P.; Kensler, T. W.; Yukihiro, S.; Guggino, S. E. *Biorg. Med. Chem. Let.* 1994, 4, 2919–2924.

[3] Brown, C. A. *J. Org. Chem.* 1974, 39, 3913–3918.

Scheme 11
Synthesis of 27-t-Butyl Sulfone Analogs

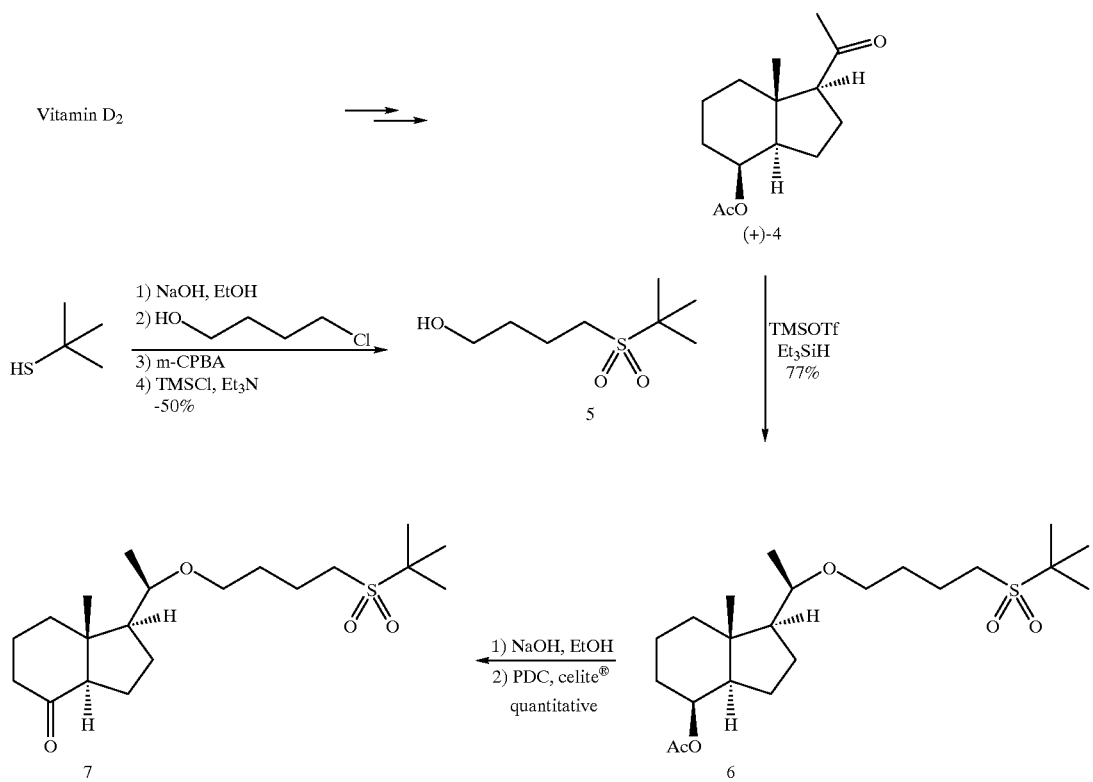

Formula XVI
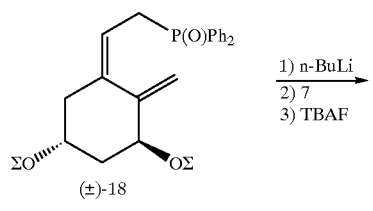
Formula XVII
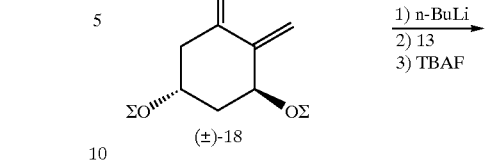
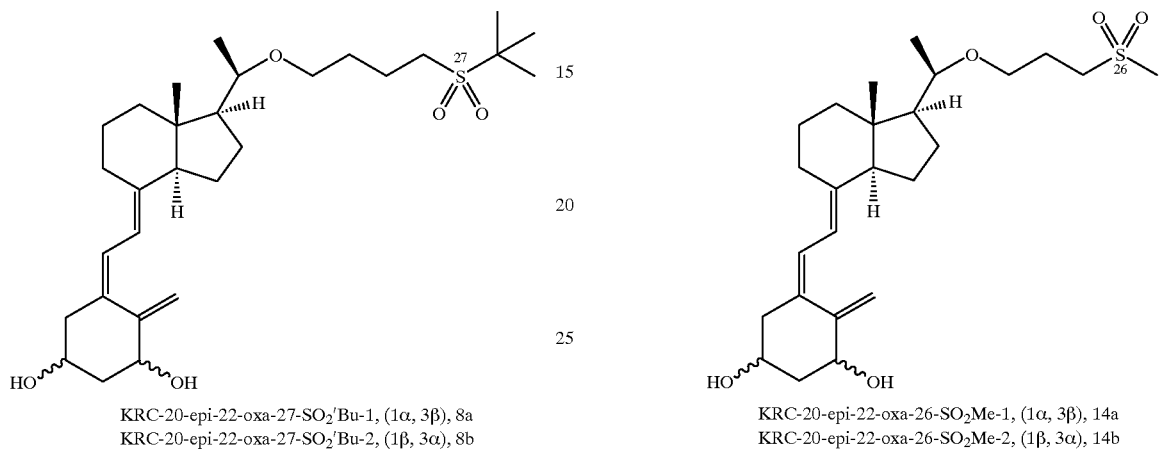
KRC-20-epi-22-oxa-27-SO$_2$$^t$Bu-1, (1α, 3β), 8a
KRC-20-epi-22-oxa-27-SO$_2$$^t$Bu-2, (1β, 3α), 8b
KRC-20-epi-22-oxa-26-SO$_2$Me-1, (1α, 3β), 14a
KRC-20-epi-22-oxa-26-SO$_2$Me-2, (1β, 3α), 14b
Scheme 12
Synthesis of 26-Methyl Sulfone Analogs
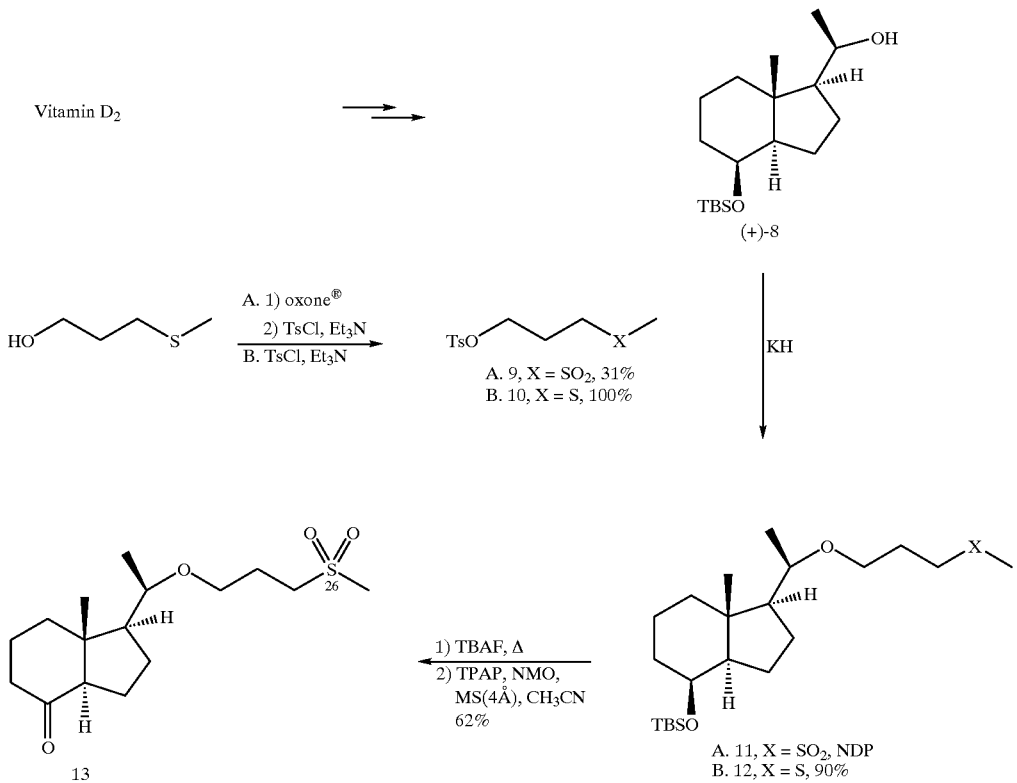

EXAMPLE 47

22E, 24E-diene sulfones can be synthesized by the method shown in Scheme 13. Analogous compounds in which the t-butyl group is replaced by an alternate lower alkyl group or by an unsubstituted phenyl or a phenyl substituted with a lower alkyl or alkoxy can be made with modifications which will be evident to persons of skill in the art.

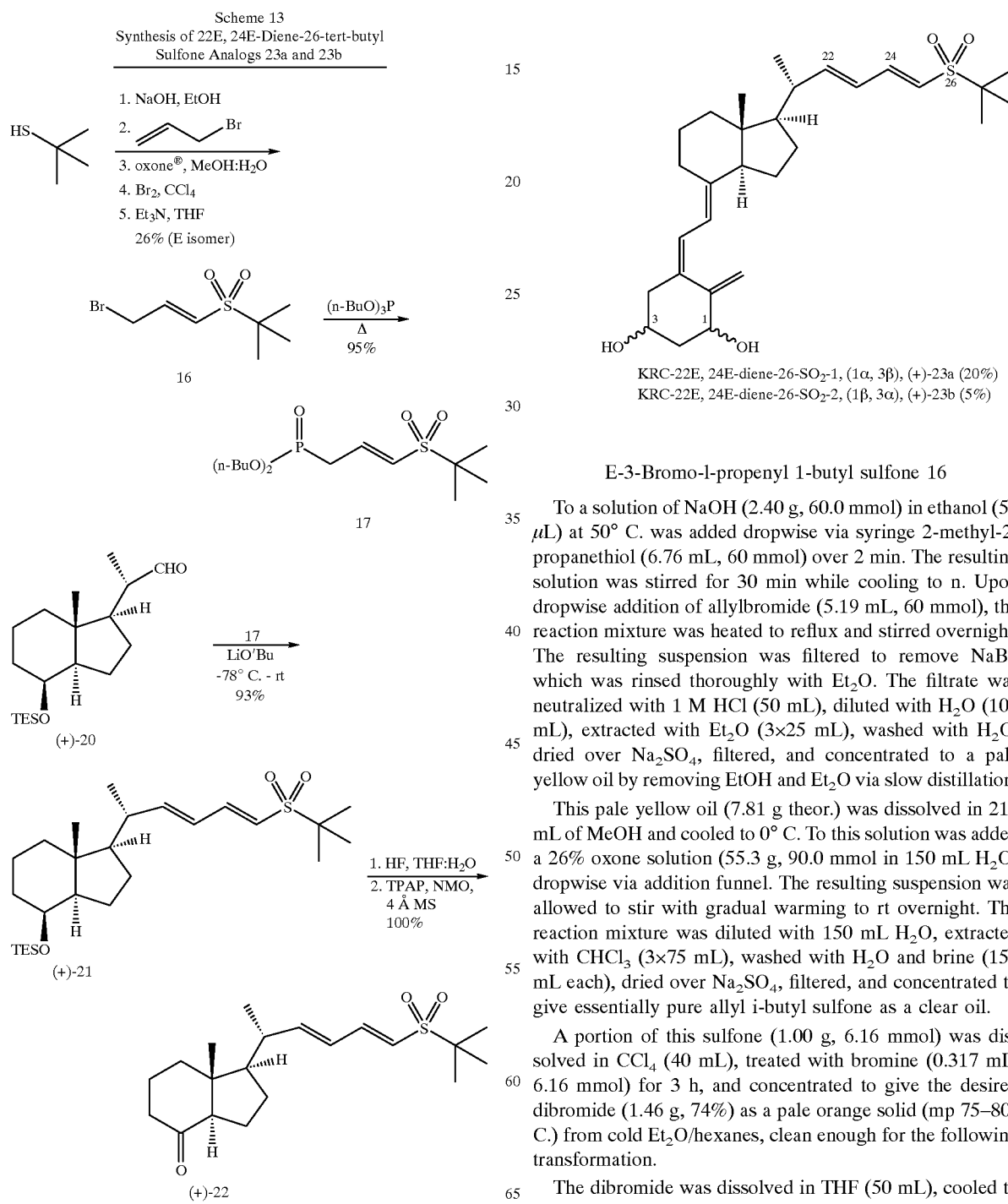

E-3-Bromo-l-propenyl 1-butyl sulfone 16

To a solution of NaOH (2.40 g, 60.0 mmol) in ethanol (50 μL) at 50° C. was added dropwise via syringe 2-methyl-2-propanethiol (6.76 mL, 60 mmol) over 2 min. The resulting solution was stirred for 30 min while cooling to n. Upon dropwise addition of allylbromide (5.19 mL, 60 mmol), the reaction mixture was heated to reflux and stirred overnight. The resulting suspension was filtered to remove NaBr, which was rinsed thoroughly with $Et_2O$. The filtrate was neutralized with 1 M HCl (50 mL), diluted with $H_2O$ (100 mL), extracted with $Et_2O$ (3×25 mL), washed with $H_2O$, dried over $Na_2SO_4$, filtered, and concentrated to a pale yellow oil by removing EtOH and $Et_2O$ via slow distillation.

This pale yellow oil (7.81 g theor.) was dissolved in 215 mL of MeOH and cooled to 0° C. To this solution was added a 26% oxone solution (55.3 g, 90.0 mmol in 150 mL $H_2O$) dropwise via addition funnel. The resulting suspension was allowed to stir with gradual warming to rt overnight. The reaction mixture was diluted with 150 mL $H_2O$, extracted with $CHCl_3$ (3×75 mL), washed with $H_2O$ and brine (150 mL each), dried over $Na_2SO_4$, filtered, and concentrated to give essentially pure allyl i-butyl sulfone as a clear oil.

A portion of this sulfone (1.00 g, 6.16 mmol) was dissolved in $CCl_4$ (40 mL), treated with bromine (0.317 mL, 6.16 mmol) for 3 h, and concentrated to give the desired dibromide (1.46 g, 74%) as a pale orange solid (mp 75–80° C.) from cold $Et_2O$/hexanes, clean enough for the following transformation.

The dibromide was dissolved in THF (50 mL), cooled to 0° C., and treated with $Et_3N$ (0.945 mL, 6.78 mmol) overnight, while gradually warming to rt. The reaction mixture was neutralized with dilute HCl, diluted with H$_2$O, extracted with Et$_2$O (3×25 mL), dried over Na$_2$SO$_4$, filtered, concentrated, and purified by column chromatography (10–20% Et$_2$O/pentane) to give 16 (385 mg, 26% two steps) as white crystals: mp 60–62° C.; $^1$H NMR (CDCl$_3$) δ7.00 (dt, J=15, 6.8 Hz, 1H), 6.55 (dt, J=15, 1.2 Hz, 1H), 4.07 (dd, J=6.8, 1.2 Hz, 2H), 1.38 (s, 9H); $^{13}$C NMR (CDCl$_3$) δ143.82, 127.63, 58.94, 27.36, 23.23; IR (neat) 3068, 3053, 2976, 1636, 1305, 1275, 1109, 982; Anal. Calcd for C$_7$H$_{13}$BrO$_2$S: C, 34.86; H, 5.43. Found: C, 34.98; H, 5.32.

Di-n-butylphosphonate 17

A stirred solution of tri-n-butyl phosphite (5 mL) and sulfone 16 (370 mg, 1.53 mmol) was heated to 130° C. for 12 h, cooled to rt, concentrated and purified on silica gel (75% EtOAc/hexanes) to give 519 mg (95%) of 16 as a clear oil: $^1$H NMR (CDCl$_3$) δ7.00 (dt, J=15, 8.0 Hz, 1H), 6.38 (ddt, J=15, 4.6, 1.2 Hz, 1H), 4.03–3.92 (m, 4H), 2.76 (ddd, J=25, 8.0, 1.2 Hz), 1.62–1.53 (m, 4H), 1.38–1.30 (m, 4H); 1.29 (6H), 0.85 (t, J=7.2 Hz, 6H); $^{13}$C NMR (CDCl$_3$) δ140.23 (d, J=11Hz), 128.24 (d, J=14 Hz), 66.18 (d, J=6.8 Hz), 58.69, 32.47 (d, J=6.1 Hz), 29.97 (d, J=140 Hz), 27.36, 23.18, 13.52; IR (neat) 2961, 2935, 2874, 1633, 1477, 1464, 1289, 1246, 1114, 1024, 983; Anal. Calcd for C$_{15}$H$_{31}$O$_5$PS: C, 50.83; H, 8.82; S, 9.05. Found: C, 50.64; H, 8.65; S, 8.91.

8β-[(Triethylsilyl)oxy]-22E,24E-diene 26-tert-Butyl Sulfone (+)-21

A solution of lithium tert-butoxide (1.0 M in THF, 0.491 mL, 0.491 mmol) was added via syringe to a cold (−78° C.) solution of phosphonate 17 (175 mg, 0.493 mmol) in THF (1.0 mL). The mixture was warmed slightly to effect solution, then returned to −78° C. The resulting yellow solution was delivered via cannula to a stirred solution of aldehyde (+)-20 (64.0 mg, 0.197 mmol) in THF (1.5 mL) at rt. After 10 min. the solvent was removed and the residual brown oil was flash chromatographed (8% EtOAc/hexanes) to give 86 mg of (+)-21 (93%) as a moist solid: $[\alpha]_D^{25}$ +77.9 (c 4.0, CHCl$_3$); $^1$H NMR (CDCl$_3$) δ7.11 (m, 1H), 6.14 (t, J=15 Hz, 1H), 6.09 (m, 2H), 4.02 (m, 1H), 2.27–2.17 (m, 1H), 1.96–1.89 (m, 1H), 1.89–1.74 (qt, J=13, 3.8 Hz, 1H), 1.35 (s, 9H), 1.04 (d, J=6.8 Hz, 3H), 0.93 (t, J=8.0 Hz, 9H), 0.93 (s, 3H), 0.54 (q, J=8.0 Hz, 6H); $^{13}$C NMR (CDCl$_3$) δ153.66, 147.16, 123.71, 120.43, 69.20, 58.55, 55.83, 52.87, 42.38, 40.61, 40.10, 34.52, 27.39, 23.32, 22.94, 19.35, 17.62, 13.75, 6.90, 4.88; IR (neat) 2950, 2935, 2873, 1638, 1458, 1300, 31134, 1018, 1004; HRMS: calcd for C$_{26}$H$_{48}$O$_3$SSi: 468.3093, found 468.3094.

C,D-Ring Ketone (+)-22

An aqueous solution of HF (0.500 mL, 10% wt) was added dropwise to a stirred solution of (+)-21 in H$_2$O:THF (1.00 mL H$_2$O: few drops of THF to effect solution) and the resulting solution stirred at rt for 2 d (two additional 0.500 mL portions of 10% HF$_{(aq)}$ were added over this period to consume starting material). The reaction mixture was then carefully neutralized (sat. NaHCO$_3$), diluted with H$_2$O, and extracted with CH$_2$Cl$_2$ (3×10 mL). The combined organics were dried (Na$_2$SO$_4$), filtered and concentrated to give the desired hydroxy sulfide as a white solid.

To crude hydroxy sulfide in CH$_2$Cl$_2$ (3 mL) was added 4-methymorpholine N-oxide (NMO, 58.0 mg, 0.492 mmol) and powdered molecular sieves (4A), followed by tetrapropylammonium perruthenate (TPAP, 4.30 mg, 0.0123 mmol). After stirring for 15 min, the reaction mixture was filtered, concentrated and passed through a short pad of flash silica gel (20% EtOAc/hexanes) to afford the desired keto sulfone (+)-22 as a white foam (79 mg, quantitative from (+)-21): $^1$H NMR (CDCl$_3$) δ 7.08 (dd, J=15, 10 Hz 1H), 6.15 (t, J=15 Hz, 1H), 6.08 (m, 2H), 2.43 (m, 1H), 2.29–2.15 (m, 3H), 1.32 (s, 9H), 1.08 (d, J 6.4 Hz, 3H), 0.63(s, 3H); $^{13}$C NMR (CDCl$_3$) δ211.39, 152.05, 146.59, 124.38, 121.21, 61.62, 58.57, 55.62, 49.85, 40.86, 40.12, 38.71, 27.46, 23.94, 23.30, 19.61, 19.06, 12.72; IR (neat) 2955, 2934, 2872, 1708, 1638, 1587, 1461, 1296, 1278, 11 11, 1001, 824; HRMS: calcd for C$_2$O$_{32}$O$_3$S: 352.2072, found 352.2066.

22E,24EDiene26-tert-butyl Sulfone Analogs 23a and 23b

Racemic phosphine oxide (±)-8 (78.0 mg, 0.134 mmol) was dissolved in 1.34 mL of THF and cooled to −78° C. under argon. To this solution was added 97.0 μL of PhLi (0.134 mmol, 1.38 M in cyclohexane/Et$_2$O) dropwise via syringe. The deep orange solution was stirred for 30 min, at which time a cold solution of C,D-ring ketone (+)-22 (31.0 mg, 0.0880 mmol) in 1.00 mL of THF was added dropwise via cannula. The resulting solution was stirred in the dark at −78° C. for approximately 4 h, then slowly warmed to −40° C. over 2 h. The reaction mixture was quenched with 3 ml of a 2:1 (v:v) mixture of 2 N sodium potassium tartrate and 2 N potassium carbonate. Upon warming to rt, the reaction mixture was diluted with H$_2$O, extracted with EtOAc (4×20 mL), dried over MgSO$_4$, filtered, concentrated and purified by silica gel column chromatography (10–50% EtOAc/hexanes-<0.1 % Et$_3$N) to afford 33 mg (90% based on (+)-22) of the coupled product as a yellow oil.

This oil was immediately dissolved in 1.50 mL of EtOH, cooled to 0° C., and treated with HF (0.100 mL, 49% aqueous). This solution was slowly warmed to rt and treated with additional HF (0.100 mL) to complete the deprotection. After aqueous work-up the resulting white film was flash chromatographed (1% NEt/EtOAc) to afford 17.3 mg (77% for deprotection) of a mixture of diastereomers 23a and 23b. This diastereomeric mixture was purified by reversed-phase HPLC (C-8 semipreparative column, 46% MeCN/H$_2$O, 3 mL/min) giving 8.8 mg of 23a (20%, t$_R$ 15 min) and 2.1 mg of 23b (5%, t$_R$ 111 min). 23a (1α, 3β): $[\alpha]_D^{25}$ +97 (c 7.5, CHCl$_3$); $^1$H NMR (CDCl$_3$) δ7.12 (m, 1H), 6.37 (d, J=11 Hz, 1H), 6.16 (t, J=15 Hz, 1H), 6.11 (m, 2H), 6.01 (d, J=11 Hz, 1H), 5.32 (m, 1H), 4.99 (m, 1H), 4.4–64.40 (m, 1H), 4.264.19 (m, 1H), 2.83 (dd, J=12, 3.7 Hz, 1H), 2.59 (dd, J=14, 3.2 Hz, 1H), 1.36 (s, 9H), 1.09 (d, J=6.8 Hz, 3H), 0.57 (s, 3H); $^{13}$C NMR (CDCl$_3$) δ153.13, 147.58, 146.98, 142.43, 133.24, 124.78, 124.00, 120.74, 117.30, 111.83, 70.80, 66.81, 58.60, 56.09, 55.63, 46.06, 45.23, 42.83, 40.69, 40.26, 28.97, 27.45, 23.45, 23.35, 22.24, 19.69, 12.29; IR (neat) 3598–3148 (br), 3013, 2935, 2870, 1637, 1588, 1457, 1295, 1108; HRMS: calcd for C$_{29}$H$_{44}$O$_4$S 488.2960, found 488.2950. 23b (1β, 3α): $[\alpha]_D^{25}$ +32 (c 1.0, CHCl$_3$); $^1$H NMR (CDCl$_3$) δ7.12 (m, 1H), 6.38 (d, J=11 Hz, 1H), 6.16 (t, J=15 Hz, 1H), 6.11 (m, 2H), 6.01 (d, J=11 Hz, 1H), 5.32 (m, 1H), 4.99 (m, 11H), 4.474.40 (m, 1H), 4.26–4.18 (m, 1H), 2.84 (dd, J=12, 3.8 Hz, 1H), 2.61 (dd, J=14, 3.2 Hz, 1H), 1.36 (s, 9H), 1.09 (d, J=6.8 Hz, 3H), 0.57 (s, 3H); $^{13}$C NMR (CDCl$_3$) δ153.13, 147.27, 147.01, 142.52, 133.10, 124.82, 124.01, 120.76, 117.30, 112.56, 71.32, 66.75, 58.61, 56.10, 55.64, 46.07, 45.45, 42.83, 40.70, 40.25, 29.00, 27.44, 23.45, 23.38, 22.28, 19.71, 12.32; IR (neat) 3568–3087 (br), 3016, 2954, 2928, 2872, 1637, 1588, 1457, 1295, 1109; HRMS: calcd for C$_{29}$H$_{44}$O$_4$S 488.2960, found 488.2944. UV pending.

EXAMPLE 48

Assay of Pharmacological Activities

The compounds of the invention have been compared with calcitriol for biological activity.

The compounds were tested for growth inhibition of murine keratinocyte cells (cell line PE) and for the inhibition of TPA-induced ornithine decarboxylase (ODC) activity as described in U.S. Pat. No. 5,830,885.

The cell line PE was derived from a papilloma induced in female SENCAR mice by a standard skin initiation/promotion protocol (*Carcinogenesis,* 7:949–958 (1986), the entire contents of which are hereby incorporated by reference) and was chosen for its particular sensitivity to the induction of ornithine decarboxylase (ODC) activity by the extensively characterized tumor promoter TPA. The PE cell line culture medium used in the tests consisted of Eagle's minimal essential medium without calcium chloride supplemented with 8% chelexed fetal calf serum and 1% antibiotic-antimycotic and the addition of CaCl$_2$ to 0.05 mM Ca$^{++}$.

The results are shown in FIG. 1, and indicate that the compounds of the invention inhibit cell proliferation, compounds 23a and 15a being nearly as effective as calcitriol.

Figure 2:
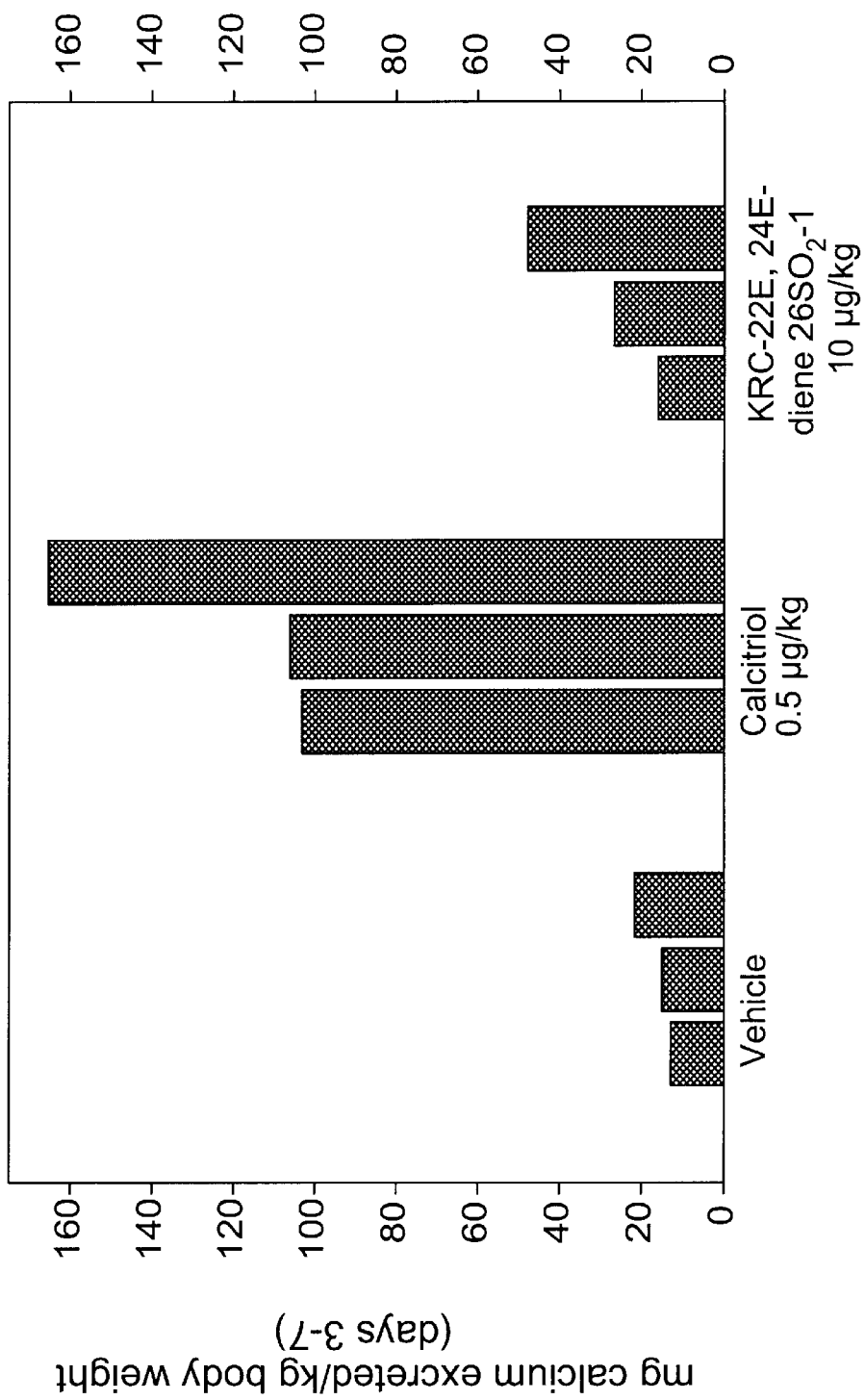
FIG. 2: Effect of 22E, 24E diene sulfone vitamin $D_3$ analog on calcium levels in rat urine. Values shown for control, calcitriol and diene sulfone analog groups, each containing three animals.
Figure 3:
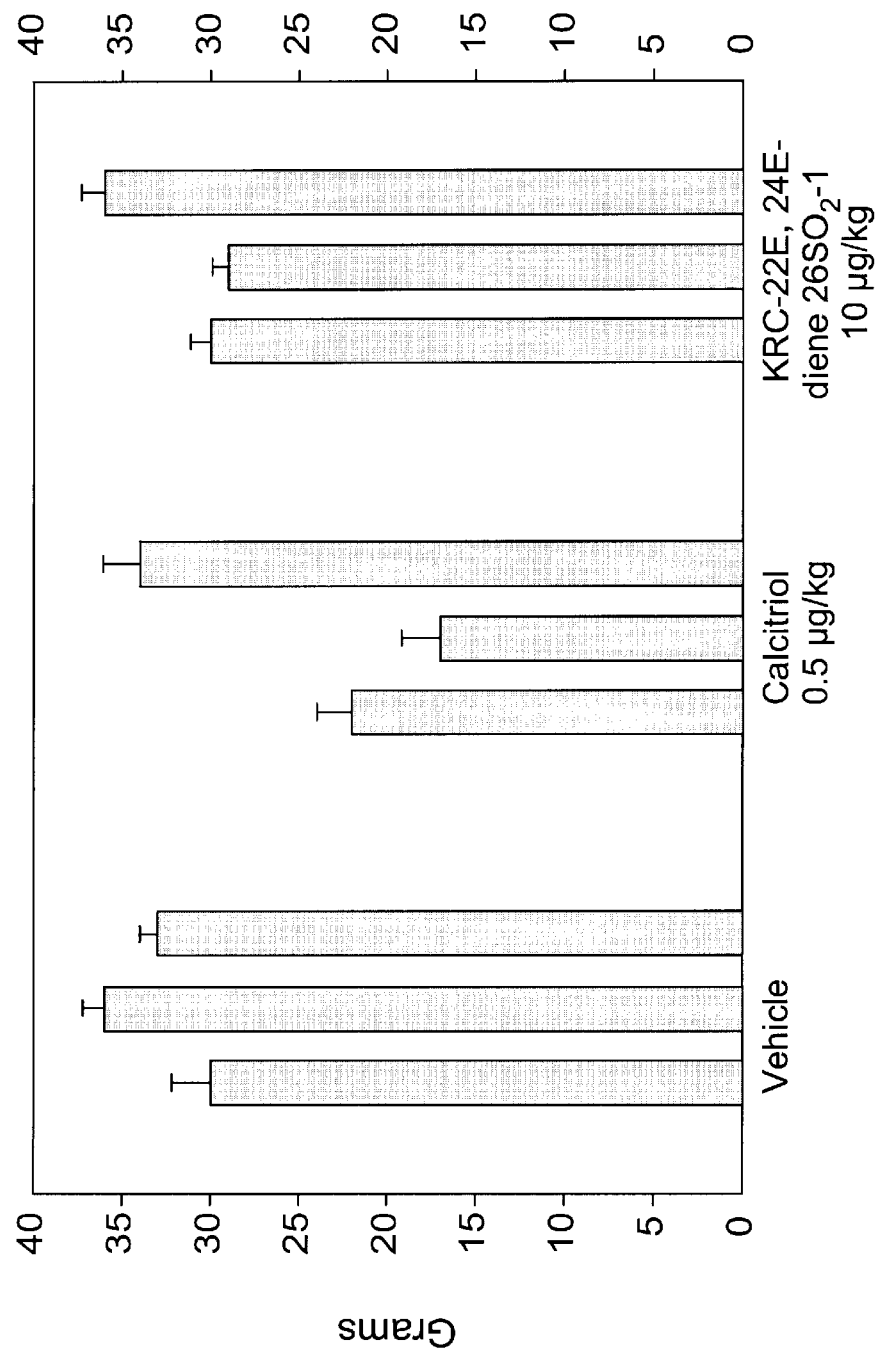
FIG. 3: Effect of 22E, 24E diene sulfone vitamin $D_3$ analog on weight gain. Weight gain of rats, days 0–7 of treatment is shown for control, calcitriol and diene sulfone analog groups, each containing three animals.

The compounds were also tested for their effect on calcium excretion and weight gain in rats according to the methods described in Posner et al., J. Med. Chem. 41:3008–3014 (1998). The results are shown in FIGS. 2 and 3, and demonstrate that the compounds of the invention do not inhibit weight gain nor stimulate calcium secretion in contrast to calcitriol.

Thus, compounds according to the invention exhibit the antiproliferative effects of vitamin D$_3$ without the associated effects on calcium excretion and weight gain exerted by vitamin D$_3$. Accordingly, they should prove valuable as therapeutic agents in diseases where excessive cell proliferation and/or failure of cells to differentiate may occur, including but not limited to psoriasis and cancer. External or internal administration of the compounds of the invention can be made in accord with the condition to be treated using methods known to those of ordinary skill in the medical and veterinary arts, with appropriate dosages determined by routine experimentation.

What is claimed is:

. A sulfur containing analog of 1α,25 dihydroxy vitamin D$_3$ selected from the group consisting of compounds represented by formulae II–X and XIV–XVII as follows:

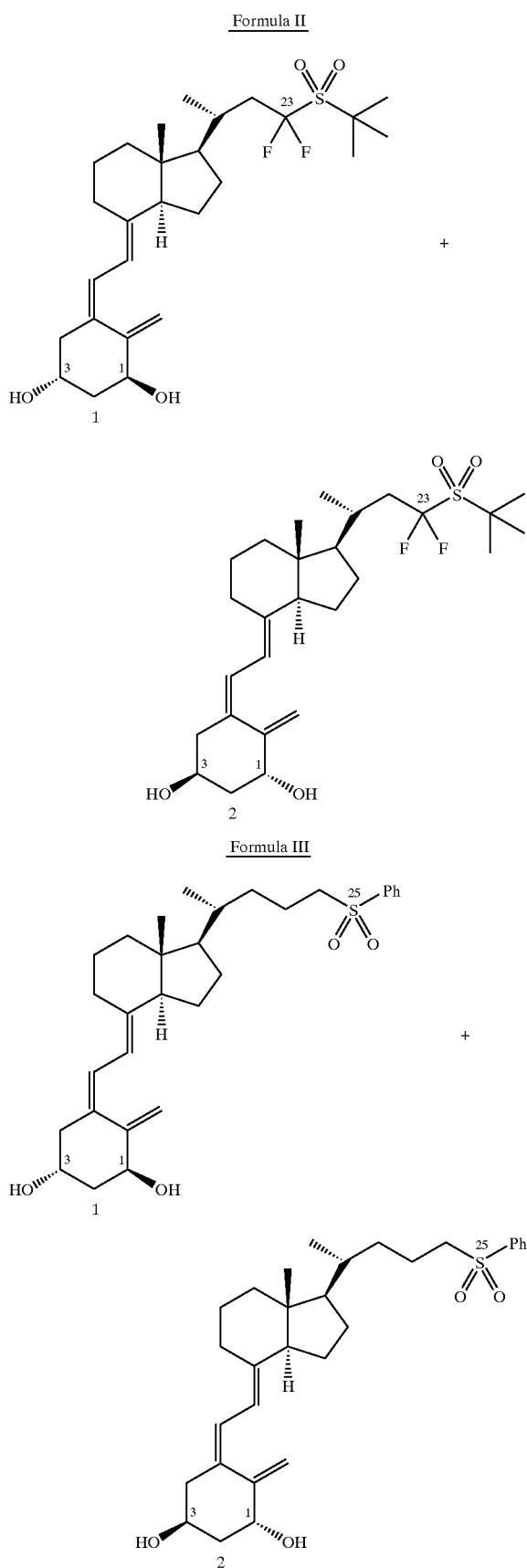

-continued
Formula IV
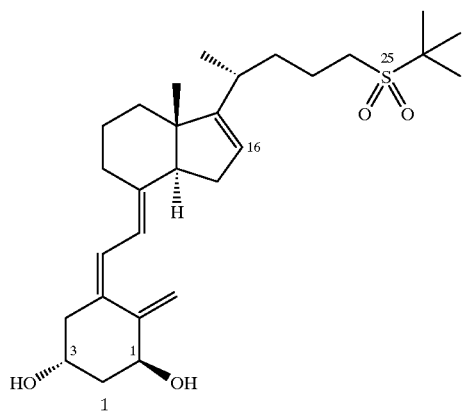
1
+
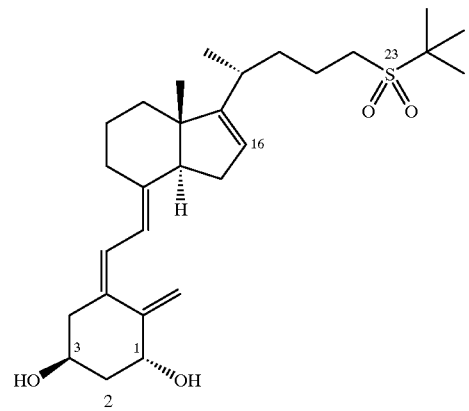
2
Formula V
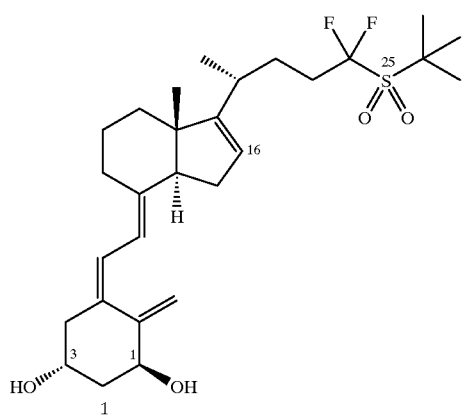
1
+
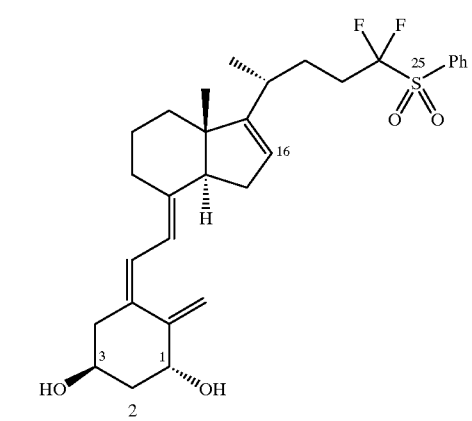
2
-continued
Formula VI
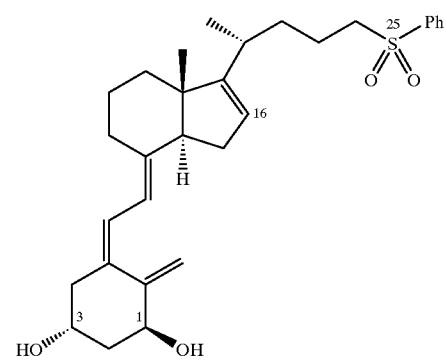
1
+
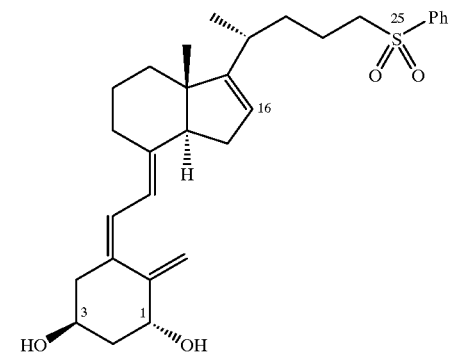
2
Formula VII
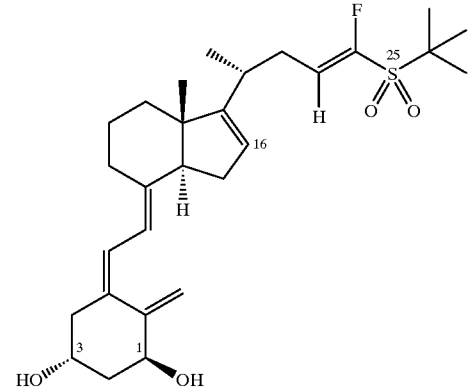
1
+
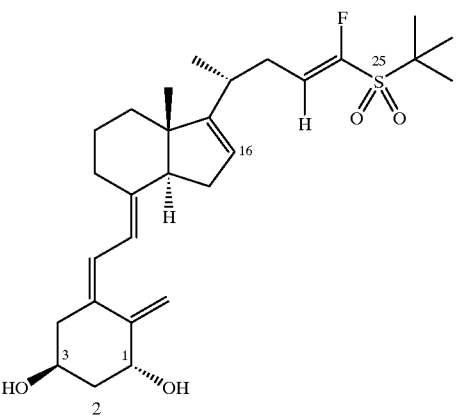
2

-continued
Formula VIII
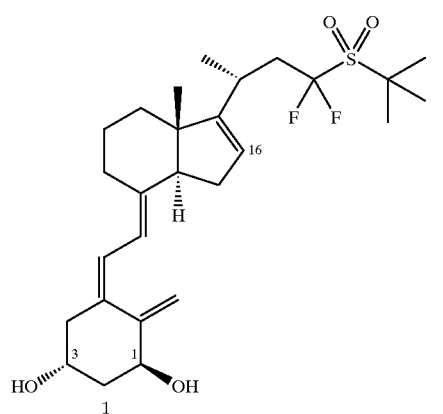
1
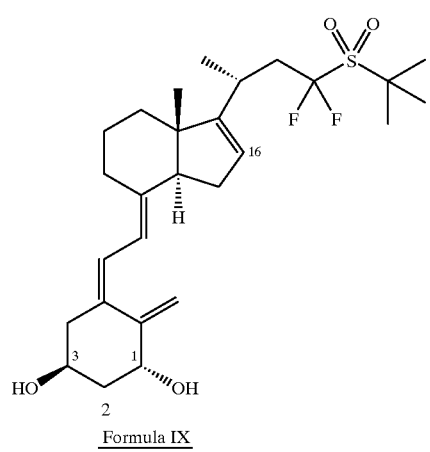
2
Formula IX
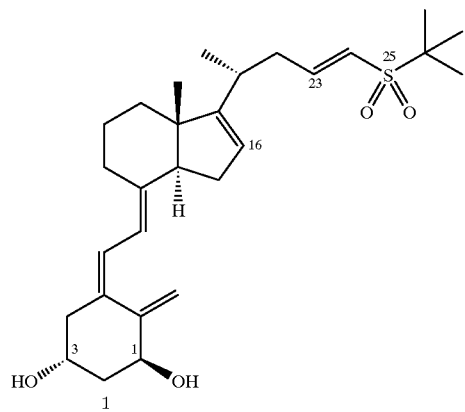
1
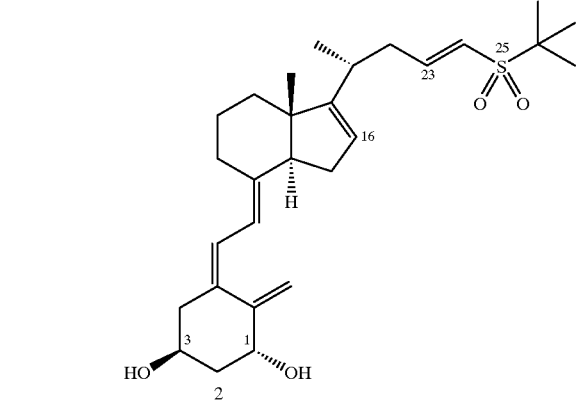
2
-continued
Formula X
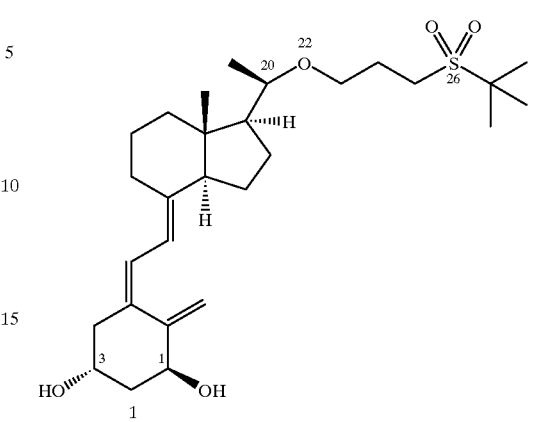
1
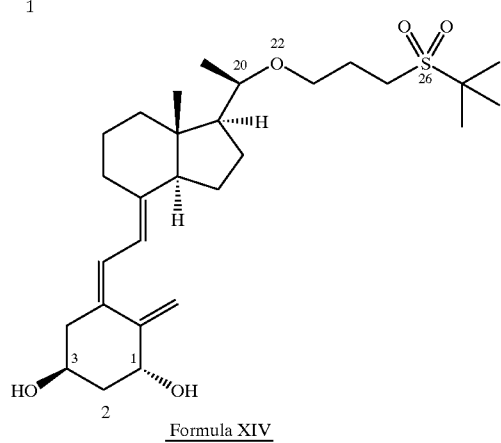
2
Formula XIV
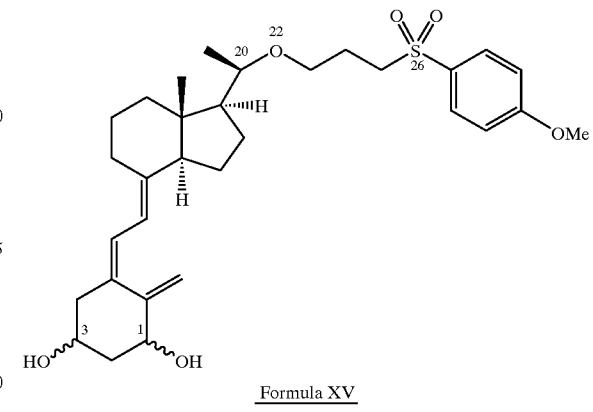
Formula XV
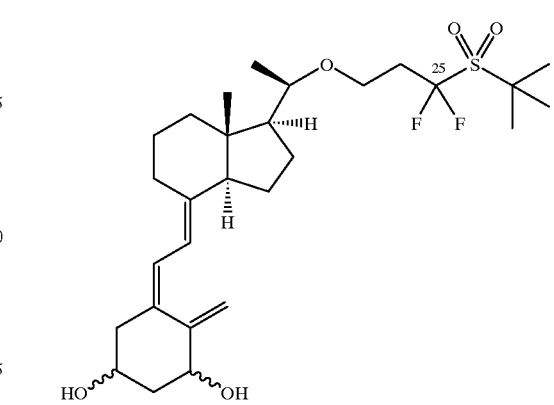

Formula XVI

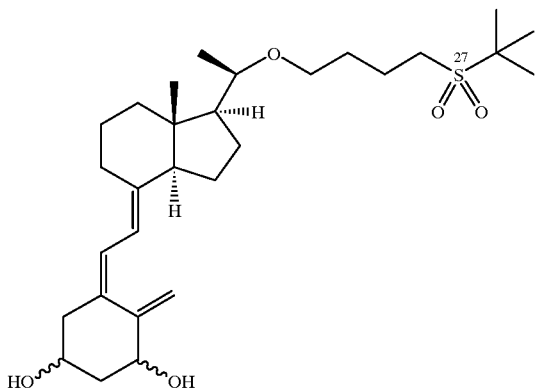

Formula XVII

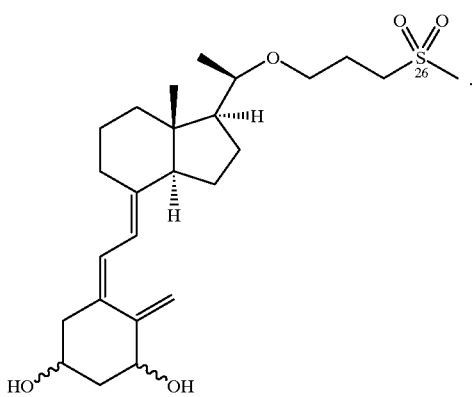

2. A vitamin $D_3$ analog according to claim 1 which is in the (+)(1β,3α) diastereomeric configuration.

3. A vitamin $D_3$ analog according to claim 1 which is in the (−)(1α,3β) diastereomeric configuration.

4. A vitamin $D_3$ analog which is a 23-oxa-25-sulfone represented by formula XI Formula XI

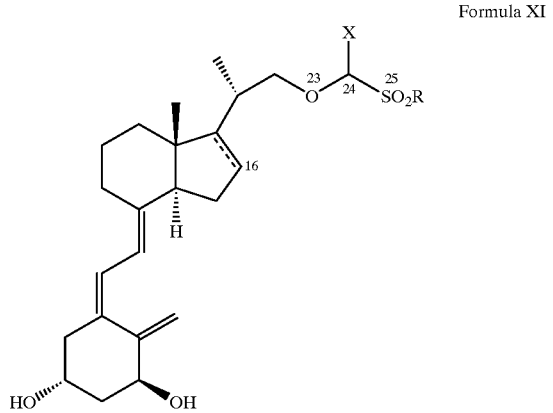

wherein X is $H_2$ or $F_2$, and R is a branched or straight chain lower alkyl, an unsubstituted phenyl group or a phenyl group substituted with a lower alkyl or alkoxy group.

5. The vitamin $D_3$ analog according to claim 4 wherein R is selected from the group consisting of methyl, t-butyl, phenyl and p-methoxyphenyl.

6. A vitamin $D_3$ analog which is a 20-epi-22-oxa-sulfone represented by Formula XII Formula XII

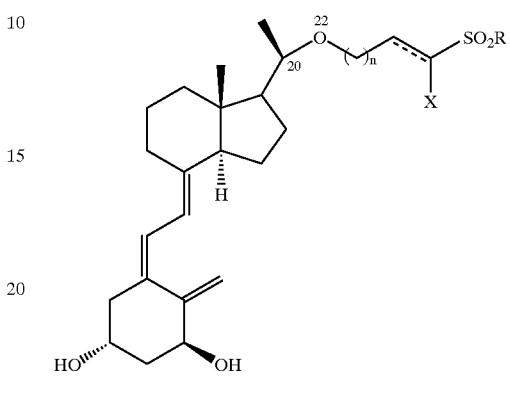

wherein n is 1 or 2, X is $H_2$ or $F_2$ and R is a branched or straight chain lower alkyl, an unsubstituted phenyl group or a phenyl group substituted with a lower alkyl or alkoxy group.

7. The vitamin $D_3$ analog according to claim 6 wherein R is selected from the group consisting of methyl, t-butyl, phenyl and p-methoxyphenyl.

8. The vitamin $D_3$ analog which is a 16-ene-alkenylsulfone or 16ene-alkynylsulfone represented by formula XIII Formula XIII

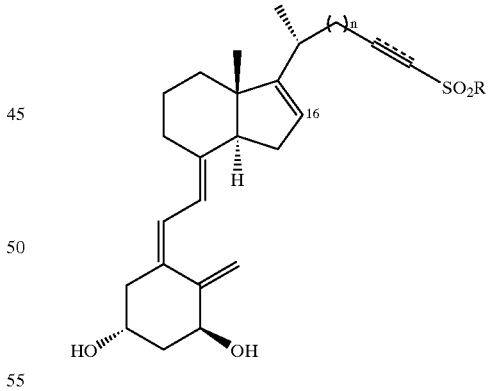

wherein n is 1 or 2 and R is a branched or straight chain lower alkyl, an unsubstituted phenyl group or a phenyl group substituted with a lower alkyl or alkoxy group.

9. The vitamin $D_3$ analog according to claim 8 wherein R is selected from the group consisting of methyl, t-butyl, phenyl and p-methoxyphenyl.

10. A vitamin $D_3$ analog which is a 22E, 24E diene sulfone represented by formula XVIII

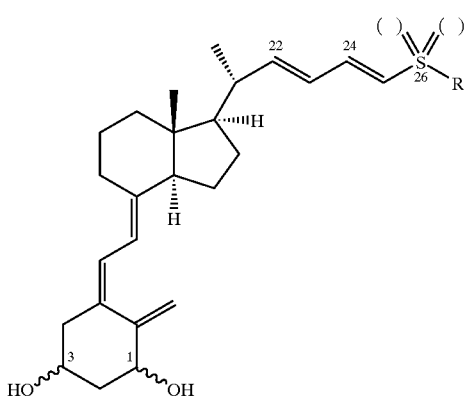

Formula XVIII wherein R is a branched or straight chain lower alkyl, an unsubstituted phenyl group or a phenyl group substituted with a lower alkyl or alkoxy group.

11. The vitamin $D_3$ analog according to claim 10 which is in the (−)(1α,3β) diastereomeric configuration.

12. The vitamin $D_3$ analog according to claim 11 wherein R is selected from the group consisting of methyl, t-butyl, phenyl and p-methoxyphenyl.

13. The vitamin $D_3$ analog according to claim 11 wherein R is t-butyl.

* * * * *

UNITED STATES PATENT AND TRADEMARK OFFICE
CERTIFICATE OF CORRECTION

PATENT NO.    : 6,380,408 B1
DATED         : April 30, 2002
INVENTOR(S)   : Posner et al.

It is certified that error appears in the above-identified patent and that said Letters Patent is hereby corrected as shown below:

Column 1,
Please replace lines 9-11, with the following paragraph:

-- The U.S. Government has a paid-license in this invention and the right in limited circumstances to require the patent owner to license others on reasonable terms as provided for by the terms of Grant No. 44530 awarded by the National Institutes of Health. --

Column 9,
Lines 50-65, and Column 71, lines 5-15, please replace Formula XVII with the Formula below:

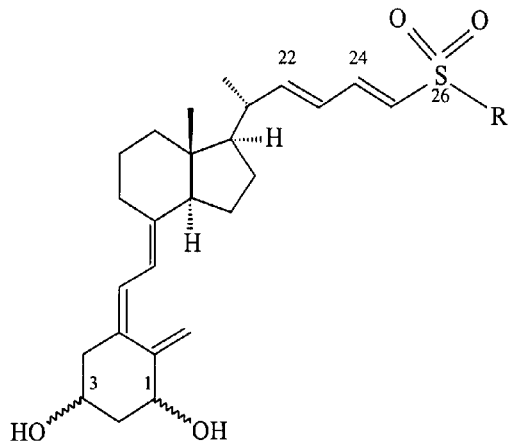

Signed and Sealed this

Twenty-eighth Day of January, 2003

JAMES E. ROGAN
*Director of the United States Patent and Trademark Office*